United States Patent
Kim et al.

(10) Patent No.: US 12,225,817 B2
(45) Date of Patent: Feb. 11, 2025

(54) CONDENSED CYCLIC COMPOUND AND ORGANIC LIGHT-EMITTING DEVICE INCLUDING THE SAME

(71) Applicants: Samsung Electronics Co., Ltd., Suwon-si (KR); Samsung SDI Co., Ltd., Yongin-si (KR)

(72) Inventors: Sangmo Kim, Hwaseong-si (KR); Hyunjung Kim, Suwon-si (KR); Soonok Jeon, Seoul (KR); Yeonsook Chung, Seoul (KR); Miyoung Chae, Suwon-si (KR); Dalho Huh, Suwon-si (KR); Eunsuk Kwon, Suwon-si (KR); Jongsoo Kim, Suwon-si (KR); Myungsun Sim, Suwon-si (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 0 days.

(21) Appl. No.: 17/739,532

(22) Filed: May 9, 2022

(65) Prior Publication Data

US 2022/0271237 A1 Aug. 25, 2022

Related U.S. Application Data

(63) Continuation of application No. 15/258,544, filed on Sep. 7, 2016, now abandoned.

(30) Foreign Application Priority Data

Sep. 9, 2015 (KR) .................. 10-2015-0127715
Aug. 29, 2016 (KR) .................. 10-2016-0110092

(51) Int. Cl.

| | |
|---|---|
| H01L 51/54 | (2006.01) |
| C07D 209/94 | (2006.01) |
| C07D 487/04 | (2006.01) |
| C07D 491/04 | (2006.01) |
| C07D 491/048 | (2006.01) |
| C07D 495/04 | (2006.01) |
| C07D 513/04 | (2006.01) |
| C07D 519/00 | (2006.01) |
| C09K 11/02 | (2006.01) |
| C09K 11/06 | (2006.01) |
| H10K 85/60 | (2023.01) |
| H10K 50/11 | (2023.01) |
| H10K 85/30 | (2023.01) |
| H10K 101/10 | (2023.01) |

(52) U.S. Cl.
CPC ....... *H10K 85/6572* (2023.02); *C07D 209/94* (2013.01); *C07D 487/04* (2013.01); *C07D 491/04* (2013.01); *C07D 491/048* (2013.01); *C07D 495/04* (2013.01); *C07D 513/04* (2013.01); *C07D 519/00* (2013.01); *C09K 11/025* (2013.01); *C09K 11/06* (2013.01); *H10K 85/657* (2023.02); *H10K 50/11* (2023.02); *H10K 85/342* (2023.02); *H10K 85/615* (2023.02); *H10K 85/631* (2023.02); *H10K 85/653* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 7,993,760 B2 | 8/2011 | Komori et al. | |
| 9,260,433 B2 | 2/2016 | Kai et al. | |
| 9,960,367 B2 | 5/2018 | Jung | |
| 2004/0110031 A1* | 6/2004 | Fukuda .......... | C09K 11/06 313/506 |
| 2008/0303415 A1 | 12/2008 | Suzuri et al. | |
| 2009/0302742 A1 | 12/2009 | Komori et al. | |
| 2010/0213443 A1 | 8/2010 | Sapochak et al. | |
| 2012/0080670 A1 | 4/2012 | Park et al. | |
| 2012/0091445 A1 | 4/2012 | Jung et al. | |
| 2012/0153272 A1 | 6/2012 | Fukuzaki et al. | |
| 2012/0235133 A1 | 9/2012 | Kai et al. | |
| 2013/0153874 A1 | 6/2013 | Kato et al. | |
| 2015/0060796 A1 | 3/2015 | Kim et al. | |
| 2015/0171340 A1 | 6/2015 | Lee et al. | |
| 2015/0236262 A1 | 8/2015 | Cho et al. | |
| 2016/0079545 A1 | 3/2016 | Fukuzaki et al. | |
| 2016/0093812 A1 | 3/2016 | Stoessel et al. | |
| 2016/0118602 A1 | 4/2016 | Kato et al. | |

FOREIGN PATENT DOCUMENTS

| | | |
|---|---|---|
| CN | 101321755 A | 11/2006 |
| EP | 1956022 A1 | 8/2008 |
| EP | 2298774 A1 | 3/2011 |
| JP | 2004273190 A | 9/2004 |
| JP | 201171460 A | 4/2011 |

(Continued)

OTHER PUBLICATIONS

Machine translation of KR-2014143618 (Year: 2014).*

(Continued)

*Primary Examiner* — Andrew K Bohaty

(74) *Attorney, Agent, or Firm* — CANTOR COLBURN LLP

(57) ABSTRACT

A condensed cyclic compound represented by Formula 1:

$$Ar_1\text{-}L_1\text{-}L_2\text{-}Ar_2 \quad \text{Formula 1}$$

wherein $Ar_1$, $Ar_2$, $L_1$, and $L_2$ are the same as described in the specification.

14 Claims, 1 Drawing Sheet

(56) References Cited

FOREIGN PATENT DOCUMENTS

| | | | | | |
|---|---|---|---|---|---|
| JP | 201191355 | A | | 5/2011 | |
| JP | 2012531738 | A | | 12/2012 | |
| JP | 2013178412 | A | | 9/2013 | |
| JP | 201428819 | A | | 2/2014 | |
| KR | 1020080085001 | A | | 9/2008 | |
| KR | 1020100138631 | A | | 12/2010 | |
| KR | 20110013445 | A | | 2/2011 | |
| KR | 20110132721 | A | | 12/2011 | |
| KR | 1020110132721 | A | | 12/2011 | |
| KR | 1020120032572 | A | | 4/2012 | |
| KR | 1020120123368 | A | | 11/2012 | |
| KR | 1020130011405 | A | | 1/2013 | |
| KR | 1020130117534 | A | | 10/2013 | |
| KR | 2014143618 | A | * | 12/2014 | |
| KR | 1020140142021 | A | | 12/2014 | |
| KR | 1020140143618 | A | | 12/2014 | |
| KR | 1020150024735 | | | 3/2015 | |
| KR | 1020150077219 | A | | 7/2015 | |
| WO | 2007063754 | A1 | | 6/2007 | |
| WO | 2009148016 | A1 | | 12/2009 | |
| WO | WO-2010107244 | A2 | * | 9/2010 | ........... C07D 273/01 |
| WO | 2010131855 | A2 | | 11/2010 | |
| WO | 2011025018 | A1 | | 3/2011 | |
| WO | 2011080972 | A1 | | 7/2011 | |
| WO | 2011125020 | A1 | | 10/2011 | |
| WO | 2014097866 | A1 | | 6/2014 | |
| WO | 2014166584 | A1 | | 10/2014 | |
| WO | 2014166586 | A1 | | 10/2014 | |

OTHER PUBLICATIONS

Chinese Patent Office on Mar. 27, 2020 in the examination of the Chinese Patent Application No. 201610806474.4, which corresponds to the U.S. Application above.
English Translation of Chinese Patent Office on Mar. 27, 2020 in the examination of the Chinese Patent Application No. 201610806474.4, which corresponds to the U.S. Application above.
English Translation of Office Action issued by the Chinese Patent Office on Aug. 26, 2020 in the examination of the Chinese Patent Application No. 201610806474.4, which corresponds to the U.S. Application above.
English Translation of Office Action issued by the Japanese Patent Office on Aug. 11, 2020 in the examination of the Japanese Patent Application No. 2016-174426, which corresponds to the U.S. Application above.
Extended Search Report issued by the European Patent Office dated Feb. 15, 2017, corresponds to Application No. 161868492.
Genzhong Ji, Practical Course of Applied Chemistry, p. 35.
Gong et al. J. Mater. Chem. 2012, 22, 2894-2899 (2012).
Machine Translation of KR 20110132721.
Office Action issued by the Chinese Patent Office on Aug. 26, 2020 in the examination of the Chinese Patent Application No. 201610806474.4, which corresponds to the U.S. Application above.
Office Action issued by the Japanese Patent Office on Aug. 11, 2020 in the examination of the Japanese Patent Application No. 2016-174426, which corresponds to the U.S. Application above.
Robert M. Silverstein,, Spectrometric Identification of Organic Compounds, East China University of Science and Technology Press, Paragraph 2 on p. 1.
Yongcheng Ning, Structural Identification of Organic Compounds and organic spectroscopy, Science Press, pp. 269-270.
English Abstract of KR 2014/0143618.
English Abstract of WO 2010-131855.
English Abstract of WO 2014-097866.
English Translation of Office Action dated Apr. 3, 2023 issued in corresponding Korean Patent Application No. 10-2016-0110092, 11 pp.
Office Action dated Apr. 3, 2023 issued in corresponding Korean Patent Application No. 10-2016-0110092, 10 pp.

* cited by examiner

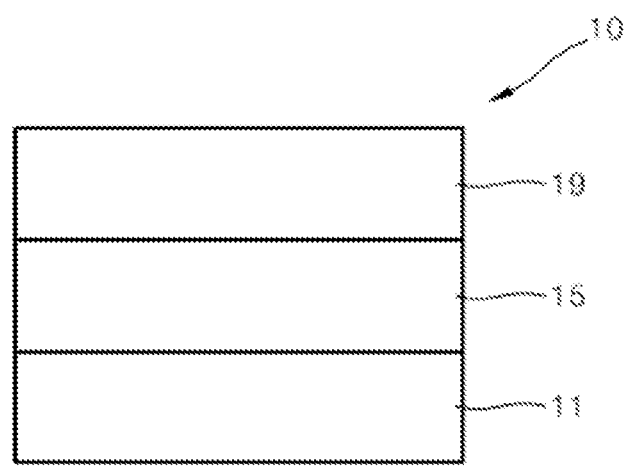

CONDENSED CYCLIC COMPOUND AND ORGANIC LIGHT-EMITTING DEVICE INCLUDING THE SAME

CROSS-REFERENCE TO RELATED APPLICATION

This continuation application of U.S. application Ser. No. 15/258,544, filed Sep. 7, 2016, claims priority to Korean Patent Application No. 10-2015-0127715, filed on Sep. 9, 2015, and Korean Patent Application No. 10-2016-0110092 filed on Aug. 29, 2016, in the Korean Intellectual Property Office, the contents of which are incorporated herein in their entirety by reference.

BACKGROUND

1. Field

The present disclosure relates to a condensed cyclic compound and an organic light-emitting device including the condensed cyclic compound.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode, wherein the organic layer may include an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons change from an excited state to a ground state to thereby generate light.

Different types of organic light emitting devices are known. However, there still remains a need in OLEDs having low driving voltage, high efficiency, high brightness, and long lifespan.

SUMMARY

Provided are a condensed cyclic compound and an organic light-emitting device including the condensed cyclic compound.

Additional aspects will be set forth in part in the description which follows and, in part, will be apparent from the description, or may be learned by practice of the presented exemplary embodiments.

According to an aspect of an exemplary embodiment, provided is a condensed cyclic compound represented by Formula 1:

Formula 1

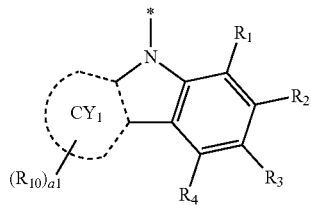

Formula 2

Formula 3

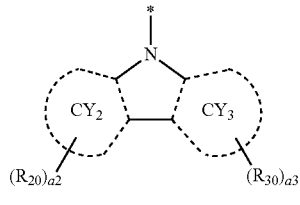

Formula 4

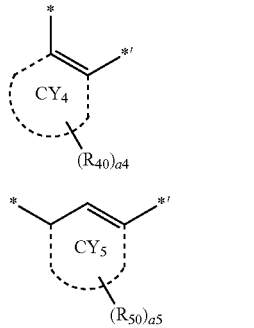

Formula 5 in Formulae 1 to 5, $Ar_1$ may be a group represented by Formula 2, $Ar_2$ may be a group represented by Formula 3, $CY_1$ may be selected from a fluorene group, a carbazole group, a dibenzofuran group, and a dibenzothiophene group, $CY_2$ and $CY_3$ may be each independently selected from a benzene group, a fluorene group, a carbazole group, a dibenzofuran group, and a dibenzothiophene group, $L_1$ and $L_2$ may be each independently a group represented by Formula 4 or group represented by Formula 5, and at least one of $L_1$ and $L_2$ is selected from groups represented by Formula 4, $CY_4$ and $CY_5$ may be each independently selected from $C_5$-$C_{30}$ carbocyclic groups, $R_1$ to $R_4$, $R_{10}$, $R_{20}$ and $R_{30}$ may be each independently selected from a hydrogen, a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{60}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{10}$ aryl group, a substituted or unsubstituted $C_6$-$C_{10}$ aryloxy group, a substituted or unsubstituted $C_6$-$C_{10}$ arylthio group, a substituted or unsubstituted $C_7$-$C_{10}$ arylalkyl group, a substituted or unsubstituted $C_1$-$C_{10}$ heteroaryl group, a substituted or unsubstituted $C_2$-$C_{60}$ heteroaryloxy group, a substituted or unsubstituted $C_2$-$C_{10}$ heteroarylthio group, a substituted or unsubstituted $C_3$-$C_{10}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), $R_{40}$ and $R_{50}$ may be each independently a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{10}$ aryl group, a substituted or unsubstituted $C_6$-$C_{10}$ aryloxy group, a substituted or unsubstituted $C_6$-$C_{10}$ arylthio group, a substituted or unsubstituted $C_7$-$C_{60}$ arylalkyl group, a substituted or unsubstituted $C_1$-$C_{10}$ heteroaryl group, a substituted or unsubstituted $C_2$-$C_{10}$ heteroaryloxy group, a substituted or unsubstituted $C_2$-$C_{60}$ heteroarylthio group, a substituted or unsubstituted $C_3$-$C_{10}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), a1 to a5 may each independently be an integer of 0 to 10, each of * and *' is a binding site to a neighboring atom, and at least one substituent of the substituted $C_1$-$C_{10}$ alkyl group, substituted $C_2$-$C_{60}$ alkenyl group, substituted $C_2$-$C_{10}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{10}$ heteroaryl group, substituted $C_2$-$C_{10}$ heteroaryloxy group, substituted $C_2$-$C_{10}$ heteroarylthio group, substituted $C_3$-$C_{10}$ heteroarylalkyl group, substituted monovalent non-aromatic condensed polycyclic group and substituted monovalent non-aromatic condensed heteropolycyclic group may be selected from a deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{60}$ alkynyl group and a $C_1$-$C_{10}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_6$ heteroaryl group, a $C_2$-$C_{60}$ heteroaryloxy group, a $C_2$-$C_{10}$ heteroarylthio group, a $C_3$-$C_{10}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$) and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{10}$ heteroarylthio group, a $C_3$-$C_{10}$ heteroarylalkyl group, a monovalent non-aromatic condensed polycyclic group and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{10}$ heteroarylthio group, a $C_3$-$C_{10}$ heteroarylalkyl group, a monovalent non-aromatic condensed polycyclic group and a monovalent non-aromatic condensed heteropolycyclic group, each substituted with at least one selected from a deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{10}$ heteroaryloxy group, a $C_2$-$C_{10}$ heteroarylthio group, a $C_3$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$); and —Si($Q_{31}$)($Q_{32}$)($Q_{33}$), —N($Q_{34}$)($Q_{35}$) and —B($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ may be each independently selected from a hydrogen, a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{60}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{10}$ heteroaryl group, a substituted or unsubstituted $C_2$-$C_{10}$ heteroaryloxy group, a substituted or unsubstituted $C_2$-$C_{60}$ heteroarylthio group, a substituted or unsubstituted $C_3$-$C_{10}$ heteroarylalkyl group, a substituted or unsubstituted monovalent non-aromatic condensed polycyclic group and a substituted or unsubstituted monovalent non-aromatic condensed heteropolycyclic group.

According to another aspect of an exemplary embodiment, provided is an organic light-emitting device including:
a first electrode;
a second electrode; and
an organic layer disposed between the first electrode and the second electrode,
wherein the organic layer includes an emission layer, and
wherein the organic layer includes one or more of the condensed cyclic compounds represented by Formula 1.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 illustrates a schematic view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A condensed cyclic compound may be represented by Formula 1.

Formula 1

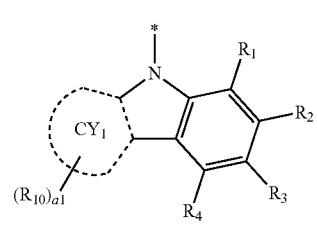

Formula 2

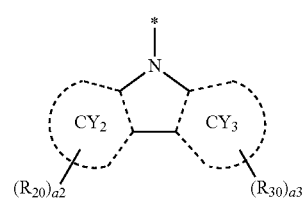

Formula 3

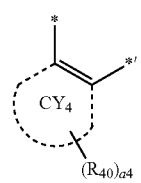

Formula 4

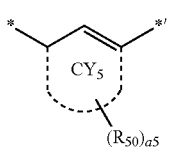

Formula 5

In Formula 1, $Ar_1$ may be a group represented by Formula 2 and $Ar_2$ may be a group represented by Formula 3.

$CY_1$ in Formula 2 may be selected from a fluorene group, a carbazole group, a dibenzofuran group, and a dibenzothiophene group, and $CY_2$ and $CY_3$ in Formula 3 may be each independently selected from a benzene group, a fluorene group, a carbazole group, a dibenzofuran group, and a dibenzothiophene group.

$L_1$ and $L_2$ in Formula 1 may be each independently a group represented by Formula 4 or a group represented by Formula 5, and at least one of $L_1$ and $L_2$ may be selected from groups represented by Formula 4.

$CY_4$ and $CY_5$ in Formulae 4 and 5 may be each independently selected from $C_5$-$C_{30}$ carbocyclic groups.

$R_1$ to $R_4$, $R_{10}$, $R_{20}$ and $R_{30}$ in Formulae 2 to 5 may be each independently selected from a hydrogen, a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{10}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{10}$ heteroaryloxy group, a substituted or unsubstituted $C_2$-$C_{60}$ heteroarylthio group, a substituted or unsubstituted $C_3$-$C_{10}$ heteroarylalkyl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_4)(Q_5)$, and $-B(Q_6)(Q_7)$, and $R_{40}$ and $R_{50}$ may be each independently selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{10}$ heteroaryl group, a substituted or unsubstituted $C_2$-$C_{10}$ heteroaryloxy group, a substituted or unsubstituted $C_2$-$C_{60}$ heteroarylthio group, a substituted or unsubstituted $C_3$-$C_{10}$ heteroarylalkyl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_4)(Q_5)$, and $-B(Q_6)(Q_7)$.

a1, a2, a3, a4 and a5 in Formulae 2-5 respectively denote the number of $R_{10}$(s), $R_{20}$(s), $R_{30}$(s), $R_{40}$(s) and $R_{50}$(s), and may each independently be an integer of 0 to 10.

When a1 is 2 or more, two or more $R_{10}$(s) are the same or different; when a2 is 2 or more, two or more $R_{20}$(s) are the same or different; when a3 is 2 or more, two or more $R_{30}$(s) are the same or different; when a4 is 2 or more, two or more $R_{40}$(s) are the same or different; and when a5 is 2 or more, two or more $R_{50}$(s) are the same or different.

Each of * and *' in Formulae 2 to 5 is a binding site to a neighboring atom.

According to an embodiment, in Formula 1, $Ar_1$ may be selected from groups represented by Formulae 2-1 to 2-6 and $Ar_2$ may be selected from groups represented by Formulae 3-1 to 3-7, but embodiments are not limited thereto:

Formula 2-1

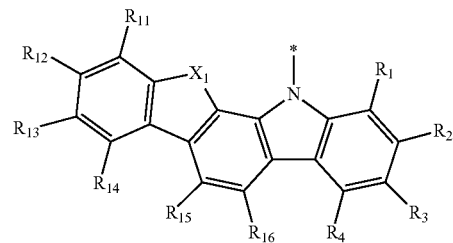

Formula 2-2
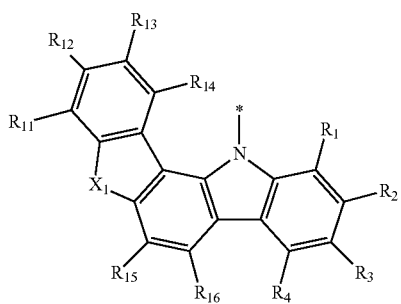
Formula 2-3
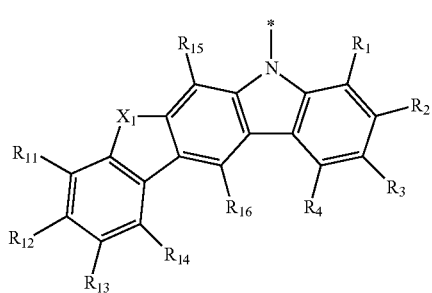
Formula 2-4
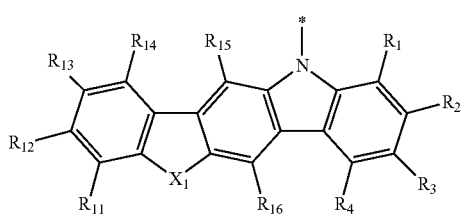
Formula 2-5
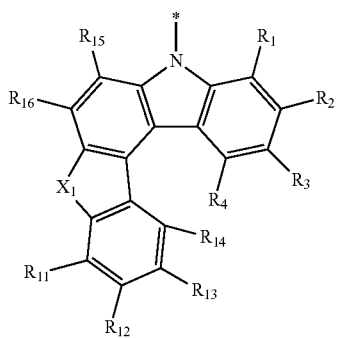
Formula 2-6
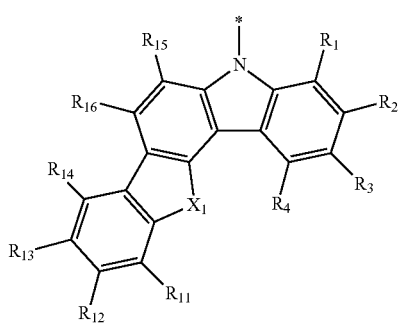
Formula 3-1
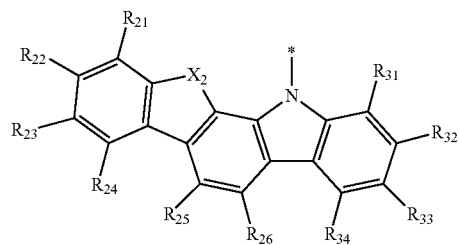
Formula 3-2
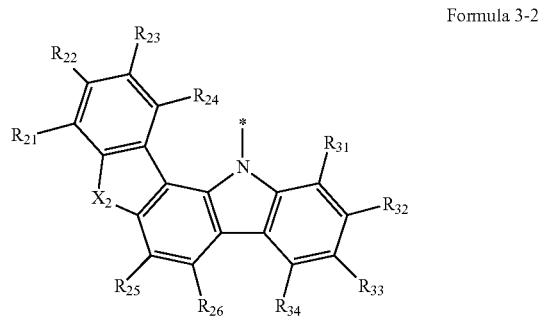
Formula 3-3
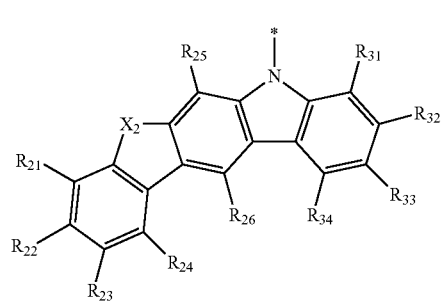
Formula 3-4
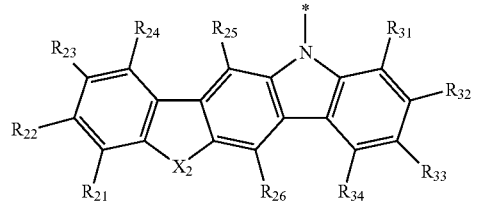
Formula 3-5
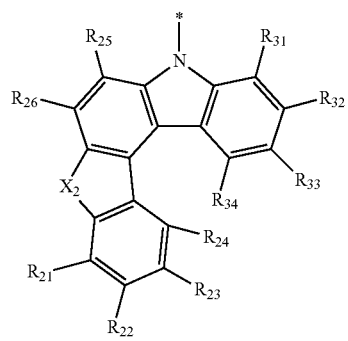

Formula 3-6

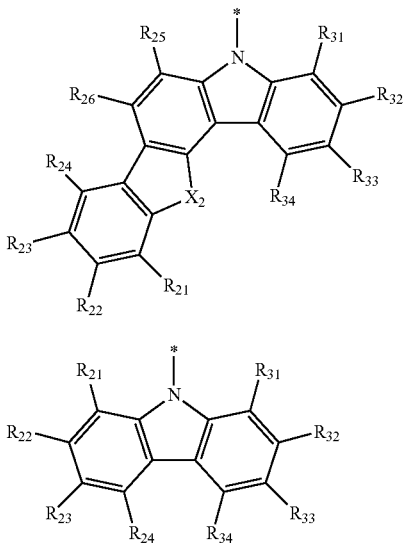

Formula 3-7

In Formulae 2-1 to 2-6 and 3-1 to 3-7,
$X_1$ may be $C(R_{17})(R_1)$, $N(R_{19})$, O or S,
$X_2$ may be $C(R_{27})(R_{28})$, $N(R_{29})$, O or S,
descriptions of $R_1$ to $R_4$ are the same as provided herein,
descriptions of $R_{11}$ to $R_{19}$ are the same as the description of $R_{10}$,
descriptions of $R_{21}$ to $R_{29}$ are the same as the description of $R_{20}$,
descriptions of $R_{31}$ to $R_{34}$ are the same as the description of $R_{30}$, and
* is a binding site to a neighboring atom.

For example, $R_1$ to $R_4$, $R_{11}$ to $R_{19}$, $R_{21}$ to $R_{29}$ and $R_{31}$ to $R_{34}$ in Formulae 2-1 to 2-6 and 3-1 to 3-7 may be each independently selected from a hydrogen, a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group and a pyridobenzothiazinyl group, each substituted with at least one selected from a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$) and —B($Q_{36}$)($Q_{37}$); and —Si($Q_1$)($Q_2$)($Q_3$), —N($Q_4$)($Q_5$), and —B($Q_6$)($Q_7$), wherein $Q_1$ to $Q_7$ and $Q_{31}$ to $Q_{37}$ may be each independently selected from a hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group and a dibenzothiophenyl group.

In some embodiments, $R_1$ to $R_4$, $R_{11}$ to $R_{19}$, $R_{21}$ to $R_{29}$ and $R_{31}$ to $R_{34}$ in Formulae 2-1 to 2-6 and 3-1 to 3-7 may be each independently selected from a hydrogen, a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group, each substituted with at least one selected from a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{20}$ alkyl group, a $C_1$-$C_{20}$ alkoxy group, a phenyl group, a biphenyl group, a terphenyl group and a naphthyl group.

In some embodiments, $R_1$ to $R_4$, $R_{11}$ to $R_{19}$, $R_{21}$ to $R_{29}$ and $R_{31}$ to $R_{34}$ in Formulae 2-1 to 2-6 and 3-1 to 3-7 may be each independently selected from a hydrogen, a deuterium, a cyano group (CN), a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a cyano group (CN), a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group, each substituted with at least one selected from a deuterium, a cyano group, a $C_1$-$C_{20}$ alkyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{20}$ alkyl group, a $C_1$-$C_{20}$ alkoxy group, a phenyl group, a biphenyl group, a terphenyl group and a naphthyl group, but embodiments are not limited thereto.

In some embodiments, $X_1$ in Formula 2-1 to 2-6 may be O or S, but embodiments are not limited thereto.

In some embodiments, $X_1$ and $X_2$ in Formulae 2-1 to 2-6 and Formulae 3-1 to 3-6 may each independently be O or S.

In some embodiments, $Ar_1$ may be the same as $Ar_2$ in Formula 1; or each of $CY_2$ and $CY_3$ in Formula 3 may be a benzene group, but embodiments are not limited thereto.

In some embodiments, in Formula 1, $Ar_1$ may be represented by Formula 2-1, $Ar_2$ may be represented by Formula 3-1;

$Ar_1$ may be represented by Formula 2-2, $Ar_2$ may be represented by Formula 3-2; or $Ar_1$ may be represented by Formula 2-6, and $Ar_2$ may be represented by Formula 3-6, but embodiments are not limited thereto.

In some embodiments, $L_1$ may be the same as $L_2$ in Formula 1.

$CY_4$ and $CY_5$ in Formulae 4 and 5 may be each independently selected from a benzene group, a naphthalene group, a fluorene group, a carbazole group, a dibenzofuran group, and a dibenzothiophene group.

According to an embodiment, $L_1$ and $L_2$ may be each independently selected from groups represented by Formula 4.

For example, $L_1$ and $L_2$ may be each independently selected from groups represented by Formula 4, and $L_1$ may be different than $L_2$.

Alternatively, $L_1$ and $L_2$ may be each independently selected from groups represented by Formula 4, and $L_1$ may be the same as $L_2$.

According to an embodiment, the condensed cyclic compound may be represented by one of Formulae 1-1 to 1-3:

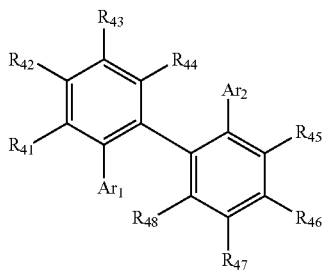

Formula 1-1

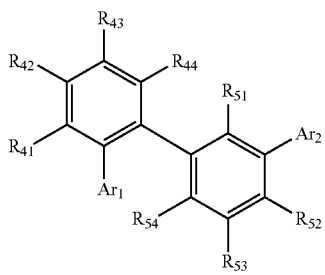

Formula 1-2

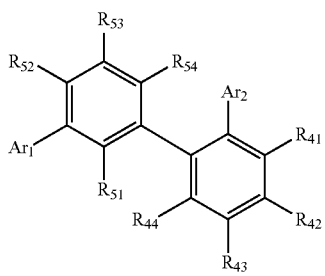

Formula 1-3

In Formulae 1-1 to 1-3, descriptions of $Ar_1$ and $Ar_2$ are the same as provided herein, descriptions of $R_{41}$ to $R_{48}$ are each independently the same as the description of $R_{40}$, and descriptions of $R_{51}$ to $R_{54}$ are each independently the same as the description of $R_{50}$.

According to an embodiment, the condensed cyclic compound may be represented by Formula 1-1, but embodiments are not limited thereto.

$R_{41}$ to $R_{48}$ and $R_{51}$ to $R_{54}$ in Formulae 1-1 to 1-3 may be each independently selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group, each substituted with at least one selected from a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{20}$ alkyl group, a $C_1$-$C_{20}$ alkoxy group, a phenyl group, a biphenyl group, a terphenyl group and a naphthyl group.

In some embodiments, $R_{41}$ to $R_{48}$ and $R_{51}$ to $R_{54}$ in Formulae 1-1 to 1-3 may be each independently selected from a hydrogen, a deuterium, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group, each substituted with at least one selected from a deuterium, a $C_1$-$C_{20}$ alkyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{20}$ alkyl group, a $C_1$-$C_{20}$ alkoxy group, a phenyl group, a biphenyl group, a terphenyl group and a naphthyl group, but embodiments are not limited thereto.

According to an embodiment, the condensed cyclic compound may be represented by one of Formulae 1-1 to 1-3, An in Formulae 1-1 to 1-3 may be selected from groups represented by Formulae 2-1 to 2-6, and $Ar_2$ may be selected from groups represented by Formulae 3-1 to 3-7.

In some embodiments, the condensed cyclic compound may be represented by one of Formulae 1-1 to 1-3, An in Formulae 1-1 to 1-3 may be selected from groups represented by Formulae 2-1 to 2-6, and $Ar_2$ may be selected from groups represented by Formulae 3-1 to 3-7, $R_1$ to $R_4$, $R_{11}$ to $R_{19}$, $R_{21}$ to $R_{29}$ and $R_{31}$ to $R_{34}$ may be each independently selected from a hydrogen, a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group;

$C_1$-$C_{20}$ alkyl group and $C_1$-$C_{20}$ alkoxy group, each substituted with at least one selected from a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group, each substituted with at least one selected from a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), $R_{41}$ to $R_{48}$ and $R_{51}$ to $R_{54}$ may be each independently selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a carbazolyl group, a furanyl group, a benzofuranyl group, a thiophenyl group, a benzothiophenyl group, a dibenzofuranyl group, a dibenzothiophenyl group, a benzocarbazolyl group and a dibenzocarbazolyl group, each substituted with at least one selected from a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{20}$ alkyl group, a $C_1$-$C_{20}$ alkoxy group, a phenyl group, a biphenyl group, a terphenyl group and a naphthyl group.

In some embodiments, the condensed cyclic compound may be represented by one of Formulae 1-1 to 1-3, and in Formulae 1-1 to 1-3, $Ar_1$ may be selected from groups represented by Formulae 2-1 to 2-6, and Ar$_2$ may be selected from groups represented by Formulae 3-1 to 3-7, R$_1$ to R$_4$, R$_{11}$ to R$_{19}$, R$_{21}$ to R$_{29}$ and R$_{31}$ to R$_{34}$ may be each independently selected from a hydrogen, a deuterium, a cyano group (CN), a C$_1$-C$_{20}$ alkyl group and a C$_1$-C$_{20}$ alkoxy group;

a C$_1$-C$_{20}$ alkyl group and a C$_1$-C$_{20}$ alkoxy group, each substituted with at least one selected from a deuterium, a cyano group (CN), a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group, each substituted with at least one selected from a deuterium, a cyano group, a C$_1$-C$_{20}$ alkyl group, a C$_1$-C$_{20}$ alkoxy group, a phenyl group, a biphenyl group, a terphenyl group, a naphthyl group and —Si(Q$_{31}$)(Q$_{32}$)(Q$_{33}$); and —Si(Q$_1$)(Q$_2$)(Q$_3$), R$_{41}$ to R$_{48}$ and R$_{51}$ to R$_{54}$ may be each independently selected from a hydrogen, a deuterium, a C$_1$-C$_{20}$ alkyl group and a C$_1$-C$_{20}$ alkoxy group;

a C$_1$-C$_{20}$ alkyl group and a C$_1$-C$_{20}$ alkoxy group, each substituted with at least one selected from a deuterium, a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group, each substituted with at least one selected from a deuterium, a C$_1$-C$_{20}$ alkyl group, a C$_1$-C$_{20}$ alkoxy group, a phenyl group, a biphenyl group, a terphenyl group, a naphthyl group and —Si(Q$_{31}$)(Q$_{32}$)(Q$_{33}$); and —Si(Q$_1$)(Q$_2$)(Q$_3$), wherein Q$_1$ to Q$_3$ and Q$_{31}$ to Q$_{33}$ may be each independently selected from a hydrogen, a C$_1$-C$_{20}$ alkyl group, a C$_1$-C$_{20}$ alkoxy group, a phenyl group, a biphenyl group, a terphenyl group and a naphthyl group, but embodiments are not limited thereto.

In some embodiments, the condensed cyclic compound may be represented by one of Formulae 1-1 to 1-3; in Formula 1-1 to 1-3, Ar$_1$ may be selected from groups represented by Formulae 2-1 to 2-6 and Ar$_2$ may be selected from groups represented by Formulae 3-1 to 3-7; and X$_1$ in Formulae 2-1 to 2-6 may be O or S (for example, X$_1$ and X$_2$ in Formulae 2-1 to 2-6 and 3-1 to 3-6 may each independently be O or S).

In some embodiments, the condensed cyclic compound may be represented by Formula 1-1, and in Formula 1-1, Ar$_1$ may be selected from groups represented by Formulae 2-1 to 2-6 and Ar$_2$ may be selected from groups represented by Formulae 3-1 to 3-7.

In some embodiments, the condensed cyclic compound may be represented by Formula 1-1; in Formula 1-1, Ar$_1$ may be selected from groups represented by Formulae 2-1 to 2-6 and Ar$_2$ may be selected from groups represented by Formulae 3-1 to 3-7; and X$_1$ in Formulae 2-1 to 2-6 may be O or S (for example, X$_1$ and X$_2$ in Formulae 2-1 to 2-6 and 3-1 to 3-6 may each independently be O or S).

The condensed cyclic compound may be selected from Compounds 1 to 108, but embodiments are not limited thereto:

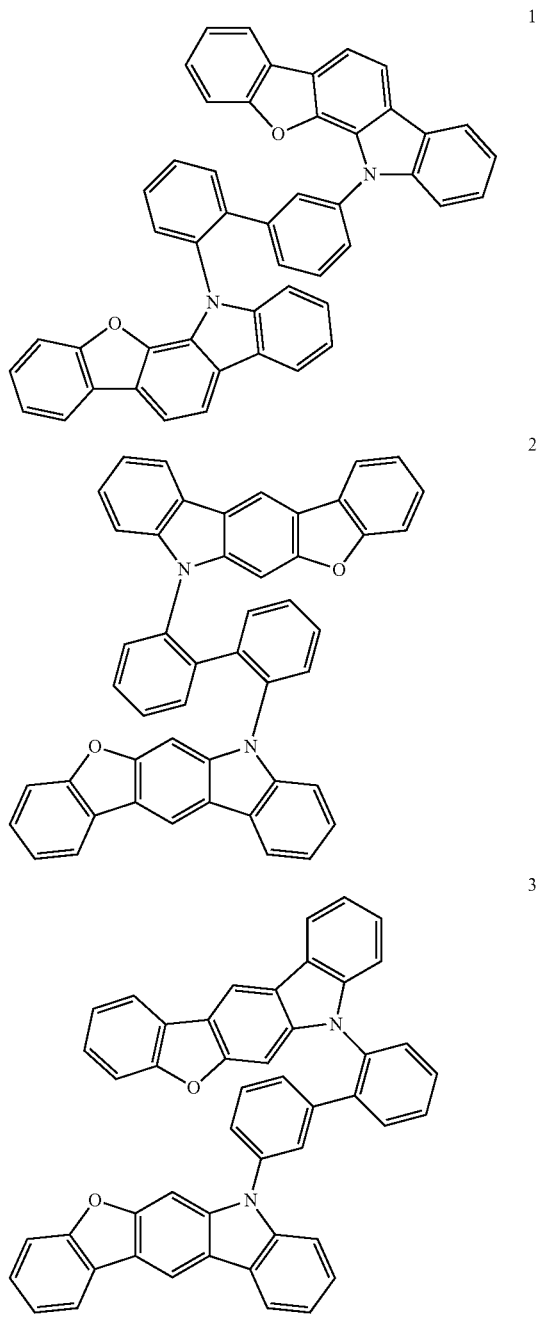

4
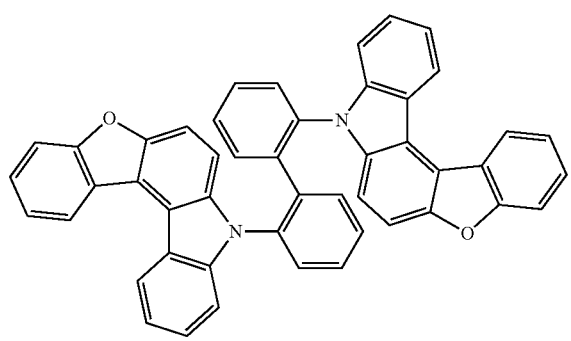
5
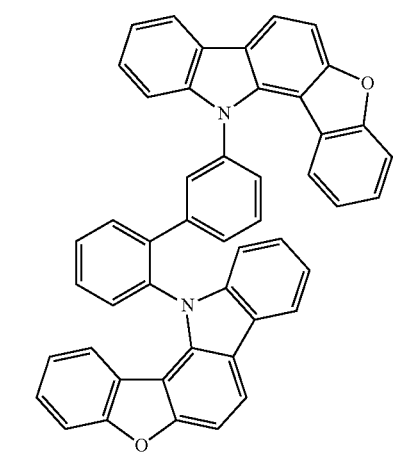
6
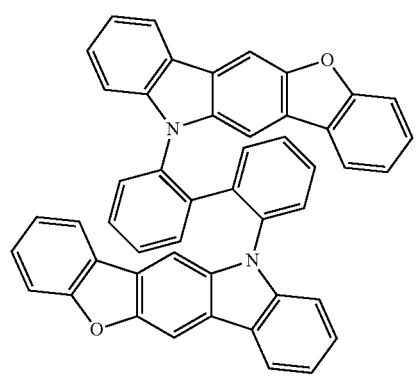
7
8
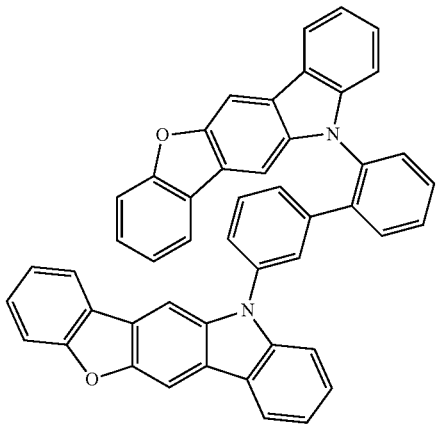
9
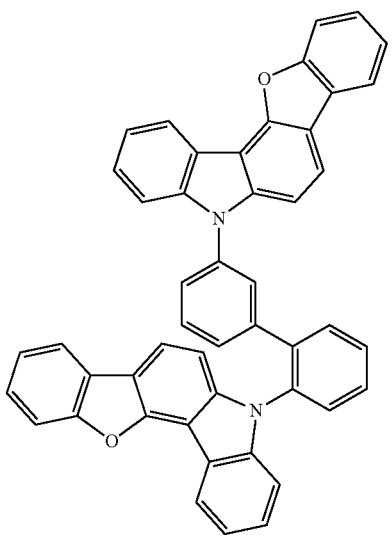
10
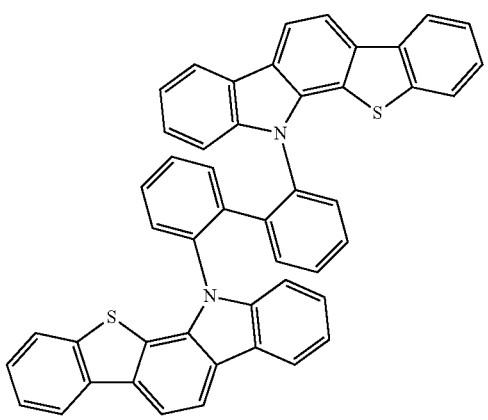

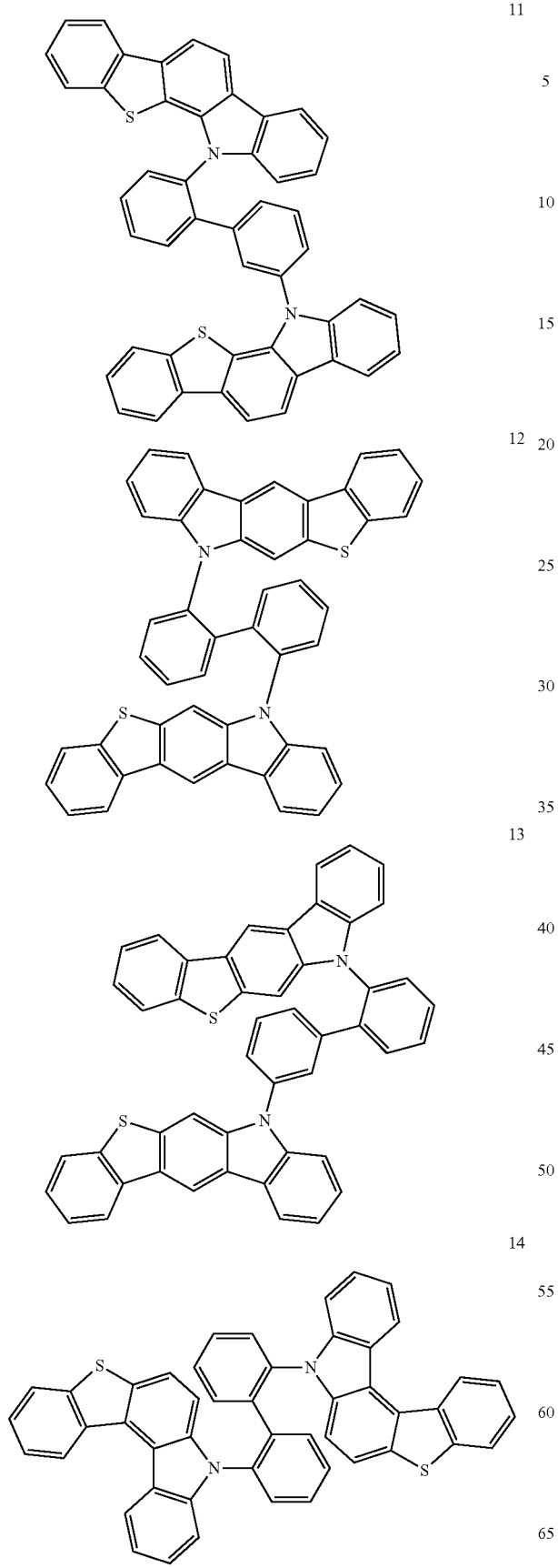

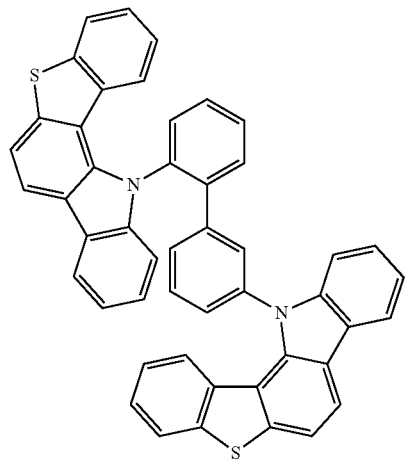
18
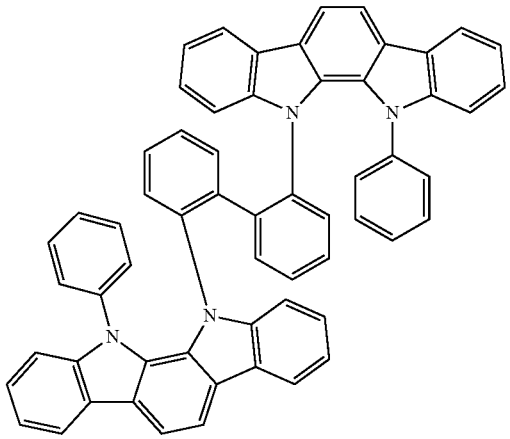
21
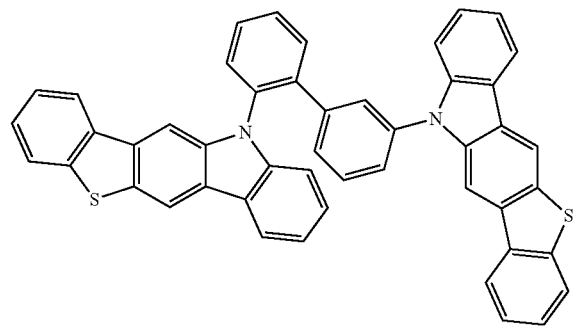
19
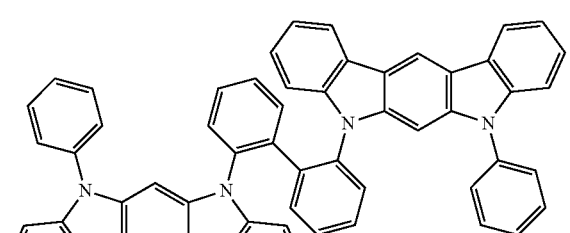
22
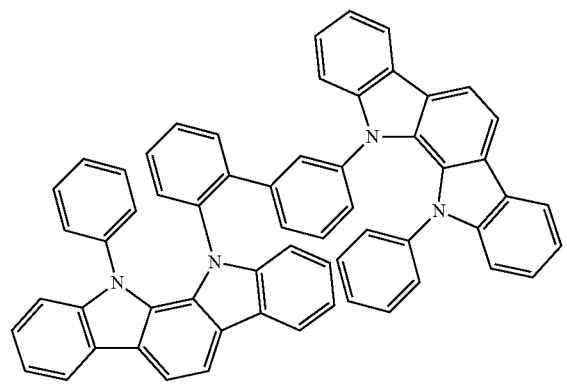
23
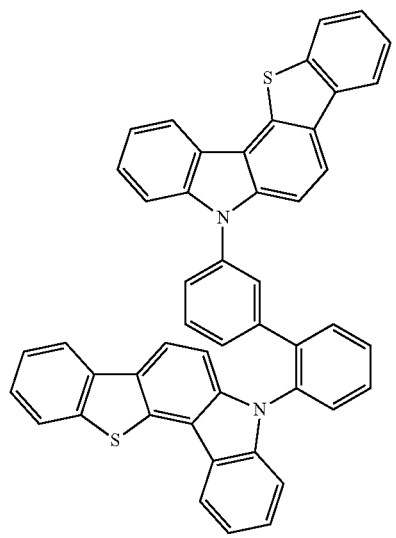
20
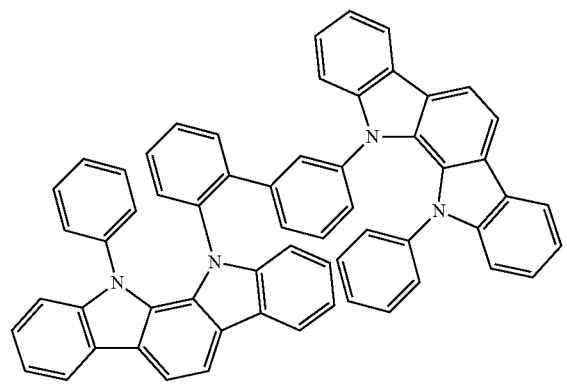
24

25
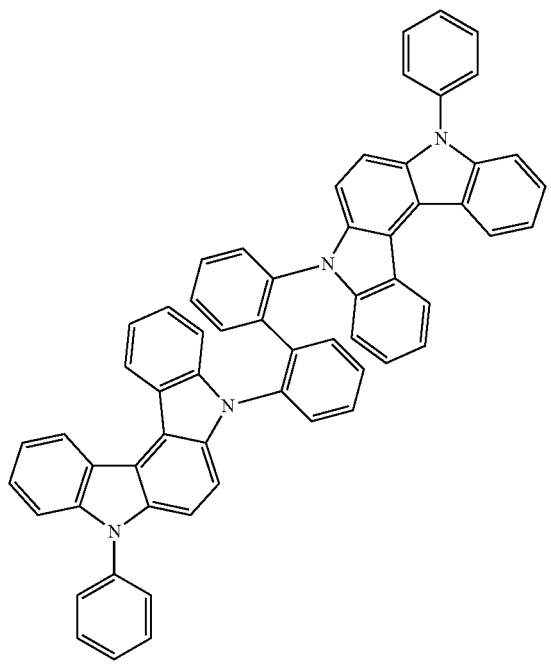
26
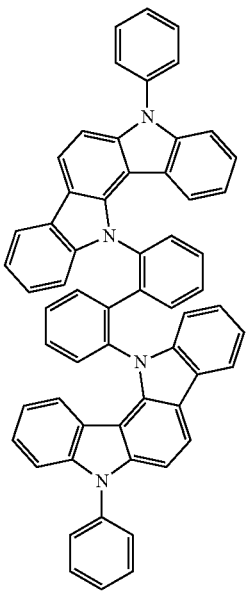
27
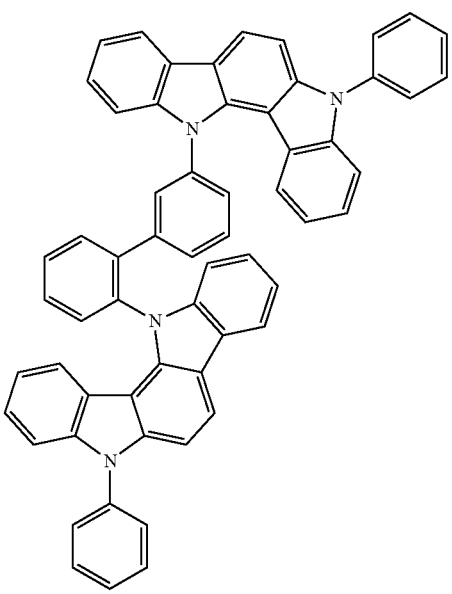
28

29
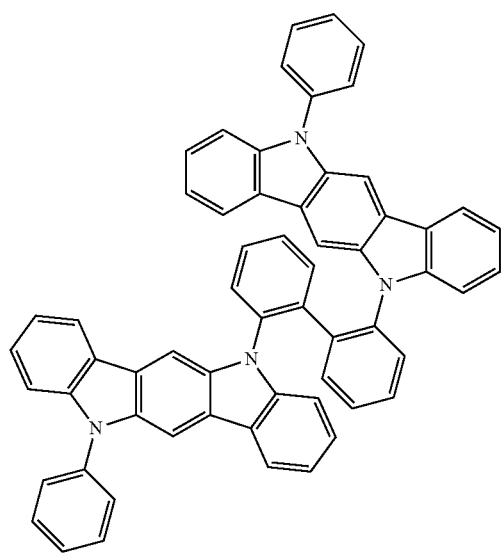
30
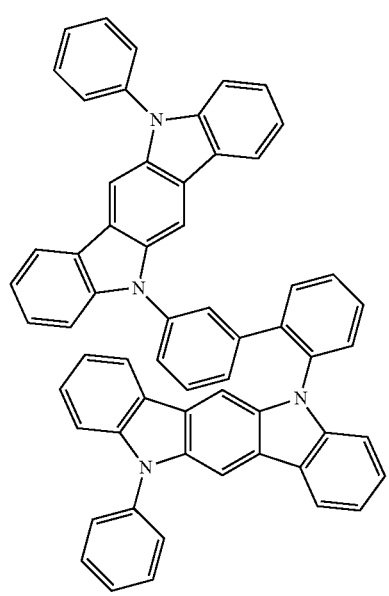
31
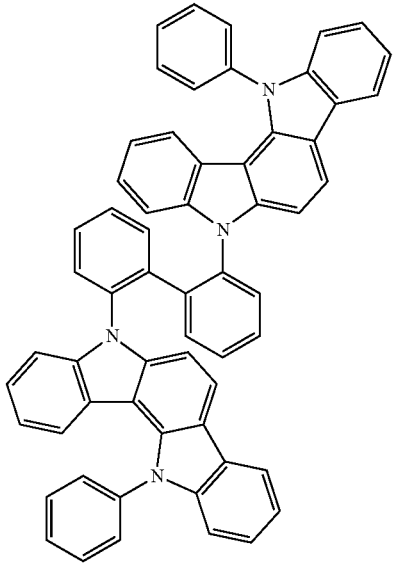
32
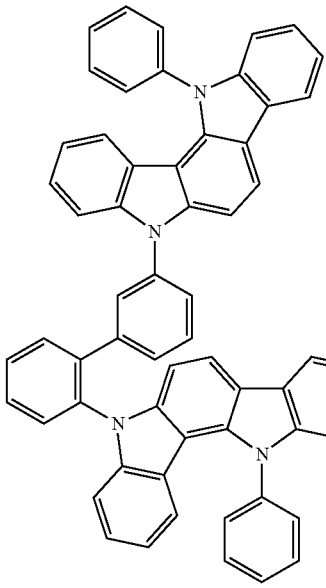
33
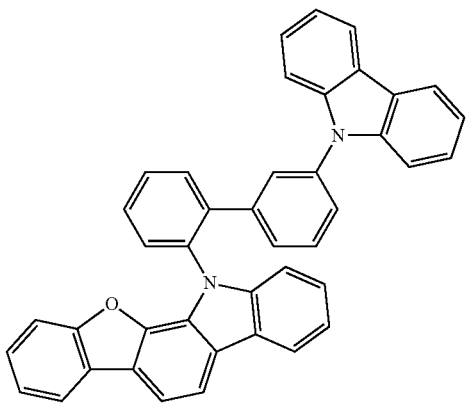

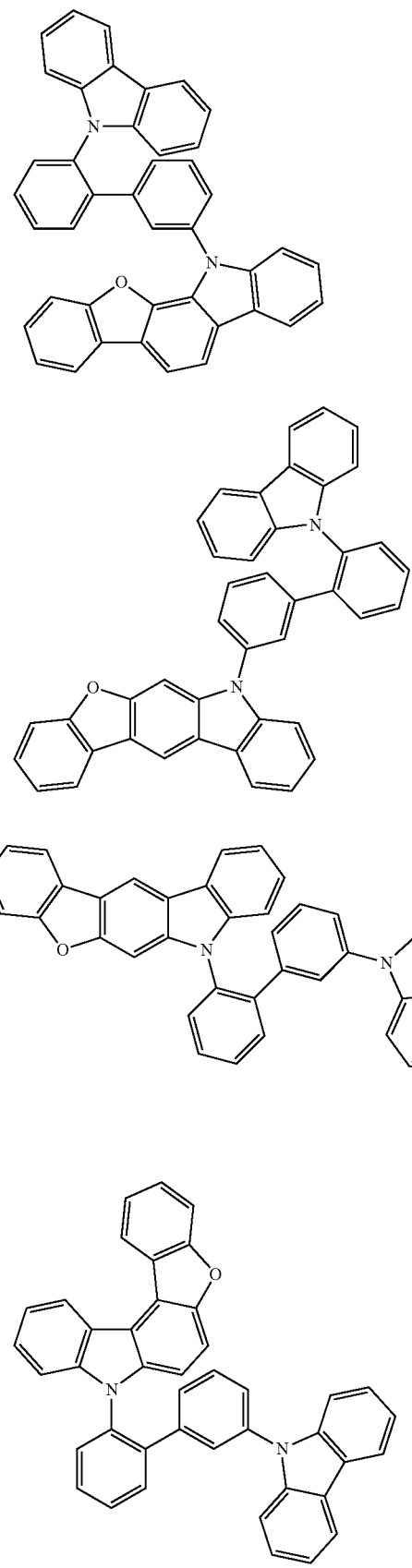
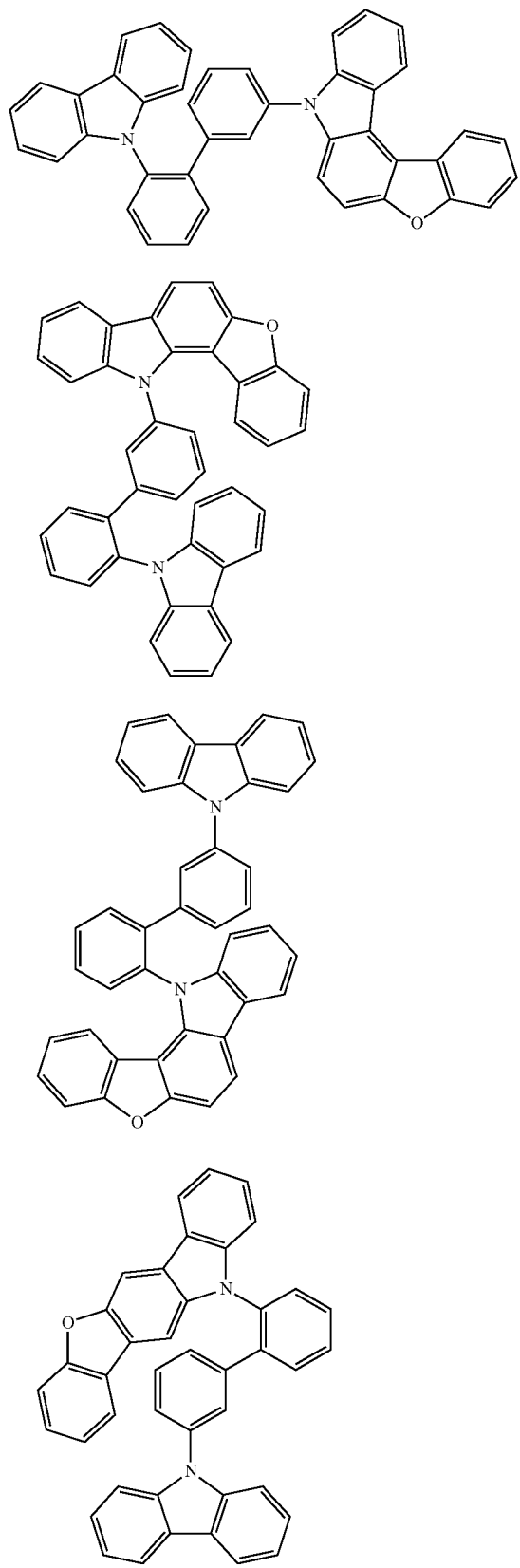

42
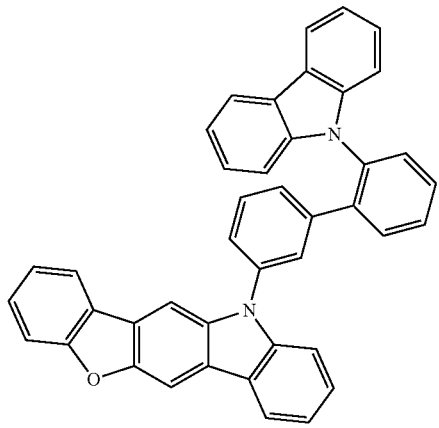
43
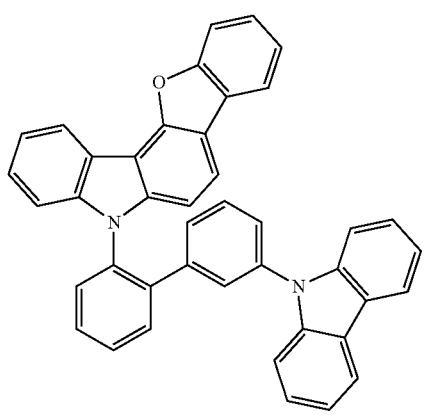
44
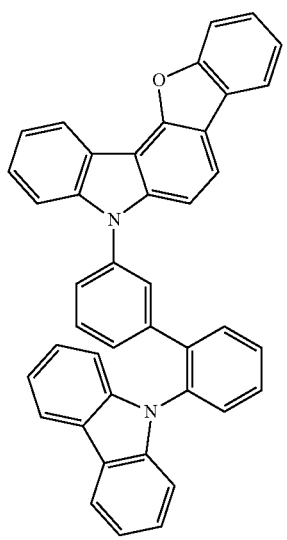
45
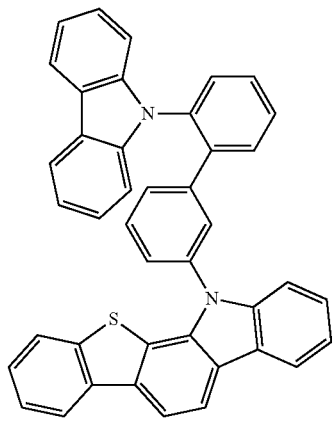
46
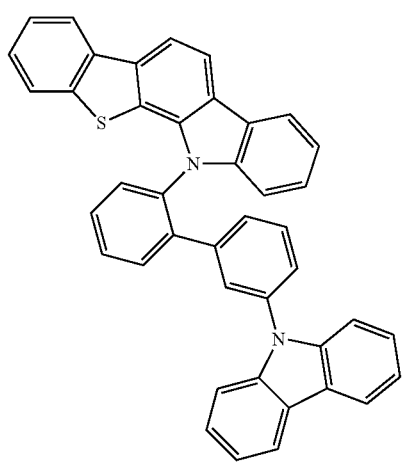
47
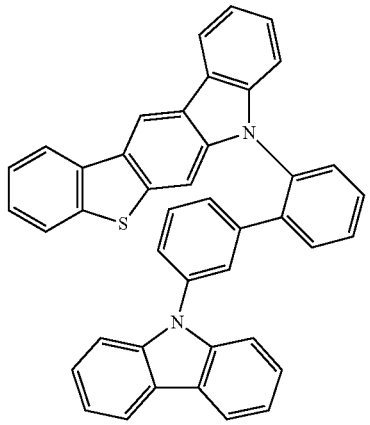

48
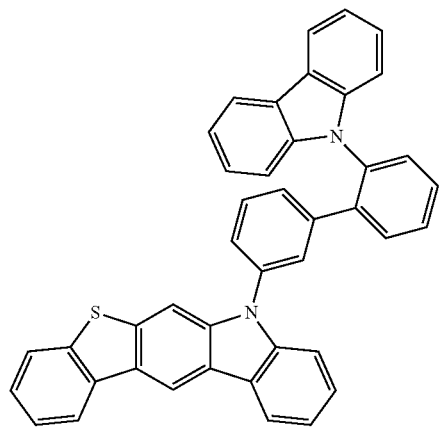
49
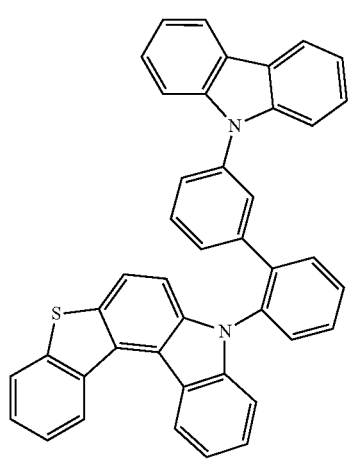
50
51
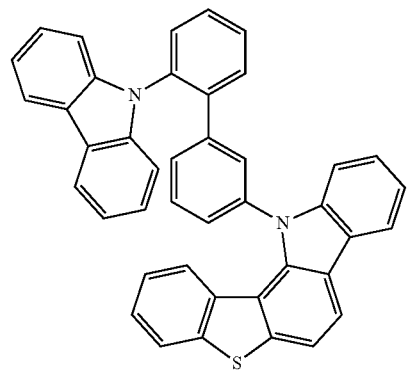
52
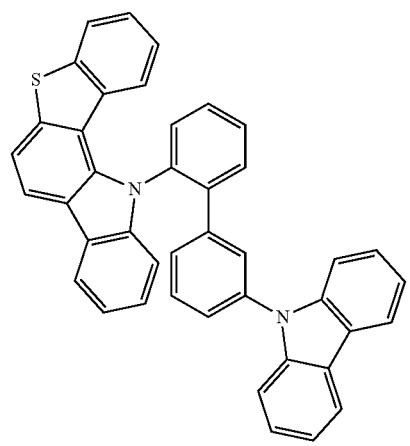
53
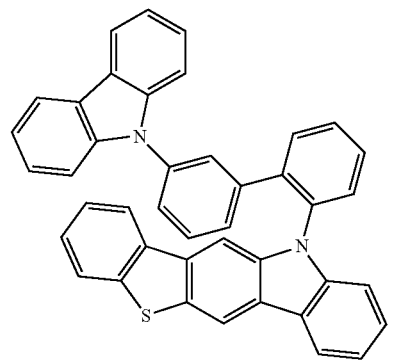
54
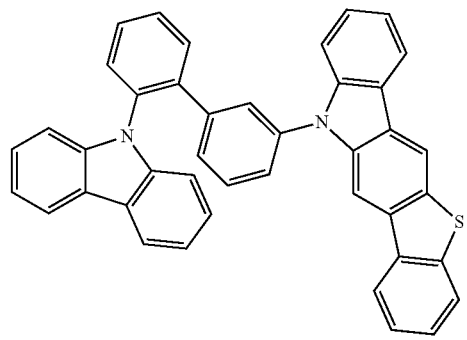

55
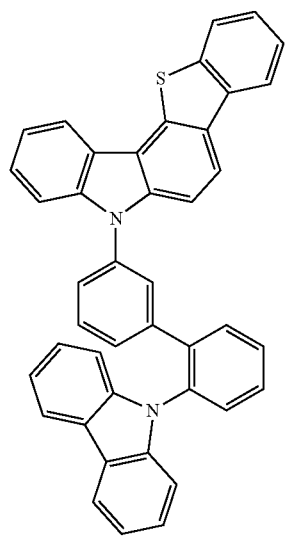
56
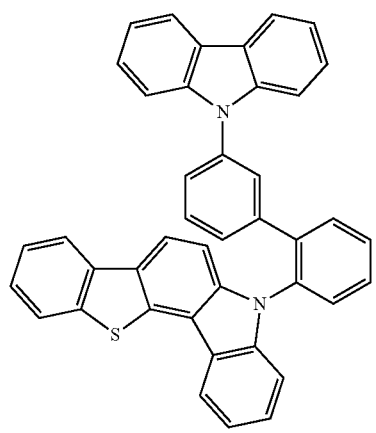
57
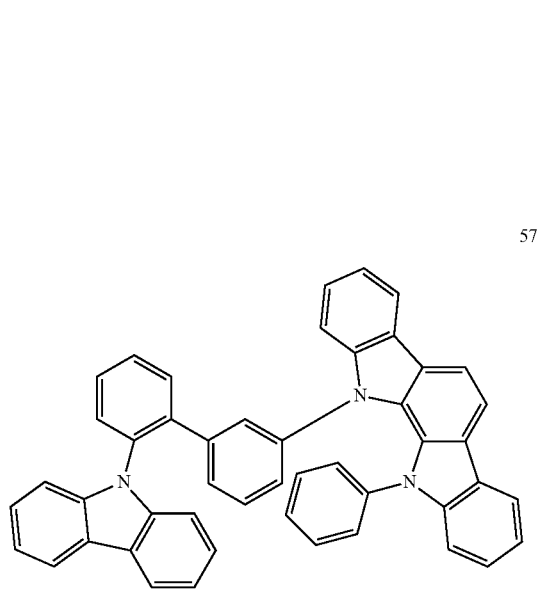
58
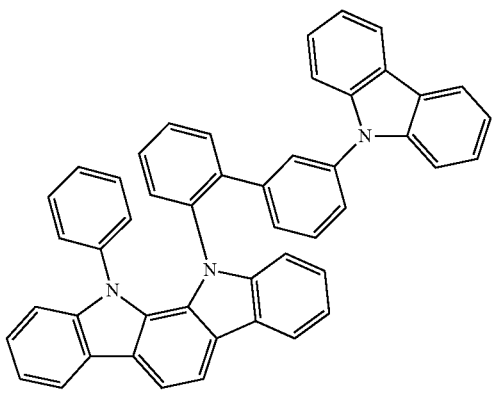
59
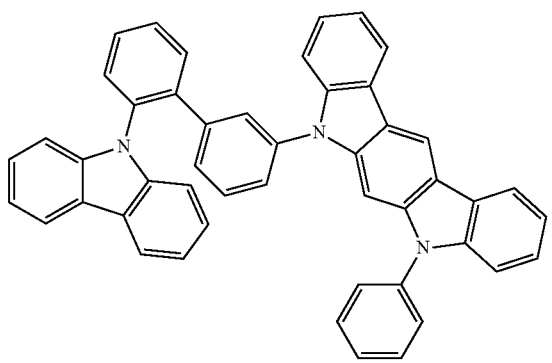
60
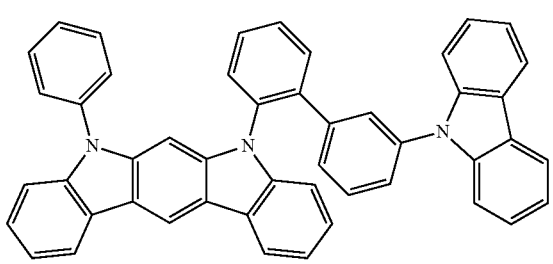
61
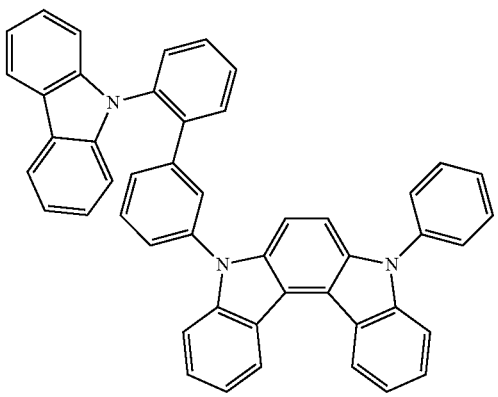

62
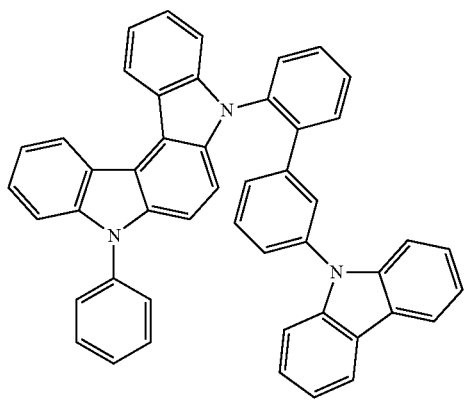
65
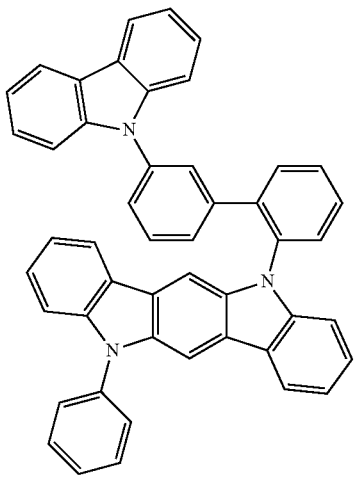
63
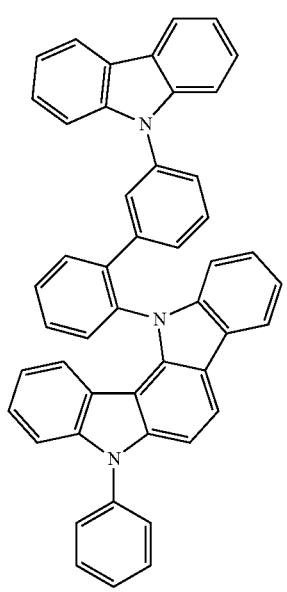
66
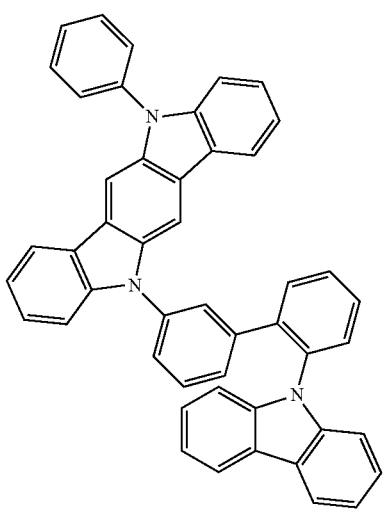
64
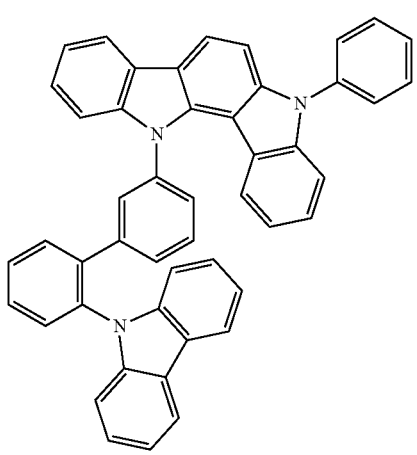
67
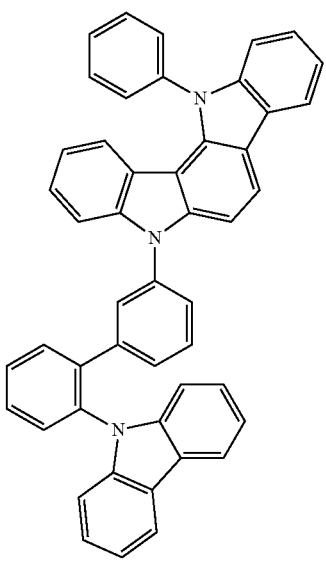

68
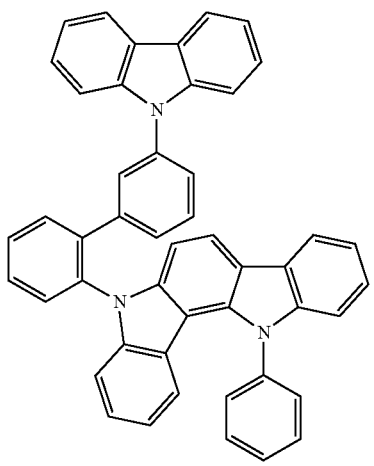
69
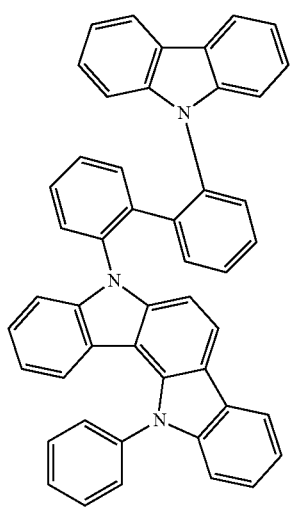
70
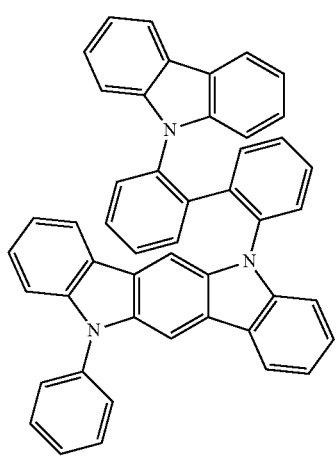
71
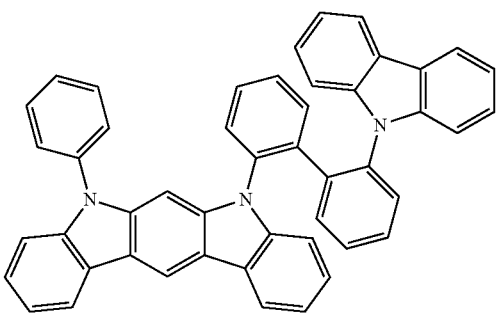
72
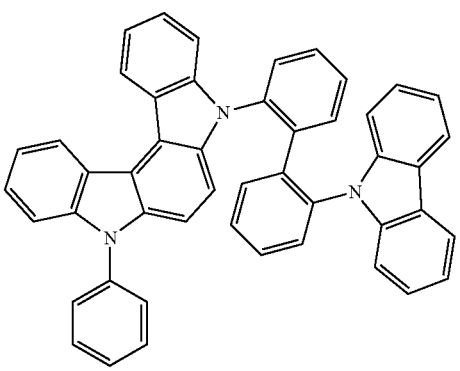
73
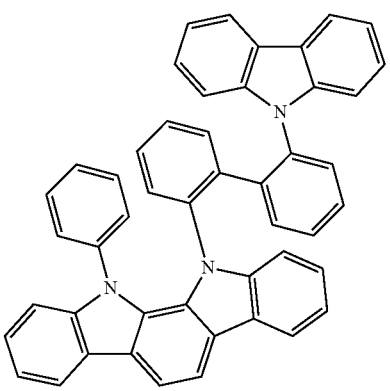
74
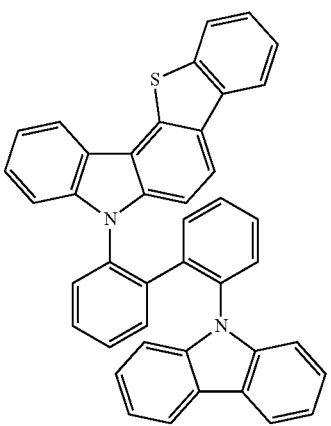

75
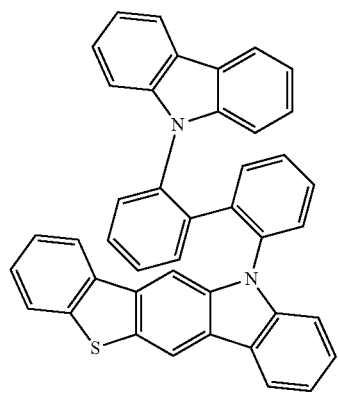
76
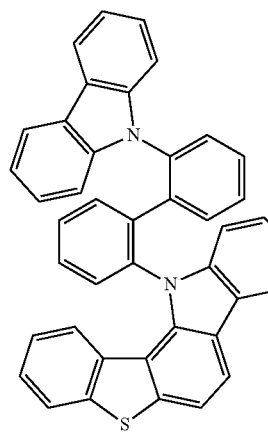
77
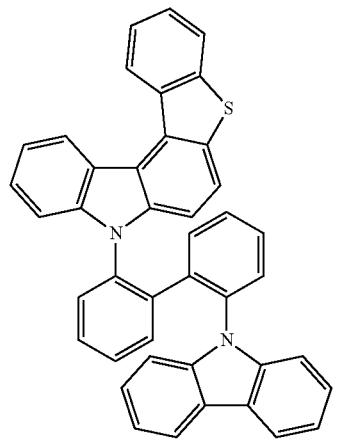
78
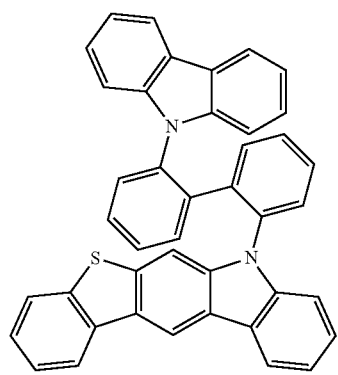
79
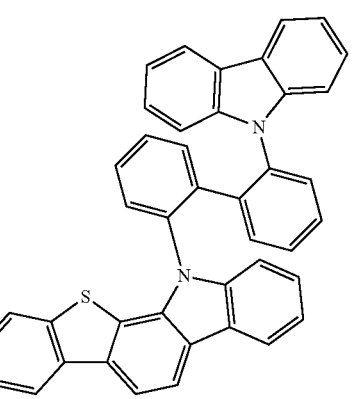
80
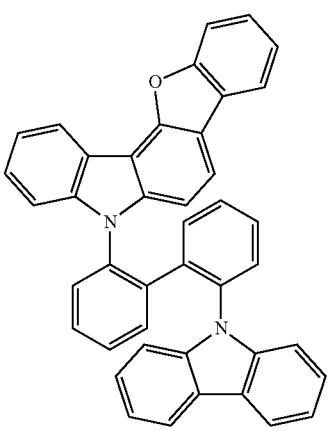
81
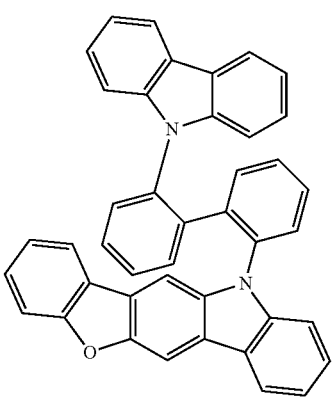
82
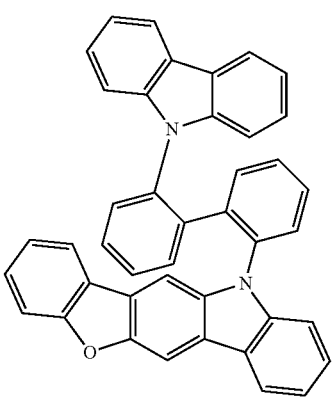

83
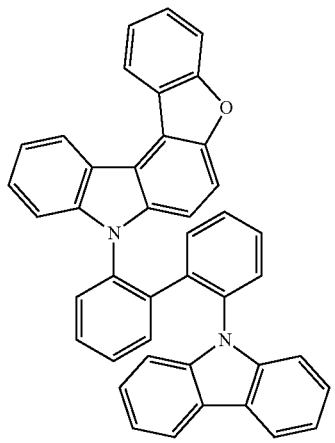
84
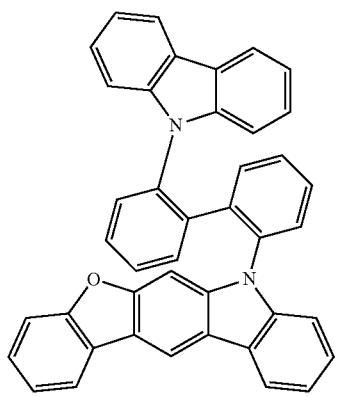
85
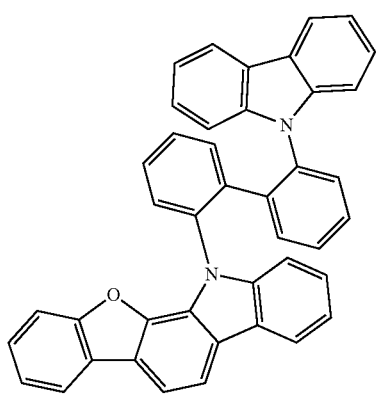
86
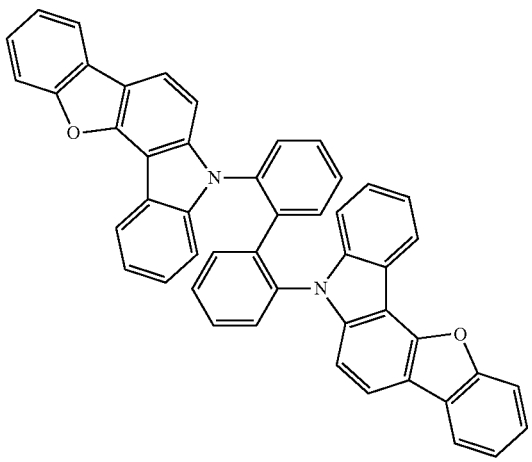
87
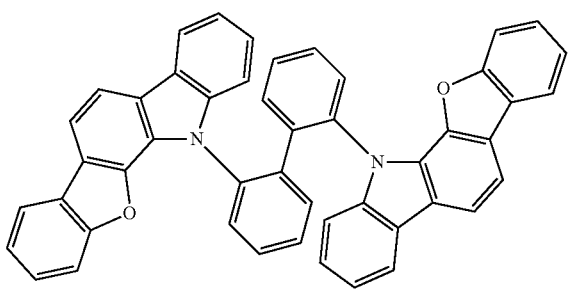
88
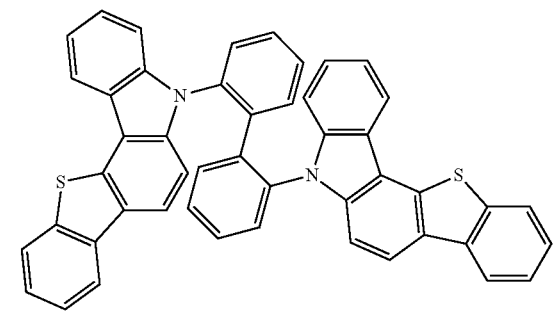
89
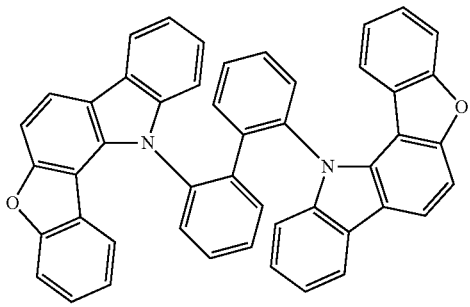

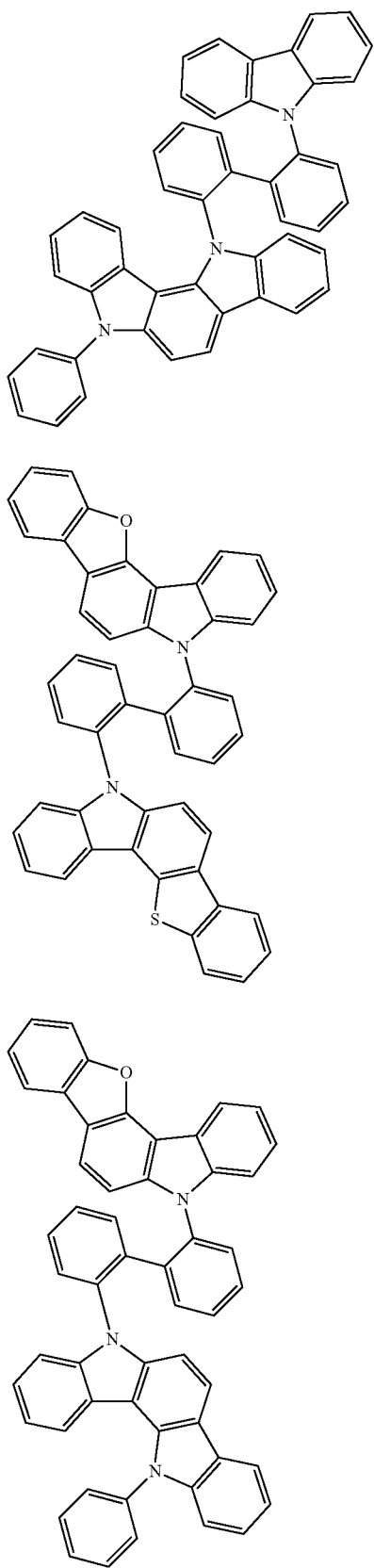
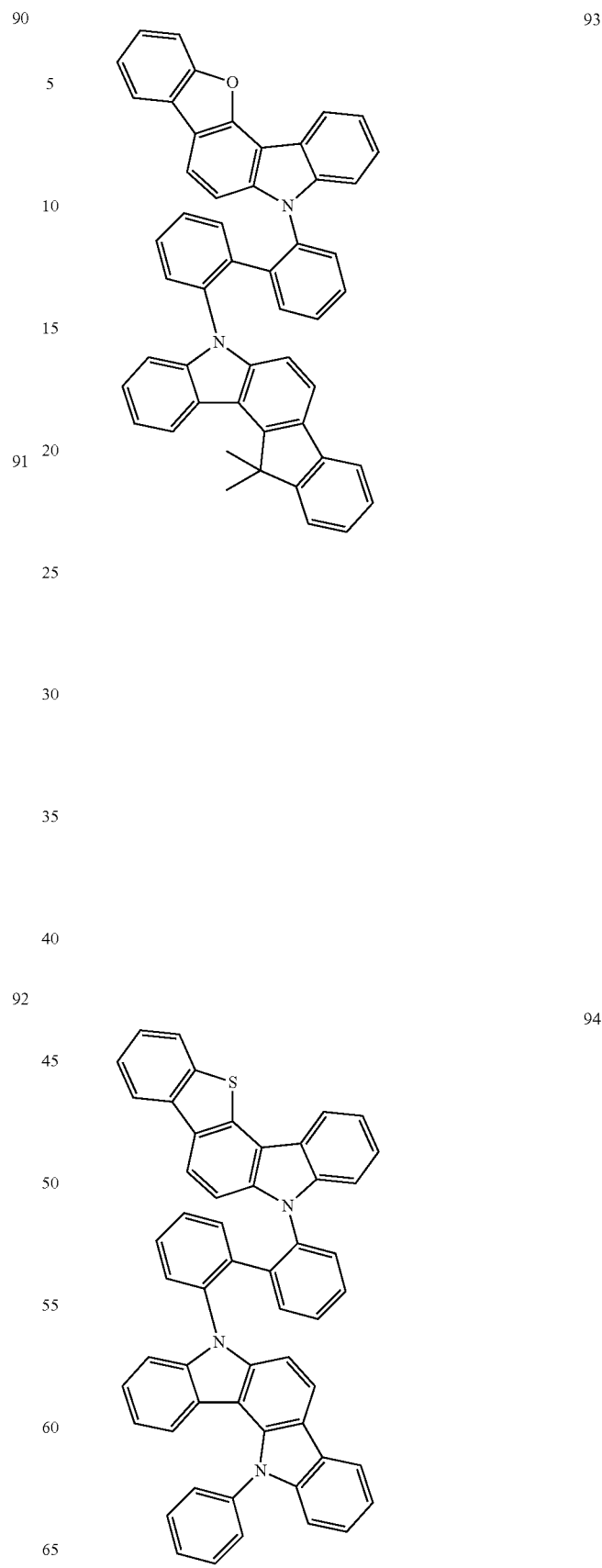

95
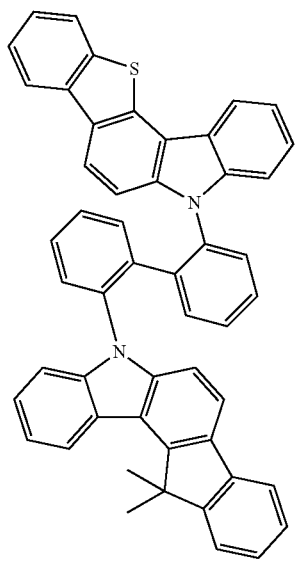
96
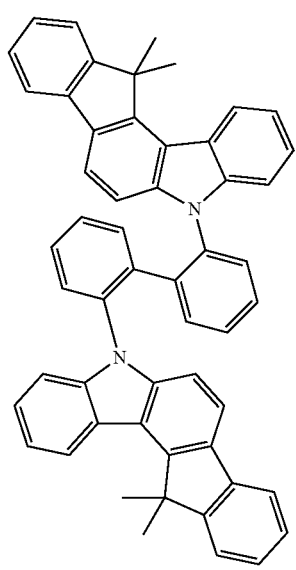
97
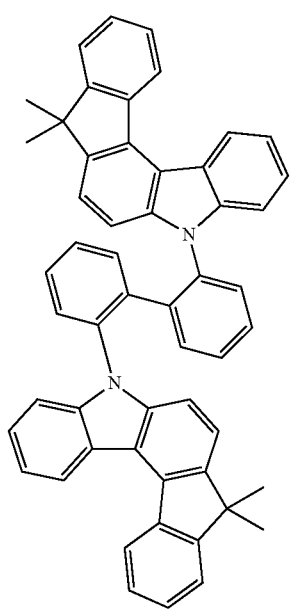
98
99
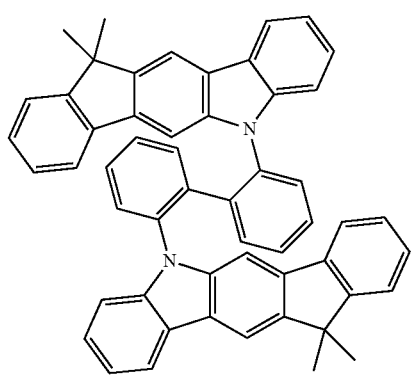

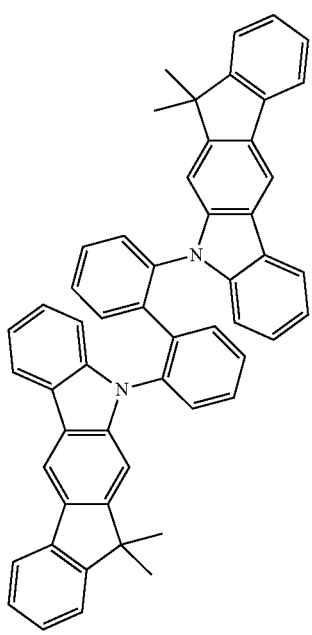
100
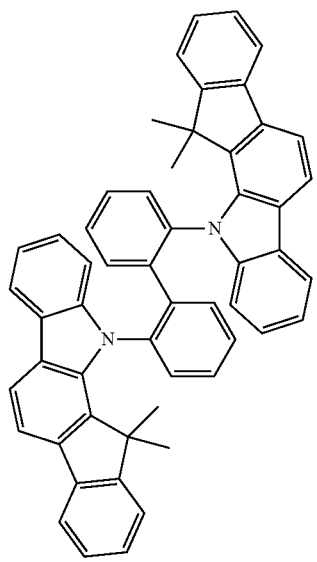
102
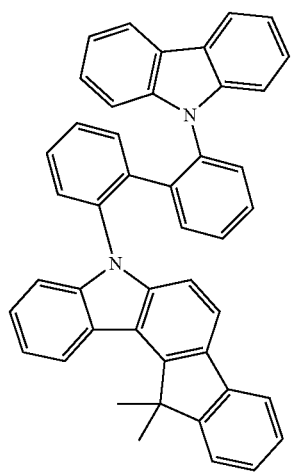
103
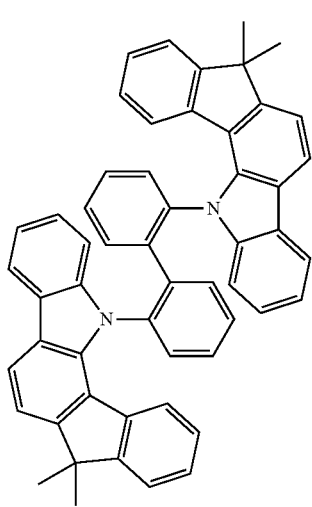
101
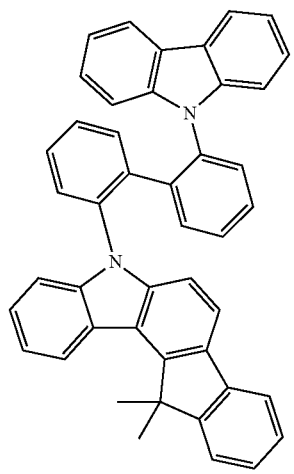
104

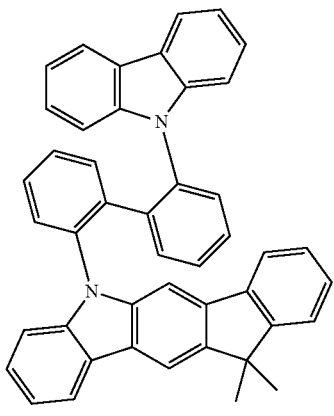

105

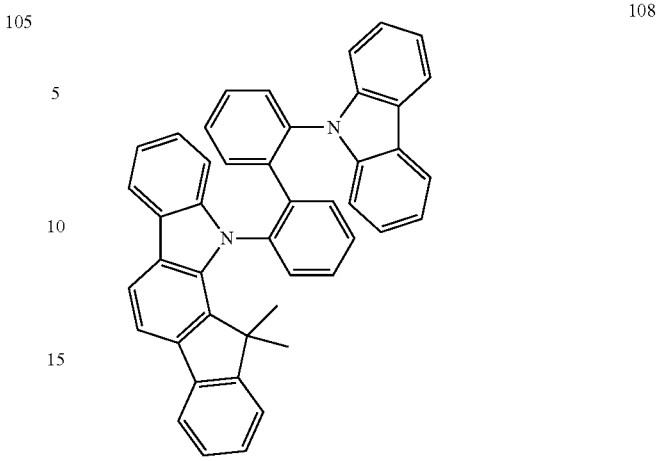

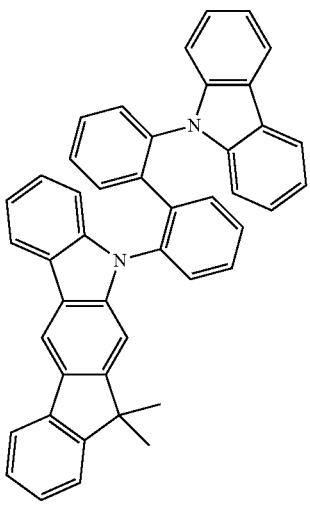

106

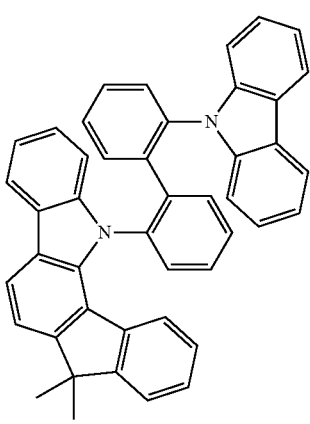

107

108

At least one of $L_1$ and $L_2$ in Formula 1 may be selected from groups represented by Formula 4. In this regard, the condensed cyclic compound represented by Formula 1 may have steric hindrance, and thus have a high triplet energy value and excellent charge transfer characteristics. As a result, an electronic device including the condensed cyclic compound represented by Formula 1, for example, an organic light-emitting device, may have high efficiency and high luminance.

In some embodiments, in Formula 1, $Ar_1$ may be a group represented by Formula 2 and $Ar_2$ may be a group represented by Formula 3, and thus the condensed cyclic compound represented by Formula 1 may have excellent thermal stability. As a result, an electronic device including the condensed cyclic compound represented by Formula 1, for example, an organic light-emitting device, may have long lifespan.

$R_1$ to $R_4$, $R_{10}$, $R_{20}$ and $R_{30}$ in Formula 1 may be selected from a hydrogen, a deuterium, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{10}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{10}$ aryl group, a substituted or unsubstituted $C_6$-$C_{10}$ aryloxy group, a substituted or unsubstituted $C_6$-$C_{10}$ arylthio group, a substituted or unsubstituted $C_7$-$C_{10}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{10}$ heteroarylthio group, a substituted or unsubstituted $C_3$-$C_{10}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), and $R_{40}$ and $R_{50}$ may be selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{10}$ aryl group, a substituted or unsubstituted $C_6$-$C_{60}$ aryloxy group, a substituted or unsubstituted $C_6$-$C_{10}$ arylthio group, a substituted or unsubstituted $C_7$-$C_{10}$ arylalkyl group, a substituted or unsubstituted $C_1$-$C_{10}$ heteroaryl group, a substituted or unsubstituted $C_2$-$C_{10}$ heteroaryloxy group, a substituted or unsubstituted $C_2$-$C_{10}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$).

$R_1$ to $R_4$, $R_{10}$, $R_{20}$, $R_{30}$, $R_{40}$ and $R_{50}$ do not include "a halogen group including a fluoro group (—F)", and thus the condensed cyclic compound represented by Formula 1 may have excellent heat resistance and thermal stability. Thus, when a thin film including the condensed cyclic compound represented by Formula 1 is formed through a deposition process, the condensed cyclic compound represented by Formula 1 may not decompose at a deposition temperature of a deposition process. As a result, an electronic device including the condensed cyclic compound represented by Formula 1, for example, an organic light-emitting device, may have long lifespan. In some embodiments, since $R_1$ to $R_4$, $R_{10}$, $R_{20}$, $R_{30}$, $R_{40}$ and $R_{50}$ may not include "a fluoro group (—F)", "$Ar_1$ and $Ar_2$" in Formula 1 may have an orbital contributing HOMO energy level, and "$L_1$ and $L_2$" in Formula 1 may have an orbital contributing to LUMO energy level, and thus the orbital contributing to HOMO energy level and the orbital contributing to LUMO energy level may be separated and respectively distributed in moieties having different structures. As a result, the condensed cyclic compound represented by Formula 1 may have excellent charge transfer characteristics, and an electronic device including the condensed cyclic compound represented by Formula 1, for example, an organic light-emitting device, may present high efficiency.

For example, from the molecular orbital distribution of Compound 23 evaluated by using a Density Functional Theory (DFT) method including a Gaussian program structurally optimized at B3LYP/6-31G(d,p), it was found that $B_1$ and $B_3$ (an indolocarbazole ring) have an orbital contributing to HOMO energy level, and $B_2$ (a biphenylene group) has an orbital contributing to LUMO energy level. Thus the orbital contributing to HOMO energy level and the orbital contributing to LUMO energy level in a molecule of Compound 23 may be separated and respectively distributed in moieties having different structures.

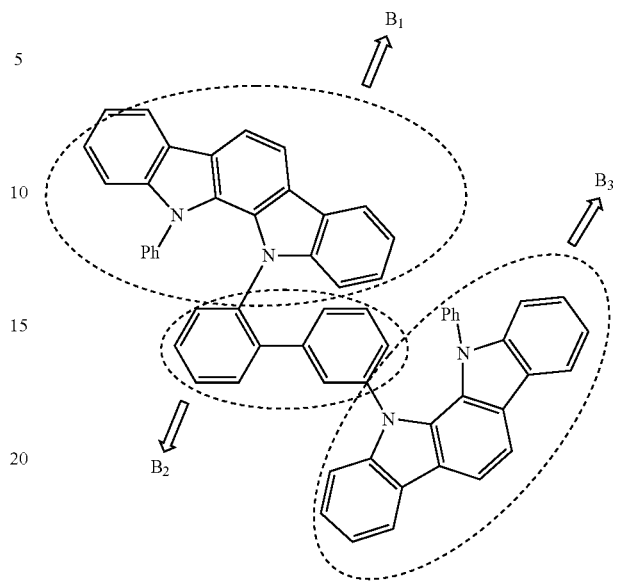

Compound 23

For comparison, from the molecular orbital distribution of Compound A evaluated by using a DFT method including a Gaussian program structurally optimized at B3LYP/6-31G (d,p), it was found that $A_1$ (an indolocarbazole ring substituted with —F) may have an orbital contributing to HOMO energy level and $A_2$ (an indolocarbazole ring substituted with —F) may have an orbital contributing to LUMO energy level. Thus, the orbital contributing to HOMO energy level and the orbital contributing to LUMO energy level may be separated and respectively distributed in moieties having the same structures. Compound A having the aforementioned orbital distribution may have poor charge transfer characteristics, and thus an electronic device, including Compound A, for example, an organic light-emitting device, may have low luminescent efficiency.

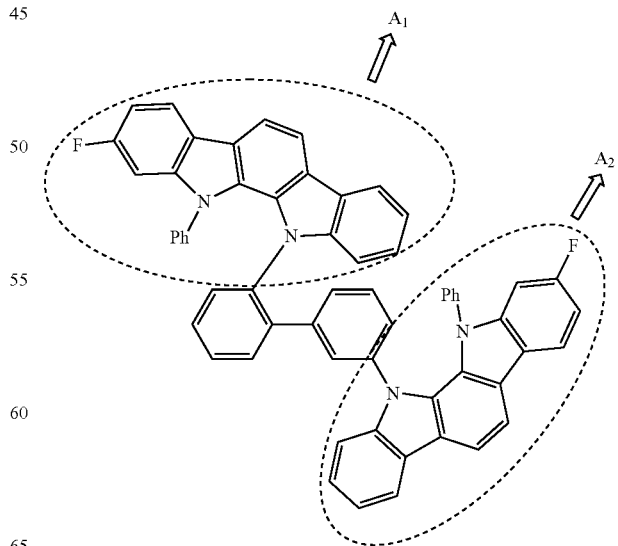

Compound A

Ph in Compound A denotes a phenyl group.

Each of $R_1$ to $R_4$, $R_{10}$, $R_{20}$, $R_{30}$, $R_{40}$ and $R_{50}$ may not have "a halogen atom" having high electron affinity, and thus the condensed cyclic compound represented by Formula 1 may have excellent hole transportation capability. As a result, an electronic device including the condensed cyclic compound represented by Formula 1, for example, an organic light-emitting device, may present high efficiency.

For example, HOMO, LUMO, and $T_1$ energy levels of Compounds 1 to 90 were evaluated through a simulation using a DFT method including a Gaussian program structurally optimized at B3LYP/6-31G(d,p). The results thereof are shown in Table 1 below:

TABLE 1

| Compound No. | $T_1$ (eV) | HOMO (eV) | LUMO (eV) |
| --- | --- | --- | --- |
| 1 | 2.957 | −5.27 | −0.972 |
| 2 | 2.924 | −5.285 | −1.146 |
| 3 | 2.907 | −5.188 | −1.12 |
| 4 | 2.835 | −5.328 | −1.254 |
| 5 | 2.832 | −5.183 | −1.157 |
| 6 | 2.984 | −5.255 | −1.191 |
| 7 | 2.771 | −5.348 | −1.281 |
| 8 | 2.78 | −5.204 | −1.211 |
| 9 | 3.005 | −5.162 | −1.142 |
| 10 | 2.892 | −5.249 | −1.137 |
| 11 | 2.9 | −5.175 | −1.126 |
| 12 | 2.87 | −5.292 | −1.196 |
| 13 | 2.862 | −5.196 | −1.148 |
| 14 | 2.802 | −5.286 | −1.299 |
| 15 | 2.913 | −5.434 | −1.324 |
| 16 | 2.801 | −5.133 | −1.199 |
| 17 | 2.757 | −5.276 | −1.298 |
| 18 | 2.919 | −5.26 | −1.154 |
| 19 | 2.762 | −5.093 | −1.272 |
| 20 | 2.97 | −5.214 | −1.16 |
| 21 | 2.908 | −5.099 | −1.043 |
| 22 | 2.824 | −5.012 | −1.199 |
| 23 | 2.906 | −5.047 | −0.972 |
| 24 | 2.824 | −4.894 | −1.016 |
| 25 | 2.734 | −4.904 | −1.019 |
| 27 | 2.967 | −4.975 | −1.038 |
| 28 | 2.957 | −4.885 | −1.019 |
| 29 | 2.679 | −4.86 | −1.057 |
| 30 | 2.668 | −4.802 | −1.032 |
| 31 | 2.966 | −5.035 | −1.024 |
| 32 | 2.958 | −4.952 | −1.06 |
| 33 | 2.96 | −5.249 | −1.015 |
| 34 | 2.961 | −5.278 | −0.996 |
| 35 | 2.906 | −5.168 | −1.083 |
| 36 | 2.923 | −5.25 | −1.093 |
| 37 | 2.84 | −5.251 | −1.135 |
| 38 | 2.83 | −5.181 | −1.107 |
| 39 | 2.982 | −5.238 | −1.202 |
| 40 | 2.984 | −5.255 | −1.143 |
| 41 | 2.78 | −5.266 | −1.189 |
| 42 | 2.781 | −5.175 | −1.112 |
| 43 | 3.013 | −5.236 | −1.084 |
| 44 | 3.006 | −5.161 | −1.084 |
| 45 | 2.908 | −5.174 | −1.08 |
| 46 | 2.899 | −5.236 | −1.067 |
| 47 | 2.873 | −5.252 | −1.107 |
| 48 | 2.86 | −5.17 | −1.094 |
| 49 | 2.808 | −5.207 | −1.176 |
| 50 | 2.799 | −5.141 | −1.126 |
| 51 | 2.919 | −5.257 | −1.101 |
| 52 | 2.925 | −5.268 | −1.176 |
| 53 | 2.762 | −5.2 | −1.206 |
| 54 | 2.761 | −5.094 | −1.125 |
| 55 | 2.972 | −5.207 | −1.107 |
| 56 | 2.975 | −5.268 | −1.092 |
| 57 | 2.923 | −5.006 | −0.955 |
| 58 | 2.909 | −5.164 | −1.108 |
| 59 | 2.824 | −4.919 | −1.042 |
| 60 | 2.833 | −4.977 | −4.015 |
| 61 | 2.744 | −4.821 | −1.03 |

TABLE 1-continued

| Compound No. | $T_1$ (eV) | HOMO (eV) | LUMO (eV) |
| --- | --- | --- | --- |
| 62 | 2.735 | −4.848 | −1.03 |
| 63 | 2.974 | −4.965 | −1.042 |
| 64 | 2.962 | −4.92 | −1.017 |
| 65 | 2.683 | −4.846 | −1.07 |
| 66 | 2.678 | −4.789 | −1.001 |
| 67 | 2.966 | −4.926 | −1.028 |
| 68 | 2.961 | −4.976 | −1.069 |
| 69 | 2.967 | −5.07 | −1.041 |
| 70 | 2.688 | −4.904 | −1.06 |
| 71 | 2.835 | −5.059 | −1.06 |
| 72 | 2.732 | −4.944 | −1.035 |
| 73 | 2.913 | −5.13 | −1.155 |
| 74 | 2.97 | −5.354 | −1.127 |
| 75 | 2.757 | −5.267 | −1.275 |
| 76 | 2.93 | −5.357 | −1.195 |
| 77 | 2.806 | −5.286 | −1.264 |
| 78 | 2.875 | −5.312 | −1.106 |
| 80 | 3.008 | −5.307 | −1.112 |
| 81 | 2.772 | −5.343 | −1.261 |
| 82 | 2.984 | −5.383 | −1.151 |
| 83 | 2.838 | −5.319 | −1.194 |
| 84 | 2.925 | −5.32 | −1.114 |
| 85 | 5.953 | −5.355 | −1.11 |
| 86 | 3.006 | −5.308 | −1.153 |
| 87 | 2.952 | −5.351 | −1.091 |
| 88 | 2.97 | −5.363 | −1.18 |
| 89 | 2.984 | −5.393 | −1.244 |
| 90 | 2.969 | −5.029 | −1.04 |

Table 1 shows that Compounds 1 to 90 have excellent electric characteristics, for example, high $T_1$ energy level.

A method of synthesizing the condensed cyclic compound represented by Formula 1 may be understood by ordinary skill in the art by referring to Synthesis Examples.

In this regard, the condensed cyclic compound represented by Formula 1 may be suitable as a material of an organic layer of an organic light-emitting device, for example, a material for a hole transport layer, a material for an electron blocking layer and/or a host of an emission layer. According to another aspect, provided is an organic light-emitting device that includes:

a first electrode;

a second electrode; and an organic layer disposed between the first electrode and the second electrode, wherein the organic layer includes an emission layer, and wherein the organic layer includes at least one of the condensed cyclic compounds represented by Formula 1.

While not wishing to be bound by theory, it is understood that when the organic light-emitting device includes the organic layer including the condensed cyclic compound represented by Formula 1 as described above, the organic light-emitting device has low driving voltage, high power efficiency, high luminous efficiency, high quantum luminance efficiency, and long lifespan.

For example, the condensed cyclic compound represented by Formula 1 may be included in the emission layer.

In some embodiments, the condensed cyclic compound represented by Formula 1 may be included in the emission layer, and the condensed cyclic compound represented by Formula 1 may be a material for delayed fluorescence.

According to an embodiment, the emission layer may include a host and a dopant (wherein an amount of the host is greater than an amount of the dopant), and the host may include the condensed cyclic compound represented by Formula 1. The condensed cyclic compound serving as a host may transfer energy to a dopant according to a delayed fluorescence emission mechanism. The dopant may include at least one of a fluorescent dopant and a phosphorescent dopant. The dopant may be selected from known dopants. The host may further include any suitable host selected from known hosts.

In some embodiments, the emission layer may include a host and a dopant (an amount of the host is greater than an amount of the dopant), and the dopant may include the condensed cyclic compound represented by Formula 1. The condensed cyclic compound as a dopant may emit delayed fluorescence according to a delayed fluorescence emission mechanism. The host may be selected from known dopants.

The emission layer may emit red, green or blue light.

According to an embodiment, the emission layer may be a blue emission layer including a phosphorescent dopant, but embodiments are not limited thereto.

In some embodiments, the condensed cyclic compound represented by Formula 1 may be included in a hole transport region.

For example, the hole transport region of the organic light-emitting device may include at least one of a hole transport layer and an electron blocking layer, and at least one of the hole transport layer and the electron blocking layer may include the condensed cyclic compound represented by Formula 1.

According to an embodiment, a hole transport region of the organic light-emitting device may include a hole transport layer, and the hole transport layer may include the condensed cyclic compound represented by Formula 1.

In some embodiments, a hole transport region of the organic light-emitting device may include an electron blocking layer, and the electron blocking layer may include the condensed cyclic compound represented by Formula 1. The electron blocking layer may directly contact the emission layer.

The expression as used herein "(an organic layer) includes at least one condensed cyclic compound" may be understood as "(organic layer) may include one condensed cyclic compound represented by Formula 1 or two or more different condensed cyclic compounds represented by Formula 1".

For example, the organic layer may include only Compound 1 as the condensed cyclic compound. In this regard, Compound 1 may be included in the emission layer of the organic light-emitting device. Alternatively, the organic layer may include Compound 1 and Compound 2 as the condensed cyclic compounds. In this regard, Compound 1 and Compound 2 may be included in the same layer (for example, both Compound 1 and Compound 2 may be included in the emission layer), or in different layers (for example, Compound 1 may be included in the emission layer and Compound 2 may be included in the electron blocking layer).

The first electrode may be an anode, which is a hole injection electrode, and the second electrode may be a cathode, which is an electron injection electrode.

Alternatively, the first electrode may be a cathode, which is an electron injection electrode, and the second electrode may be an anode, which is a hole injection electrode.

For example, in the organic light-emitting device,
the first electrode may be an anode,
the second electrode may be a cathode, and
the organic layer may include a hole transport region disposed between the first electrode and the emission layer,
wherein an electron transport region may be disposed between the emission layer and the second electrode,
the hole transport region may include at least one selected from a hole injection layer, a hole transport layer and an electron blocking layer, and the electron transport region may include at least one selected from a hole blocking layer, an electron transport layer and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment of the present disclosure. Hereinafter, a structure and a method of manufacturing an organic light-emitting device according to an embodiment of the present disclosure will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum-depositing or sputtering a material for forming the first electrode 11 on the substrate. The first electrode 11 may be an anode. The material for the first electrode 11 may be selected from materials with a high work function for easy hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag) may be used herein.

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer may be formed on the first electrode 11 by using various methods such as vacuum-deposition, spin coating, casting, and a Langmuir-Blodgett (LB) method.

When a hole injection layer is formed by vacuum-deposition, though the conditions may vary depending on a compound that is used as a hole injection material and a structure and thermal properties of a desired hole injection layer, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, but embodiments are not limited thereto.

When a hole injection layer is formed by spin coating, though the conditions may vary depending on a compound that is used as a hole injection material and a structure and thermal properties of a desired hole injection layer, the spin coating may be performed at a coating rate in a range of about 2,000 revolutions per minute (rpm) to about 5,000 rpm, and at a temperature in a range of about 80° C. to 200° C. for removing a solvent after the spin coating, but embodiments are not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, p-NPB, TPD, spiro-TPD, spiro-NPB, methylated-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

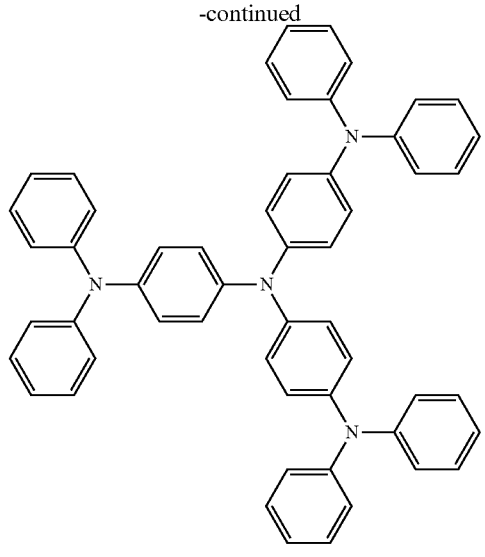

TDATA

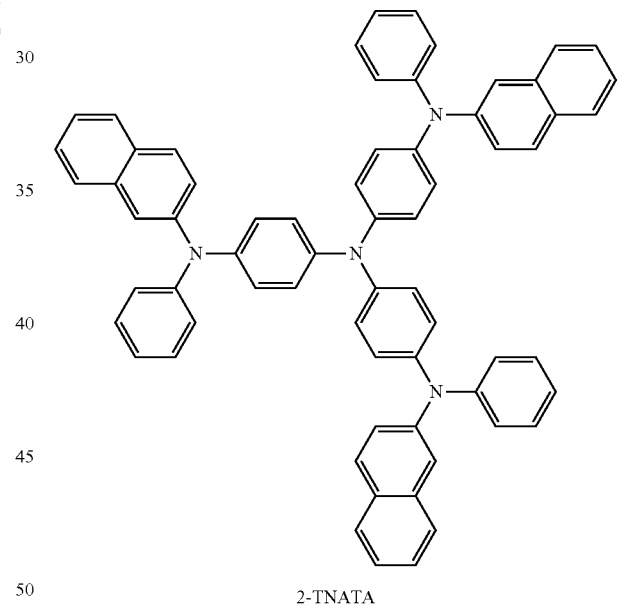

2-TNATA

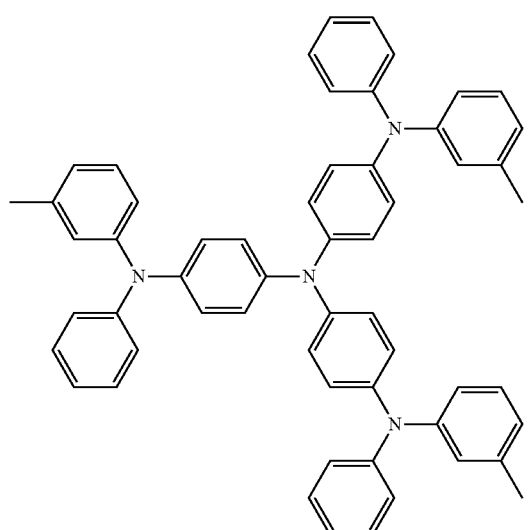

m-MTDATA

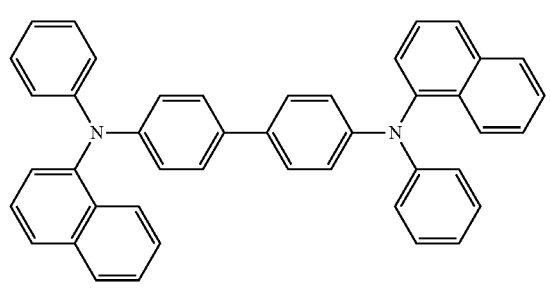

NPB

-continued

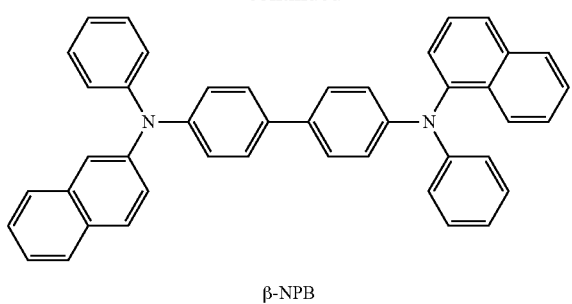

β-NPB

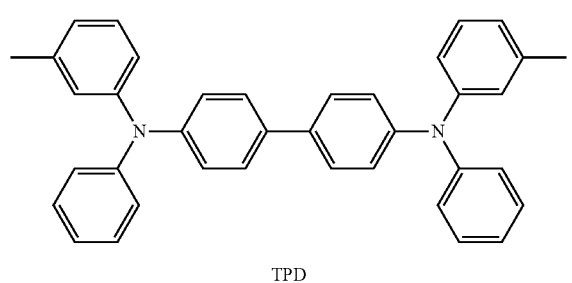

TPD

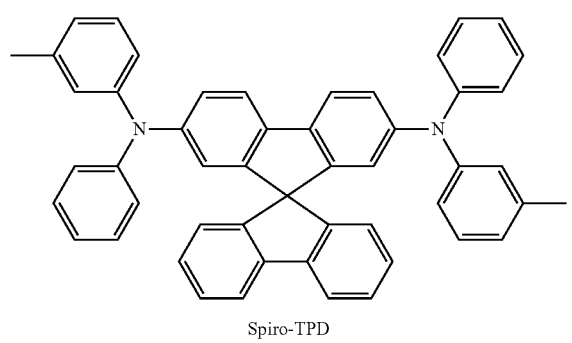

Spiro-TPD

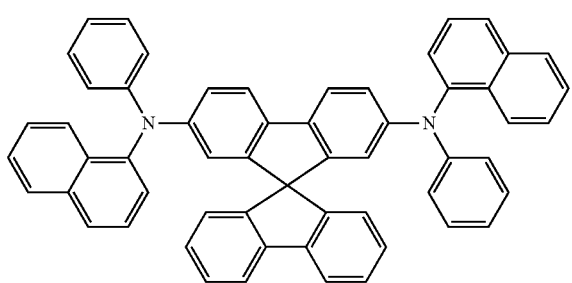

Spiro-NPB

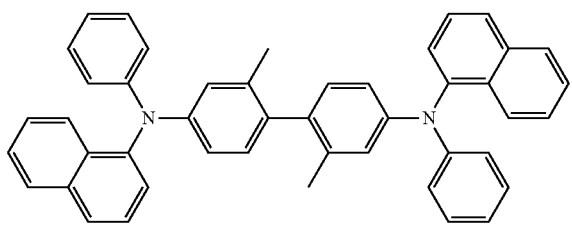

methylated NPB

-continued

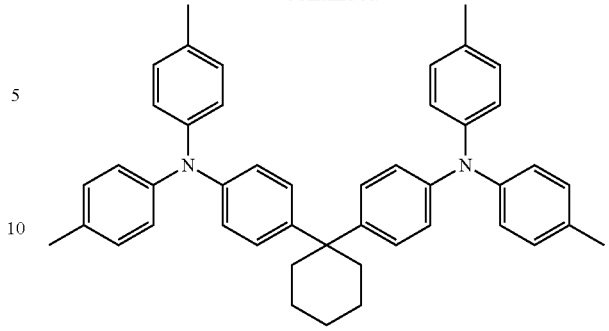

TAPC

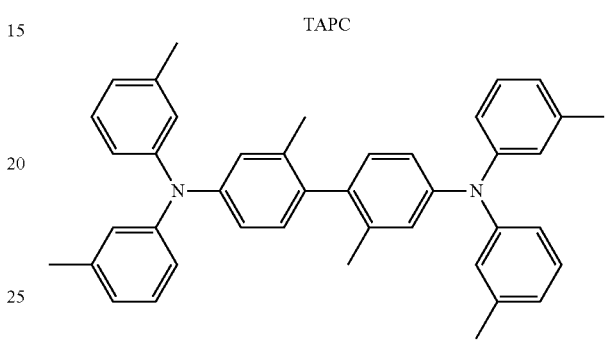

HMTPD

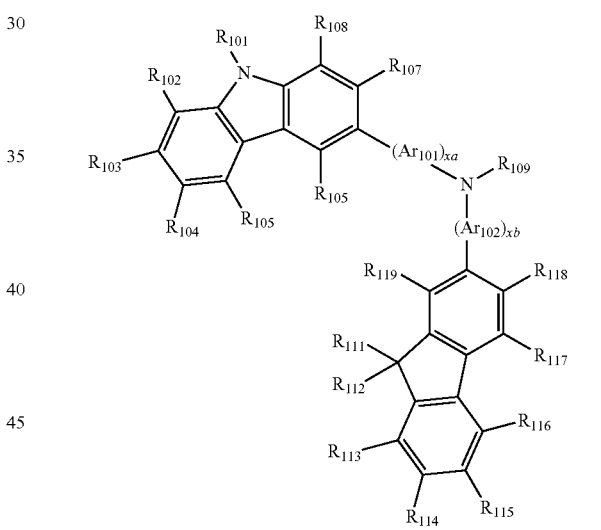

Formula 201

Formula 202

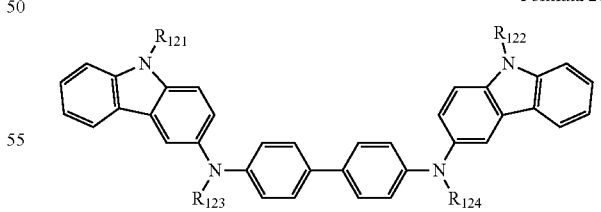

$Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{10}$ heteroarylalkyl group, a monovalent non-aromatic condensed polycyclic group and a monovalent non-aromatic condensed heteropolycyclic group.

xa and xb in Formula 201 may each independently be an integer of 0 to 5, or may be 0, 1 or 2. For example, xa may be 1 and xb may be 0, but embodiments are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, etc.) and a $C_1$-$C_{60}$ alkoxy group (for example, a methoxy group, an ethoxy group, a propoxy group, butoxy group, a pentoxy group, etc.);

a $C_1$-$C_{60}$ alkyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, an anthracenyl group, a fluorenyl group and a pyrenyl group; and a phenyl group, a naphthyl group, an anthracenyl group, a fluorenyl group and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but embodiments are not limited thereto.

$R_{109}$ in Formula 201 may be selected from a phenyl group, a naphthyl group, an anthracenyl group and a pyridinyl group; and a phenyl group, a naphthyl group, an anthracenyl group and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group and a pyridinyl group.

According to an embodiment, the compound represented by Formula 201 may be represented by Formula 201A, but embodiments are not limited thereto:

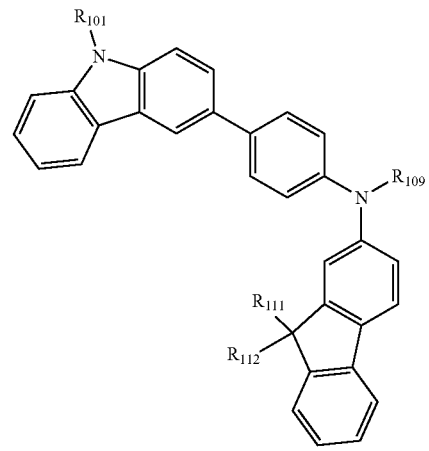

Formula 201A

Descriptions of $R_{101}$, $R_{111}$, $R_{112}$ and $R_{109}$ in Formula 201A are the same as provided herein.

For example, the compound represented by Formula 201 and the compound represented by Formula 202 may include Compounds HT1 to HT20, but embodiments are not limited thereto:

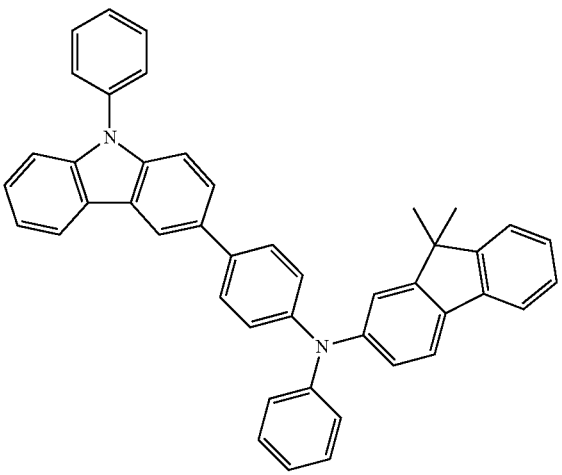

HT1

HT2
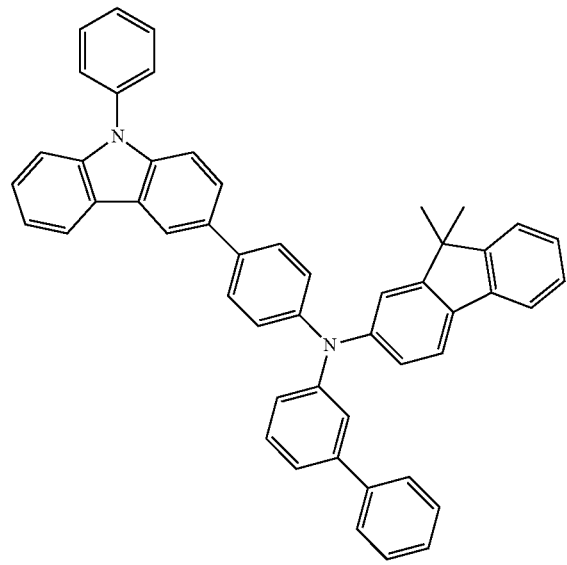
HT4
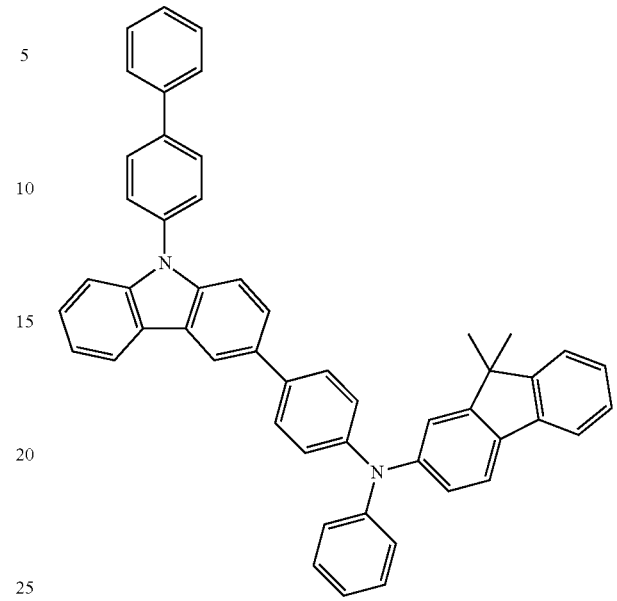
HT3
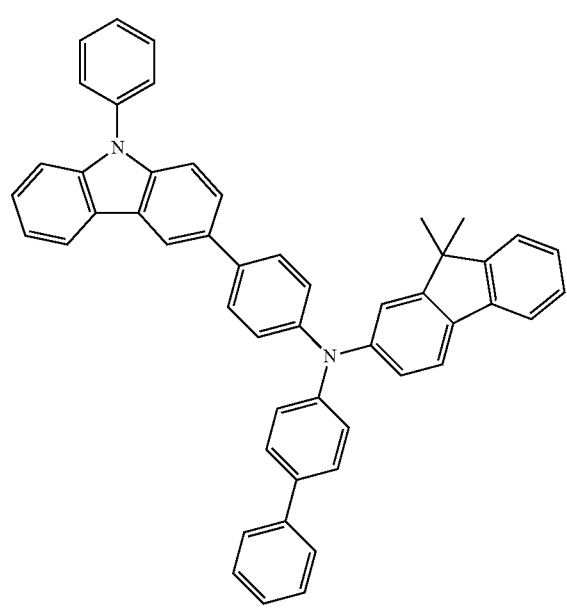
HT5
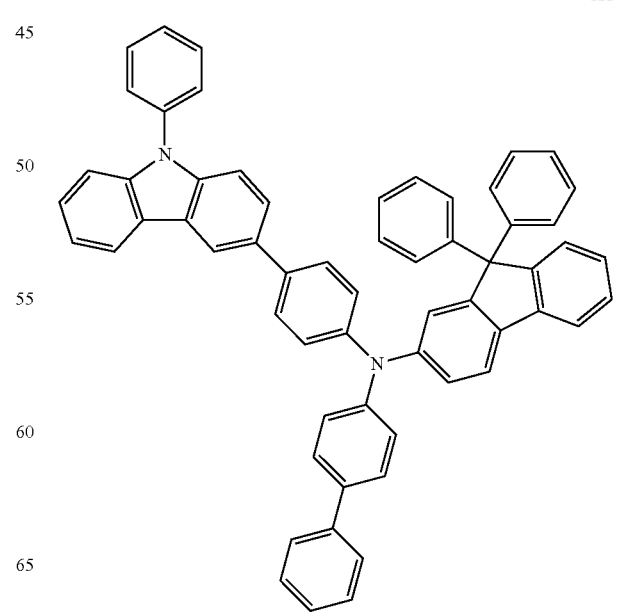

HT6
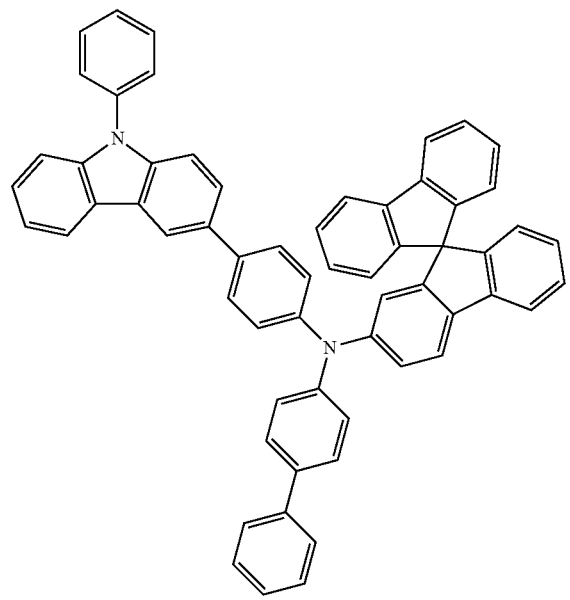
HT8
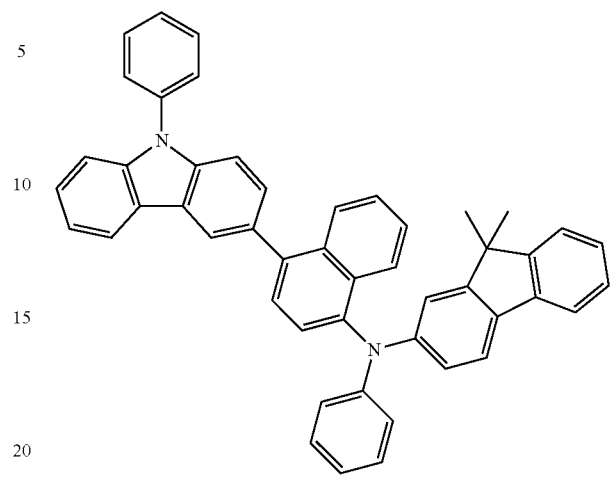
HT9
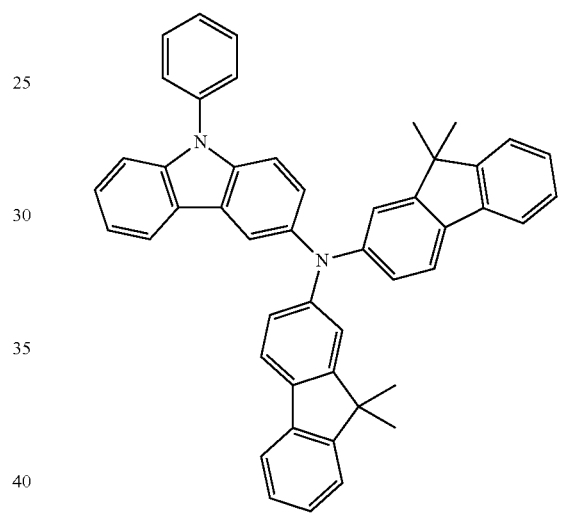
HT7
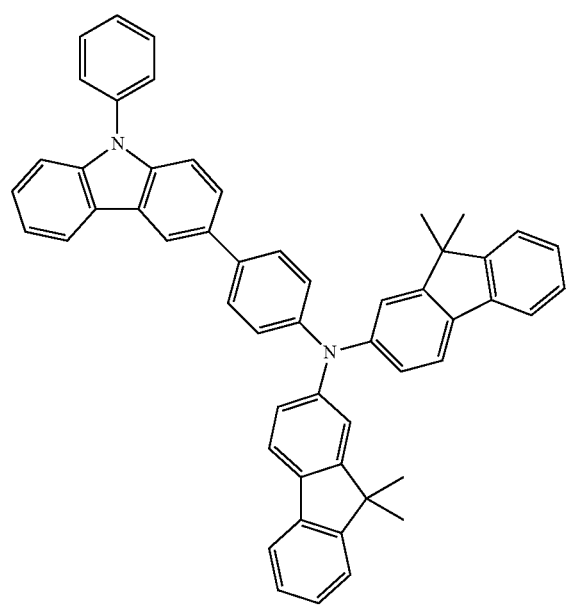
HT10
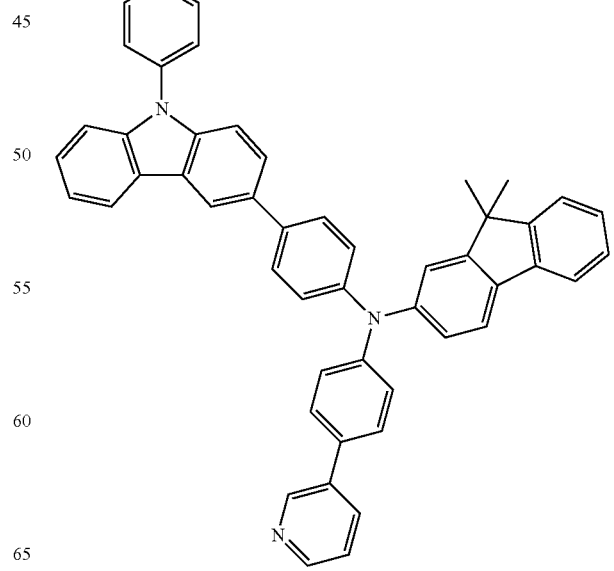

HT11
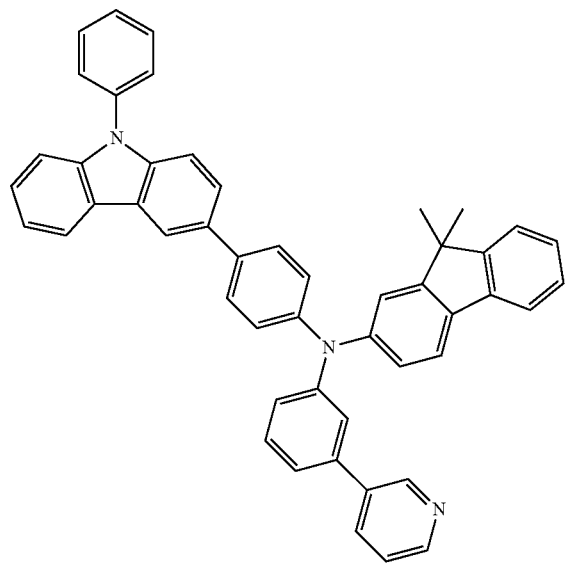
HT14
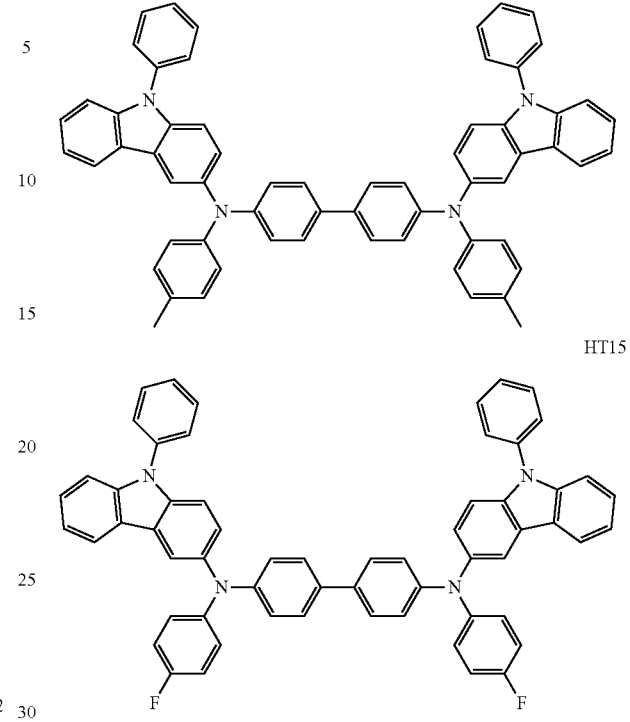
HT15
HT12
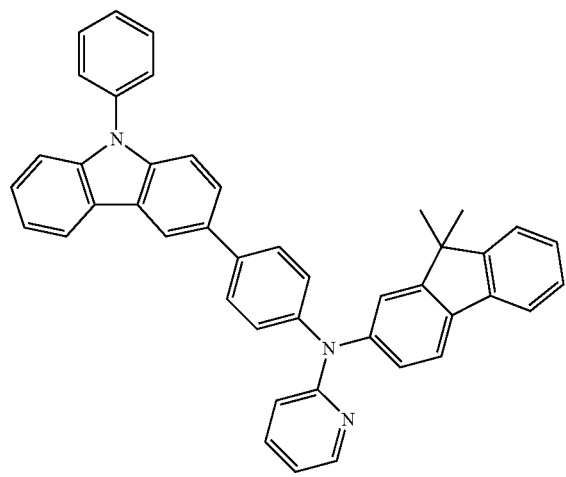
HT16
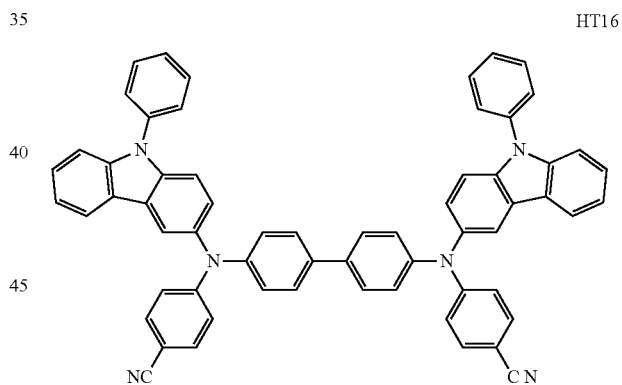
HT13
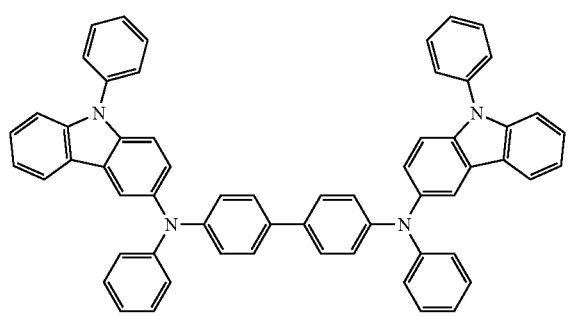
HT17
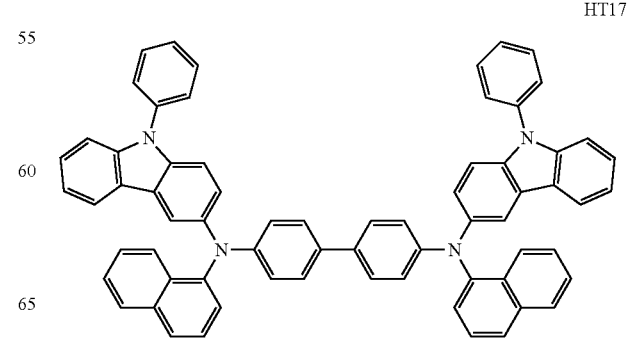

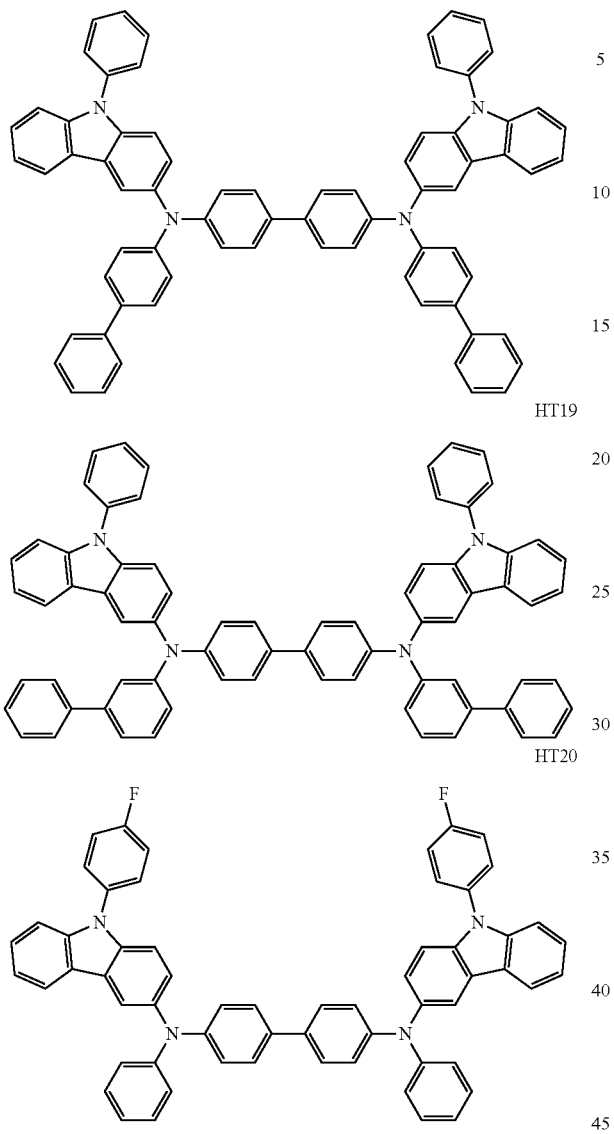

HT18

HT19

HT20

In some embodiments, the hole transport layer may include the condensed cyclic compound represented by Formula 1.

A thickness of the hole transport region may be in a range of about 100 Angstroms (Å) to about 10,000 Å, for example, about 100 Å to about 1,000 Å. When the hole transport region includes at least one of a hole injection layer and a hole transport layer, the thickness of the hole injection layer may be in a range of about 100 Å to about 10,000 Å, for example, about 100 Å to about 1,000 Å, and the thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 and HP-1, but embodiments are not limited thereto.

Compound HT-D1

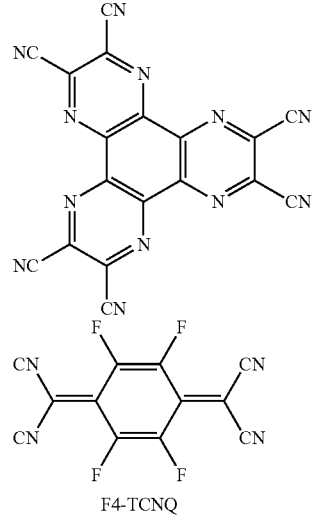

F4-TCNQ

HP-1

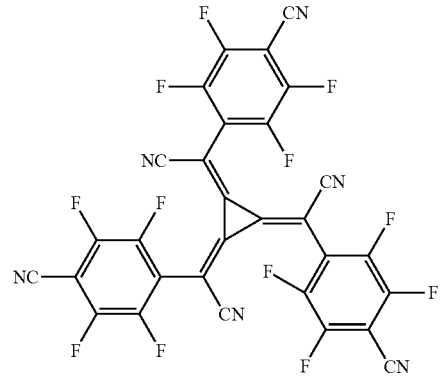

The hole transport region may further include a buffer layer.

The buffer layer may compensate for an optical resonance distance according to a wavelength of light emitted from the emission layer to improve the efficiency of an organic light-emitting device.

An emission layer may be formed on the hole transport region by using various methods, such as vacuum-deposition, spin coating, casting, or an LB method. When the emission layer is formed by vacuum-deposition or spin coating, vacuum-deposition and coating conditions for the emission layer may be generally similar to the conditions for forming a hole injection layer, though the conditions may vary depending on the compound used.

The hole transport region may further include an electron blocking layer. The electron blocking layer may include a known material, for example, mCP, but embodiments are not limited thereto.

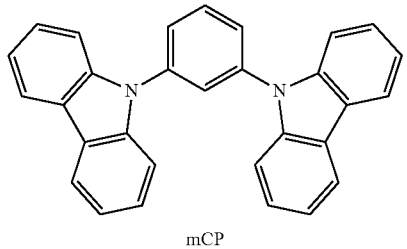 [SMILES: c1cc(-n2c3ccccc3c3ccccc32)cc(-n2c3ccccc3c3ccccc32)c1]

mCP

In some embodiments, the hole transport region may include an electron blocking layer, and the electron blocking layer may include the condensed cyclic compound represented by Formula 1.

A thickness of the electron blocking layer may be in a range of about 50 Å to about 1,000 Å, for example, about 70 Å to about 500 Å. While not wishing to be bound by theory, it is understood that when the thickness of the electron blocking layer is within this range, excellent electron blocking characteristics may be obtained without a substantial increase in driving voltage.

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the condensed cyclic compound represented by Formula 1. For example, the emission layer may only include the condensed cyclic compound represented by Formula 1. In some embodiments, the emission layer may include a host and a dopant, and the host may include the condensed cyclic compound represented by Formula 1. In some embodiments, the emission layer may include a host and a dopant, and the dopant may include the condensed cyclic compound represented by Formula 1.

According to an embodiment, a dopant in the emission layer may be a phosphorescent dopant, and the phosphorescent dopant may include an organometallic compound represented by Formula 81:

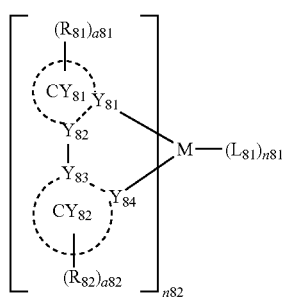

Formula 81

In Formula 81,

M may be selected from iridium (Ir), platinum (Pt), osmium (Os), titanium (Ti), zirconium (Zr), hafnium (Hf), europium (Eu), terbium (Tb), palladium (Pd) and thulium (Tm), $Y_{81}$ to $Y_{84}$ may each independently be carbon (C) or nitrogen (N), $Y_{81}$ and $Y_{82}$ may be linked to each other by a single bond or a double bond, and $Y_{83}$ and $Y_{84}$ may be linked to each other by a single bond or a double bond, $CY_{81}$ and $CY_{82}$ may be each independently selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isooxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzoimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group or a dibenzothiophene group, and $CY_{81}$ and $CY_{82}$ may be optionally further linked to each other by an organic linking group, $R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{10}$ alkyl group, a substituted or unsubstituted $C_2$-$C_{60}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{10}$ aryl group, a substituted or unsubstituted $C_6$-$C_{10}$ aryloxy group, a substituted or unsubstituted $C_6$-$C_{10}$ arylthio group, a substituted or unsubstituted $C_7$-$C_{10}$ arylalkyl group, a substituted or unsubstituted $C_1$-$C_{10}$ heteroaryl group, a substituted or unsubstituted $C_2$-$C_{60}$ heteroaryloxy group, a substituted or unsubstituted $C_2$-$C_{10}$ heteroarylthio group, a substituted or unsubstituted $C_3$-$C_{10}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$), a81 and a82 may each independently be an integer of 1 to 5, n81 may be an integer of 0 to 4, n82 may be 1, 2 or 3, $L_{81}$ may be a monovalent organic ligand, a divalent organic ligand or a trivalent organic ligand, and descriptions for Q$_1$ to Q$_7$ are same as descriptions for Q$_1$ to Q$_3$ in —Si(Q$_1$)(Q$_2$)(Q$_3$) in Formula 1.

Descriptions of $R_{81}$ and $R_{82}$ are the same as the description of $R_{11}$.

The phosphorescent dopant may include at least one selected from Compounds PD1 to PD78 or Flr$_6$, but embodiments are not limited thereto:

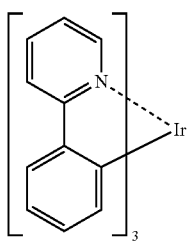 PD1
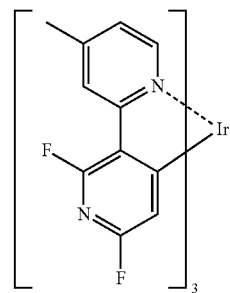 PD6
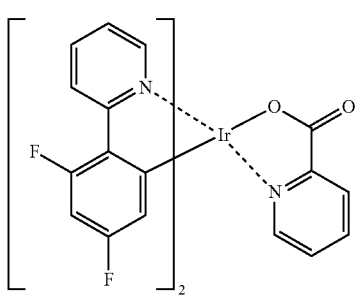 PD2
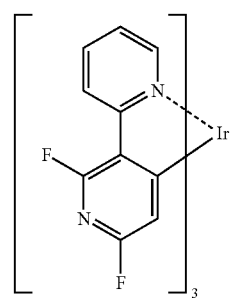 PD7
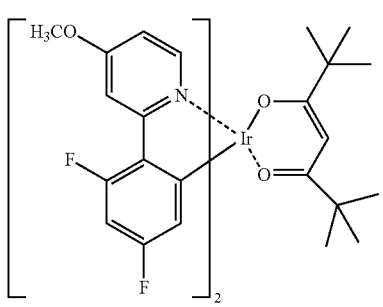 PD3
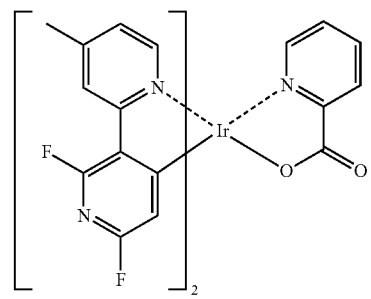 PD8
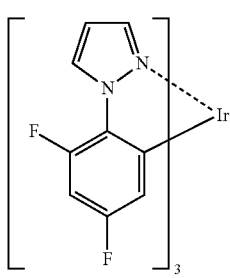 PD4
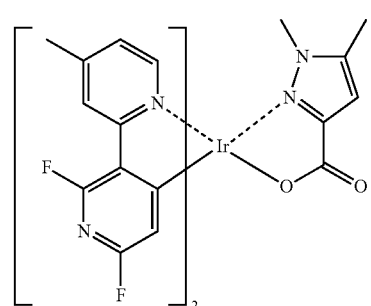 PD9
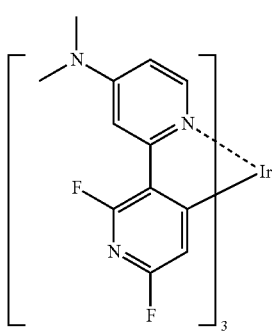 PD5
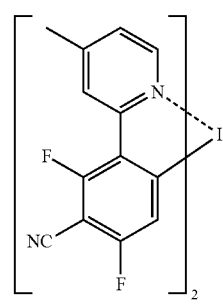 PD10

PD11
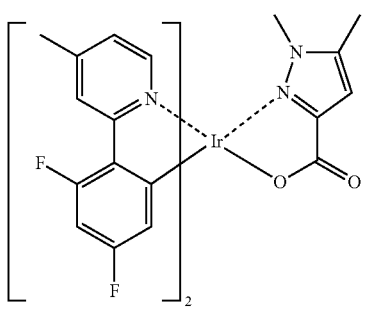
PD12
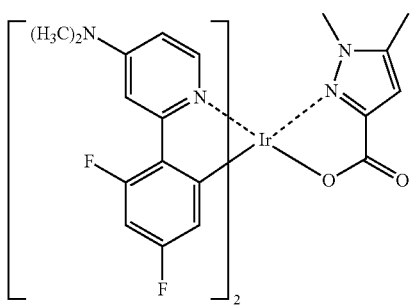
PD13
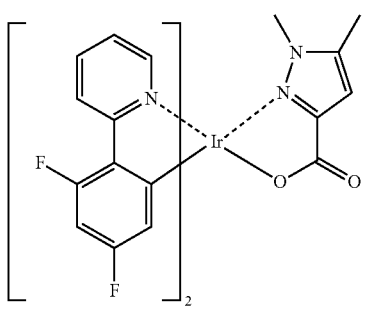
PD14
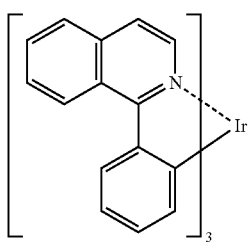
PD15
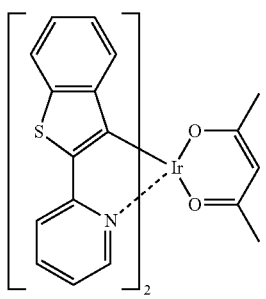
PD16
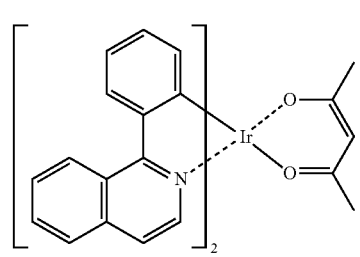
PD17
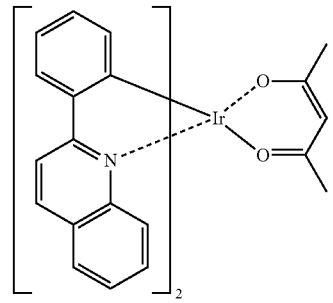
PD18
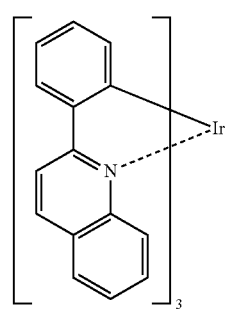
PD19
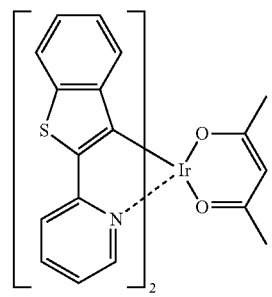
PD20
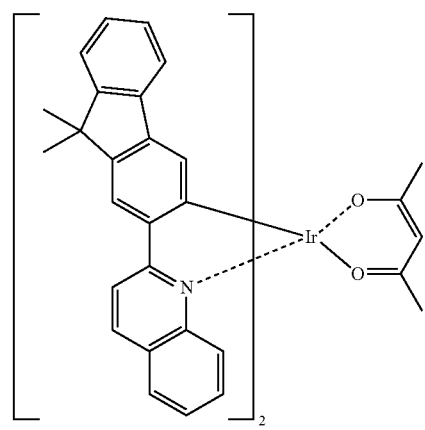

-continued
PD21
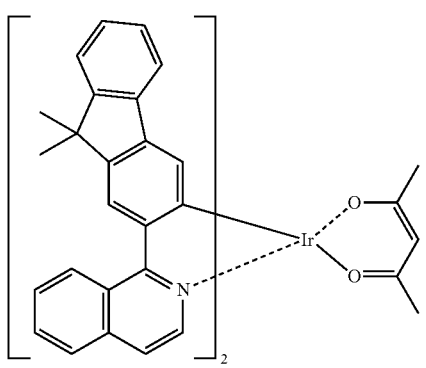
PD22
PD23
PD24
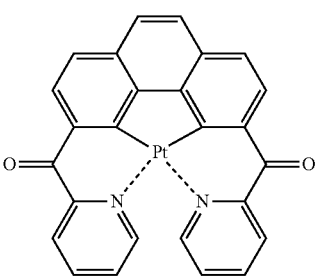
PD25
PD26
PD27
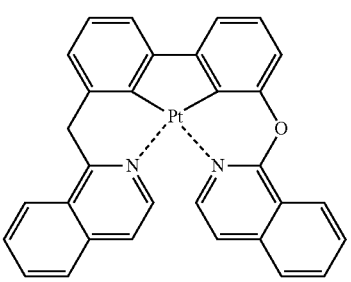
PD28
PD29
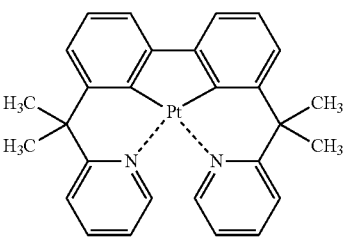
PD30
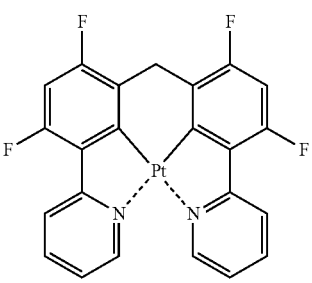
PD31
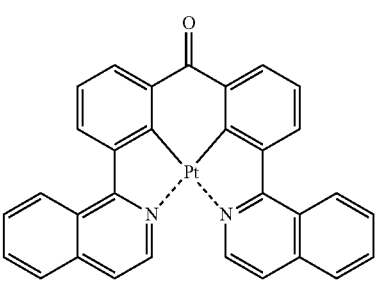
PD32
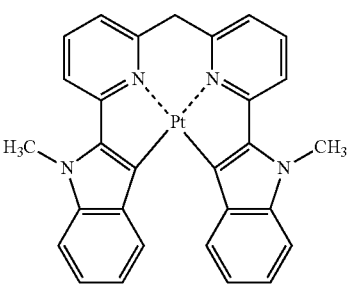

PD33 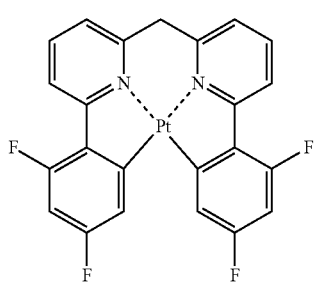
PD38 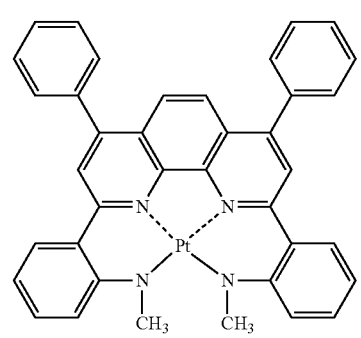
PD34 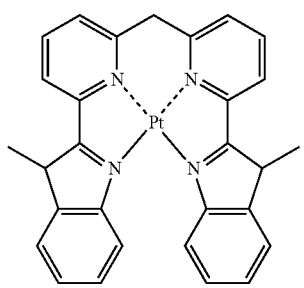
PD39 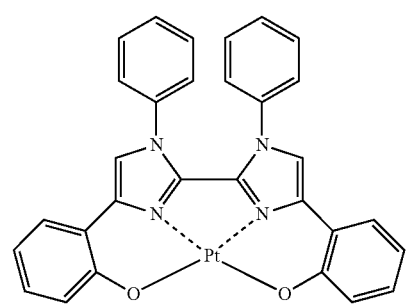
PD35 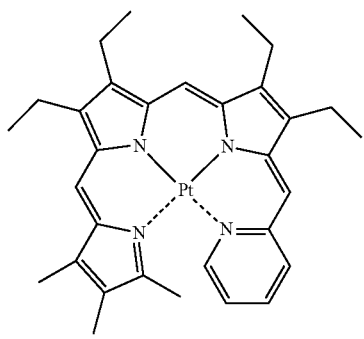
PD40 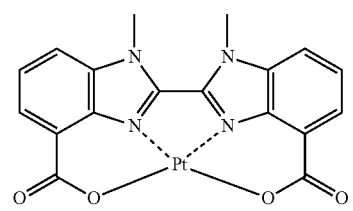
PD36 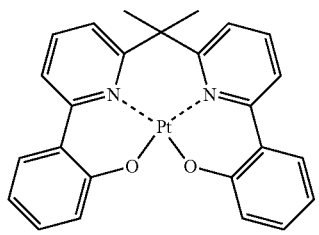
PD41 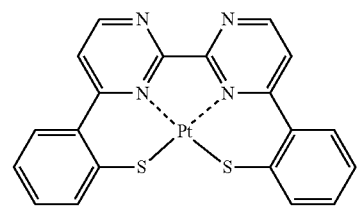
PD37 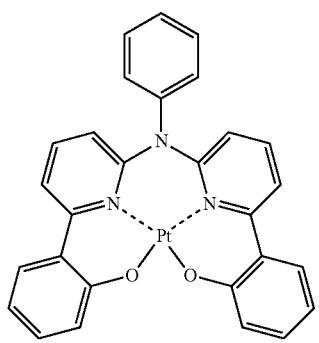
PD42 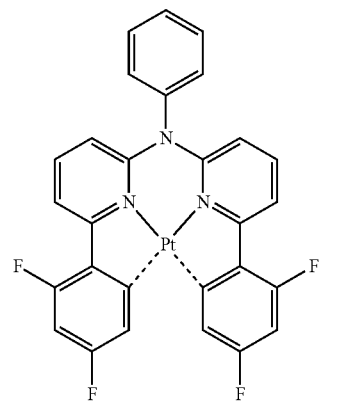

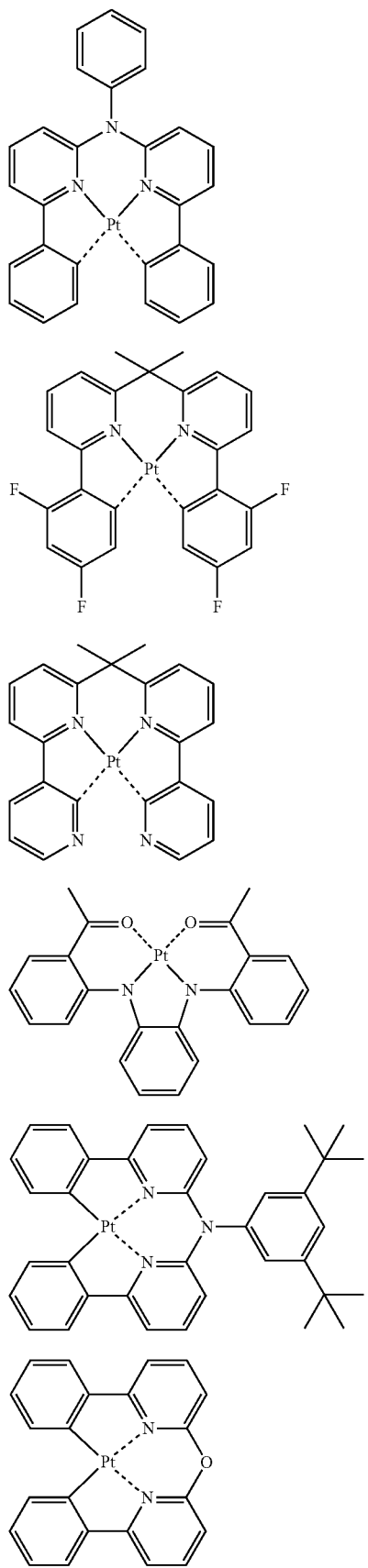
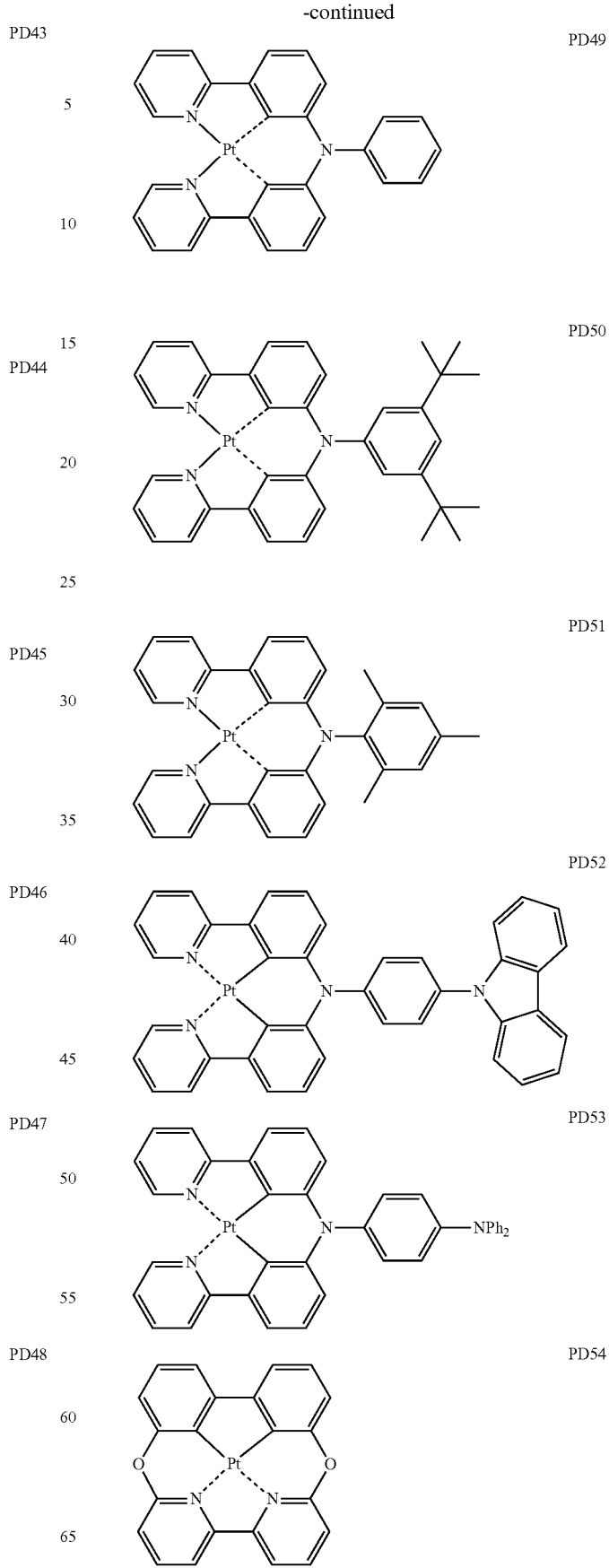

-continued
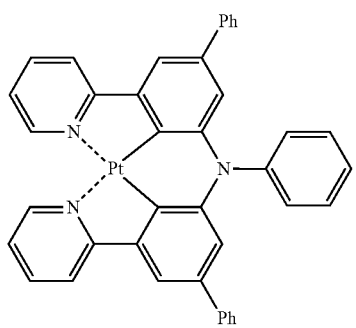
PD55
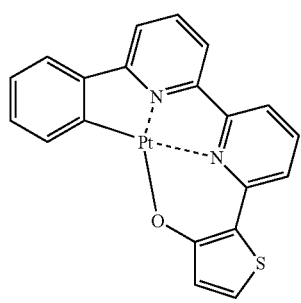
PD56
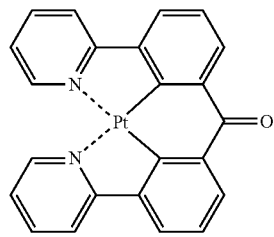
PD57
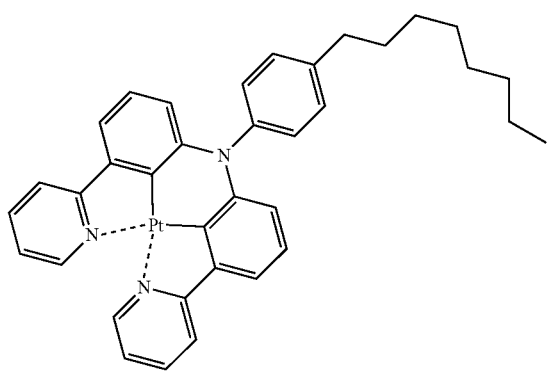
PD58
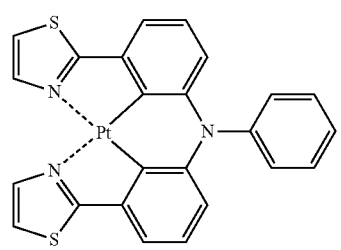
PD59
-continued
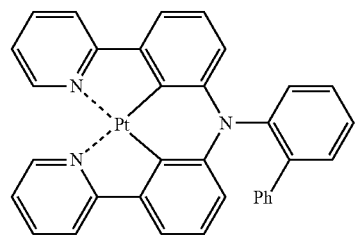
PD60
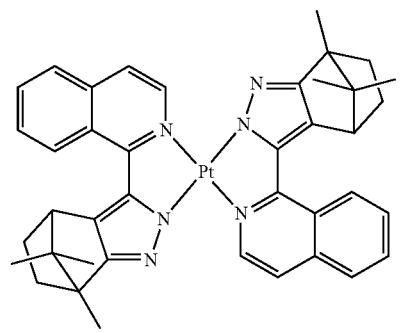
PD61
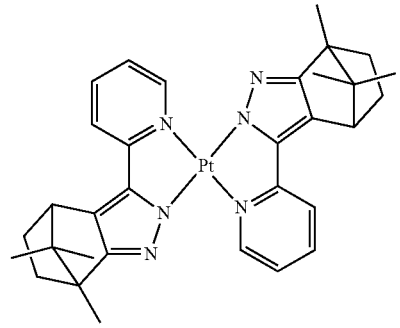
PD62
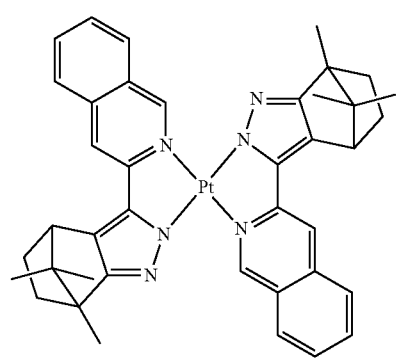
PD63
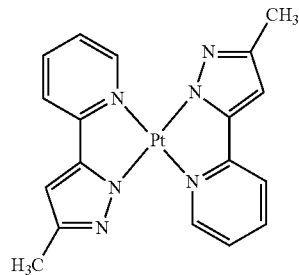
PD64

-continued
PD65
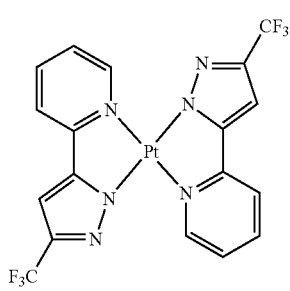
PD66
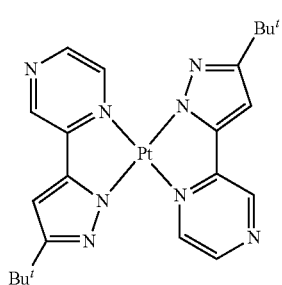
PD67
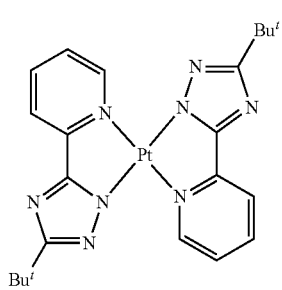
PD68
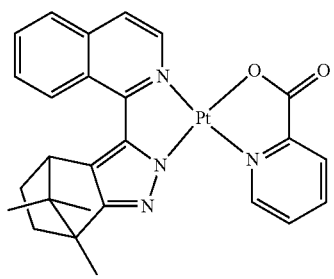
PD69
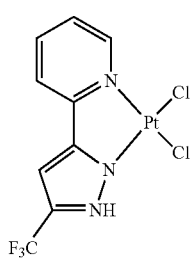
-continued
PD70
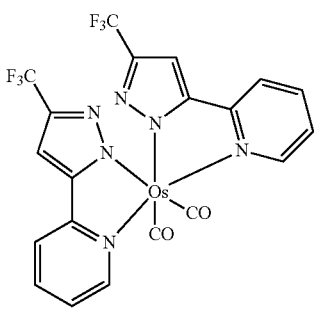
PD71
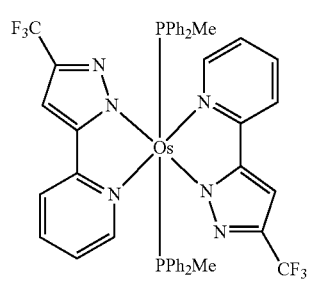
PD72
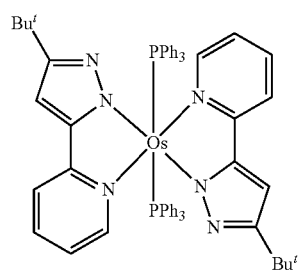
PD73
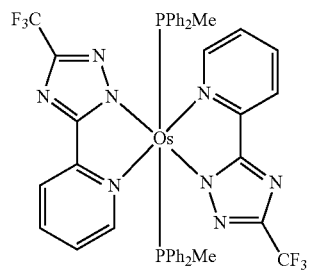
PD74
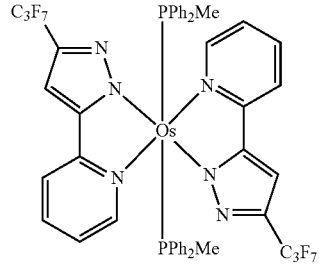

-continued

PD75
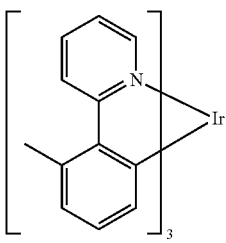

PD76
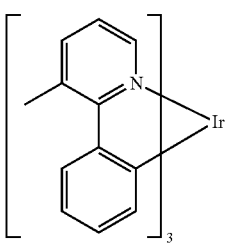

PD77
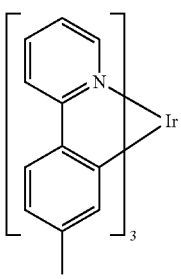

PD78
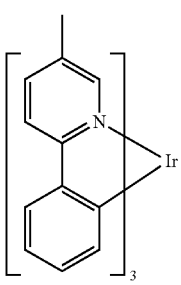

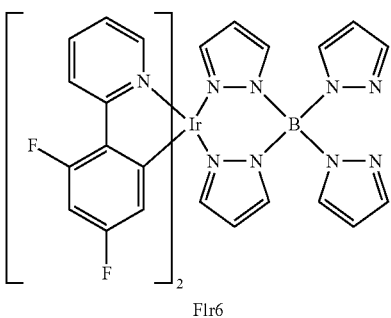
FIr6

In some embodiments, the phosphorescent dopant may include PtOEP:

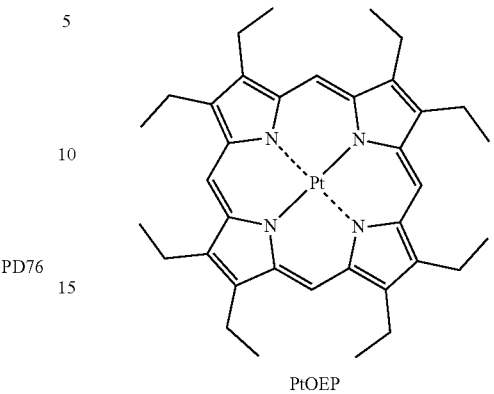
PtOEP

When the emission layer includes a host and a dopant, an amount of the dopant may be selected from a range of about 0.01 part by weight to about 20 parts by weight based on about 100 parts by weight of the host, but embodiments are not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

For example, the electron transport region may have a structure of a hole blocking layer/an electron transport layer/an electron injection layer or an electron transport layer/an electron injection layer, but it is not limited thereto. The electron transport layer may have a single layer structure or a multi-layer structure including two or more different materials.

The conditions for forming a hole blocking layer, an electron transport layer, and an electron injection layer, of the electron transport region, may be inferred based on the conditions for forming the hole injection layer.

When the electron transport region includes a hole blocking layer, the hole blocking layer may, for example, include at least one of BCP and Bphen, but is not limited thereto.

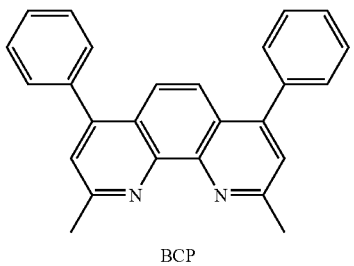
BCP

-continued

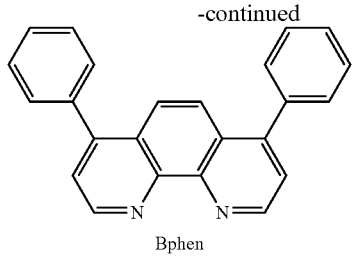

Bphen

-continued

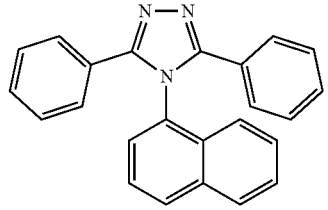

NTAZ

A thickness of the hole blocking layer may be in a range of about 20 Å to about 1,000 Å, for example, about 30 Å to about 300 Å. While not wishing to be bound by theory, it is understood that when the thickness of the hole blocking layer is within this range, excellent hole blocking characteristics may be obtained without a substantial increase in driving voltage.

The electron transport layer may further include at least one selected from BCP, BPhen, Alq$_3$, BAlq, TAZ, and NTAZ.

In some embodiments the electron transport layer may include at least one selected from Compounds ET1, ET2 and ET3, but it is not limited thereto.

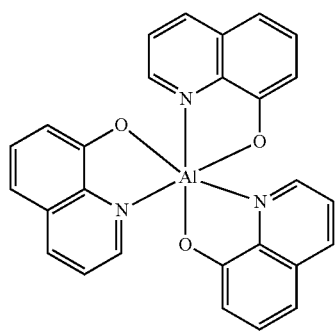

Alq$_3$

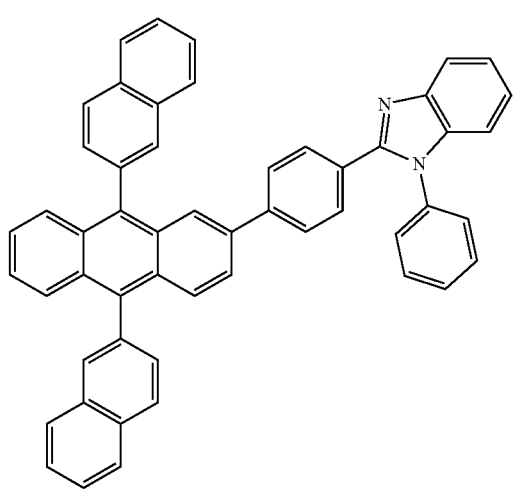

ET1

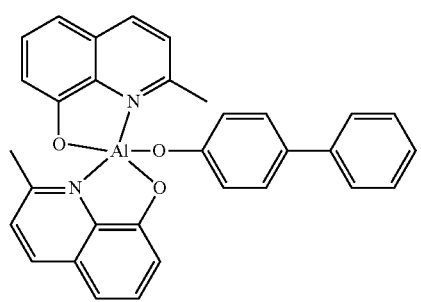

BAlq

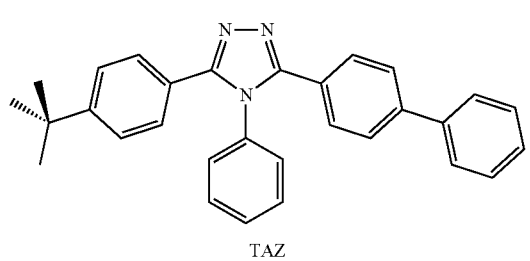

TAZ

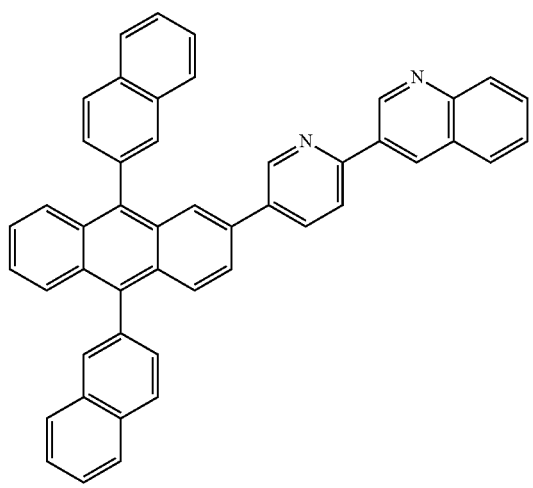

ET2

ET3

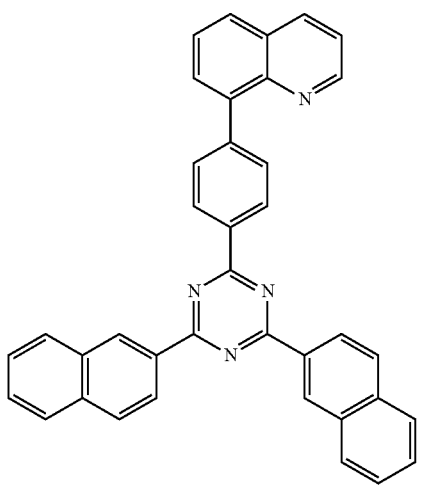

A thickness of the electron transport layer may be in a range of about 100 Å to about 1,000 Å, for example, about 150 Å to about 500 Å. While not wishing to be bound by theory, it is understood that when the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET-D1

ET-D2

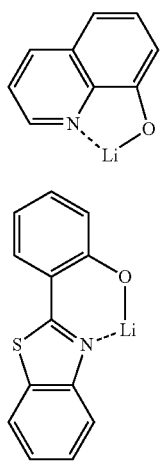

The electron transport region may include an electron injection layer (EIL) that facilitates electron injection from the second electrode 19.

The electron injection layer may include at least one selected from LiQ, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

According to an embodiment, the organic layer 15 of the organic light-emitting device 10 may include a hole transport region and an emission layer, and the hole transport region and the emission layer may include the condensed cyclic compound represented by Formula 1, wherein the condensed cyclic compound represented by Formula 1 included in the hole transport region may be the same as the condensed cyclic compound represented by Formula 1 included in the emission layer.

In some embodiments, the organic layer 15 of the organic light-emitting device 10 may include a hole transport region and an emission layer, and the hole transport region and the emission layer may include the condensed cyclic compound represented by Formula 1, wherein the condensed cyclic compound represented by Formula 1 included in the hole transport region may be different than the condensed cyclic compound represented by Formula 1 included in the emission layer.

Here, the hole transport region may include at least one of a hole transport layer and an electron blocking layer, and the condensed cyclic compound represented by Formula 1 may be included in:

i) the hole transport layer,
ii) the electron blocking layer or
iii) the hole transport layer and the electron blocking layer. The electron blocking layer may directly contact the emission layer.

Hereinbefore, an organic light-emitting device has been described with reference to FIG. 1, but embodiments are not limited thereto.

A $C_1$-$C_{60}$ alkyl group as used herein refers to a linear or branched aliphatic saturated hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group. A $C_1$-$C_{10}$ alkylene group as used herein refers to a divalent group having the same structure as a $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{10}$ alkenyl group as used herein refers to a group formed by substituting at least one carbon-carbon double bond in the middle or at the terminal of the $C_2$-$C_{10}$ alkyl group. Detailed examples thereof are an ethenyl group, a propenyl group, and a butenyl group. A $C_2$-$C_{10}$ alkenylene group as used herein refers to a divalent group having the same structure as a $C_2$-$C_{10}$ alkenyl group.

A $C_2$-$C_{60}$ alkynyl group as used herein refers to a group formed by substituting at least one carbon-carbon triple bond in the middle or at the terminal of the $C_2$-$C_{10}$ alkyl group. Detailed examples thereof are an ethynyl group and a propynyl group. A $C_2$-$C_{10}$ alkynylene group as used herein refers to a divalent group having the same structure as a $C_2$-$C_{10}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one heteroatom selected from N, O, P, Si, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in its ring, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one heteroatom selected from N, O, P, Si and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_2$-$C_{10}$ heterocycloalkenylene group as used herein refers to a divalent group having the same structure as a $C_1$-$C_{10}$ heterocycloalkenyl group.

A $C_6$-$C_{10}$ aryl group as used herein refers to a monovalent group having a carbocyclic aromatic system having 6 to 60 carbon atoms, and a $C_6$-$C_{10}$ arylene group as used herein refers to a divalent group having a carbocyclic aromatic system having 6 to 60 carbon atoms. Detailed examples of the $C_6$-$C_{10}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{10}$ arylene group each include two or more rings, the rings may be fused to each other.

A $C_1$-$C_{10}$ heteroaryl group as used herein refers to a monovalent group having a cyclic aromatic system including at least one heteroatom selected from N, O, P, Si and S as a ring-forming atom and 1 to 60 carbon atoms. A $C_1$-$C_{10}$ heteroarylene group as used herein refers to a divalent group having a cyclic aromatic system including at least one heteroatom selected from N, O, P, Si and S as a ring-forming atom and 1 to 60 carbon atoms. Detailed examples of the $C_1$-$C_{10}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{10}$ heteroarylene group each include a plurality of rings, the rings may be fused to each other.

A $C_6$-$C_{10}$ aryloxy group as used herein indicates —$OA_{102}$ (wherein $A_{102}$ is the $C_6$-$C_{60}$ aryl group), a $C_6$-$C_{10}$ arylthio group as used herein indicates —$SA_{103}$ (wherein $A_{103}$ is the $C_6$-$C_{60}$ aryl group), and a $C_7$-$C_{60}$ arylalkyl group as used herein indicates -$A_{104}A_{105}$ (wherein $A_{105}$ is the $C_6$-$C_{59}$ aryl group and $A_{104}$ is the $C_1$-$C_{53}$ alkyl group).

A $C_2$-$C_{10}$ heteroaryloxy group as used herein indicates —$OA_{106}$ (wherein $A_{106}$ is the $C_2$-$C_{60}$ heteroaryl group), a $C_2$-$C_{10}$ heteroarylthio group as used herein indicates —$SA_{107}$ (wherein $A_{107}$ is the $C_2$-$C_{10}$ heteroaryl group), and a $C_3$-$C_{60}$ heteroarylalkyl group as used herein indicates -$A_{108}A_{109}$ (wherein $A_{109}$ is the $C_2$-$C_{59}$ heteroaryl group and $A_{108}$ is the $C_1$-$C_{58}$ alkyl group).

A monovalent non-aromatic condensed polycyclic group as used herein refers to a monovalent group that has two or more rings condensed to each other, and only carbon atoms (for example, the number of carbon atoms may be in a range of 8 to 60) as ring-forming atoms, wherein the molecular structure as a whole is non-aromatic in the entire molecular structure. Detailed examples of the non-aromatic condensed polycyclic group include a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has a plurality of rings condensed with each other, has a heteroatom selected from N, O P, Si and S, other than carbon atoms (for example, the number of carbon atoms may be in a range of 1 to 60), as ring-forming atoms, wherein the molecular structure as a whole is non-aromatic in the entire molecular structure. The monovalent non-aromatic condensed heteropolycyclic group includes a carbazolyl group. A divalent non-aromatic condensed hetero-polycyclic group as used herein refers to a divalent group having the same structure as the monovalent non-aromatic condensed heteropolycyclic group.

In Formula 1, at least one substituent of the substituted $C_1$-$C_{10}$ alkyl group, substituted $C_2$-$C_{10}$ alkenyl group, substituted $C_2$-$C_{10}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{610}$ arylalkyl group, substituted $C_1$-$C_{60}$ heteroaryl group, substituted $C_2$-$C_{60}$ heteroaryloxy group, substituted $C_2$-$C_{10}$ heteroarylthio group, substituted $C_3$-$C_{60}$ heteroarylalkyl group, substituted monovalent non-aromatic condensed polycyclic group and substituted monovalent non-aromatic condensed heteropolycyclic group may be selected from a deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{60}$ alkynyl group and a $C_1$-$C_{10}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{60}$ aryloxy group, a $C_6$-$C_{60}$ arylthio group, a $C_7$-$C_{10}$ arylalkyl group, a $C_1$-$C_6$ heteroaryl group, a $C_2$-$C_{60}$ heteroaryloxy group, a $C_2$-$C_{10}$ heteroarylthio group, a $C_3$-$C_{10}$ heteroarylalkyl group, a monovalent non-aromatic condensed polycyclic group, a monovalent non-aromatic condensed heteropolycyclic group, —Si(Q$_{11}$)(Q$_{12}$)(Q$_{13}$), —N(Q$_{14}$)(Q$_{15}$) and —B(Q$_{16}$)(Q$_{17}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_2$-C$_{60}$ heteroaryloxy group, a C$_2$-C$_{10}$ heteroarylthio group, a C$_3$-C$_{10}$ heteroarylalkyl group, a monovalent non-aromatic condensed polycyclic group and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{10}$ aryl group, a C$_6$-C$_{10}$ aryloxy group, a C$_6$-C$_{60}$ arylthio group, a C$_7$-C$_{60}$ arylalkyl group, a C$_1$-C$_{60}$ heteroaryl group, a C$_2$-C$_{60}$ heteroaryloxy group, a C$_2$-C$_{10}$ heteroarylthio group, a C$_3$-C$_{10}$ heteroarylalkyl group, a monovalent non-aromatic condensed polycyclic group and a monovalent non-aromatic condensed heteropolycyclic group, each substituted with at least one selected from a deuterium, —CD$_3$, —CD$_2$H, —CDH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_2$-C$_{10}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_2$-C$_{10}$ heteroaryloxy group, a C$_2$-C$_{10}$ heteroarylthio group, a C$_3$-C$_{60}$ heteroarylalkyl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$) and —B(Q$_{26}$)(Q$_{27}$); and —Si(Q$_{31}$)(Q$_{32}$)(Q$_{33}$), —N(Q$_{34}$)(Q$_{35}$) and —B(Q$_{36}$)(Q$_{37}$), and Q$_1$ to Q$_7$, Q$_{11}$ to Q$_{17}$, Q$_{21}$ to Q$_{27}$ and Q$_{31}$ to Q$_{37}$ may be each independently selected from a hydrogen, a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{10}$ alkyl group, a substituted or unsubstituted C$_2$-C$_{10}$ alkenyl group, a substituted or unsubstituted C$_2$-C$_{10}$ alkynyl group, a substituted or unsubstituted C$_1$-C$_{10}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{10}$ aryl group, a substituted or unsubstituted C$_6$-C$_{10}$ aryloxy group, a substituted or unsubstituted C$_6$-C$_{60}$ arylthio group, a substituted or unsubstituted C$_7$-C$_{10}$ arylalkyl group, a substituted or unsubstituted C$_1$-C$_{60}$ heteroaryl group, a substituted or unsubstituted C$_2$-C$_{60}$ heteroaryloxy group, a substituted or unsubstituted C$_2$-C$_{10}$ heteroarylthio group, a substituted or unsubstituted C$_3$-C$_{10}$ heteroarylalkyl group, a substituted or unsubstituted monovalent non-aromatic condensed polycyclic group and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted C$_1$-C$_{10}$ alkyl" refers to a C$_1$-C$_{60}$ alkyl group substituted with C$_6$-C$_{10}$ aryl group, the total number of carbon atoms in the resulting aryl substituted alkyl group is C$_7$-C$_{120}$.

The term "a biphenyl group" as used herein refers to a monovalent group in which two benzene rings are linked to each other by a single bond.

The term "a terphenyl group" as used herein refers to a monovalent group in which three benzene rings are linked to each other by a single bond.

Hereinafter, a compound and an organic light-emitting device according to an embodiment of the present disclosure will be described in detail with reference to Synthesis Examples and Examples. However, the present disclosure is not limited thereto. The expression "B was used instead of A" used in describing Synthesis Examples means that an amount of B used was identical to an amount of A used based on molar equivalence.

EXAMPLE

Synthesis Example 1: Synthesis of Compound 86

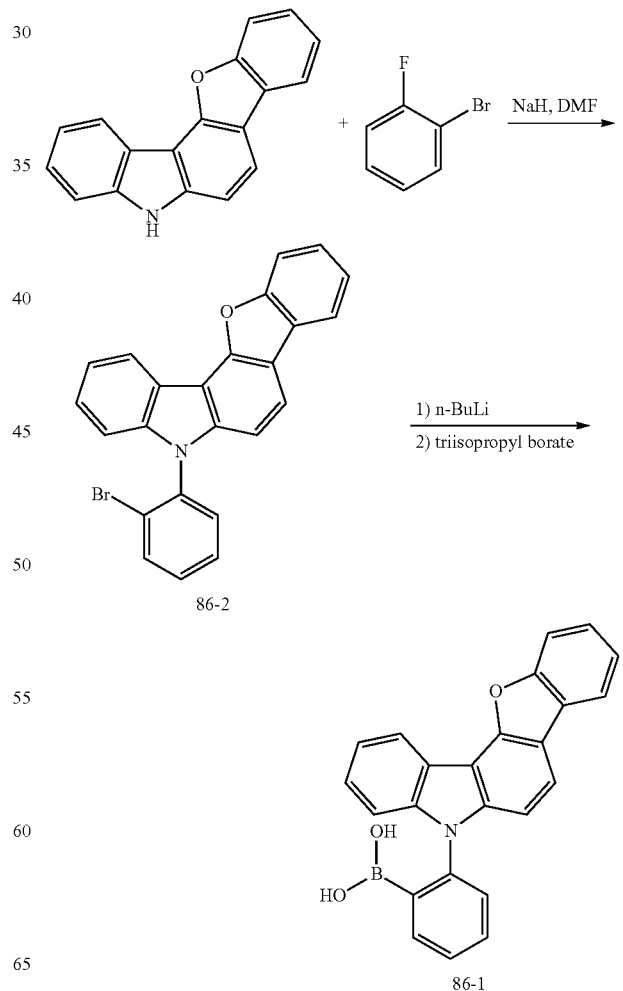

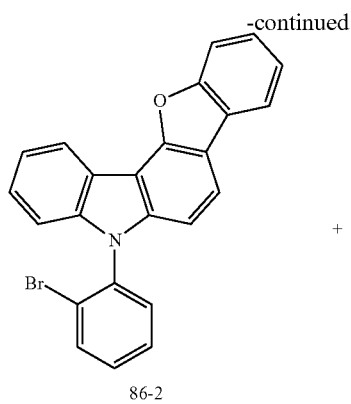

86-2

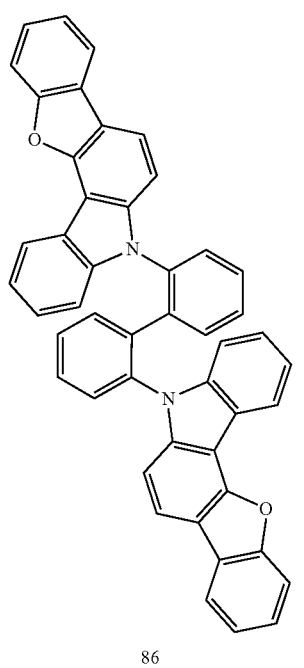

86-1

86

Synthesis of Intermediate 86-2

6.24 grams (g) (24.26 millimoles (mmol)) of 5H-benzofuro[3,2-c]carbazole was added to 80 milliliters (ml) of DMF and then 1.16 g (29.11 mmol) of NaH (60% dispersion in mineral oil) was added thereto at 0° C. The resulting mixture was stirred at room temperature for an hour. Then, 5.52 g (31.53 mmol) of 1-bromo-2-fluorobenzene was added thereto and stirred for 18 hours while being heated at 150° C. 100 ml of ethyl acetate was added thereto, and then the result was cleaned with 100 ml of water twice and dried with MgSO$_4$. Then, ethyl acetate was removed therefrom by using a rotavapor to obtain a viscous product. The product was purified by silica gel column chromatography to obtain 7.6 g of Intermediate 86-2. The identity of obtained Intermediate 86-2 was confirmed by LC-MS.

Synthesis of Intermediate 86-1

11.35 g (27.53 mmol) of Intermediate 86-2 was melted with 92 ml of anhydrous THF and then 1.6 molar (M) (20.6 ml) of n-BuLi was slowly added thereto at −78° C. for an hour. After a 3-hour reaction, 8.80 g (46.80 mmol) of triisopropyl borate was added thereto and a reaction temperature was slowly increased to room temperature. Then, 1 normal (N) (10 ml) of HCl was added thereto, and the resultant was stirred for 2 hours. A solvent was removed by using a rotavapor, and the resultant was melted by adding 200 ml of methylene chloride thereto and cleaned with 100 ml of water twice, thereby obtaining a white solid. Slurry treatments by using 1 liter (L) of hexane and 1 L of MeOH were respectively performed on the white solid to obtain 6.5 g of Intermediate 86-1. The identity of obtained Intermediate 86-1 was confirmed by LC-MS.

$C_{24}H_{16}BNO_3$: [M+H]=377.09

Synthesis of Compound 86

3.92 g of Intermediate 86-2, 4.34 g of Intermediate 86-1, 0.41 g (0.44 mmol) of Pd(PPh$_3$)$_4$ and 2.45 g (17.71 mmol) of K$_2$CO$_3$ were mixed with 35 ml/5 ml of THF/H$_2$O, and the result was stirred for 18 hours while being heated at 80° C. The result was precipitated/stirred/filtered with 500 ml of MeOH to obtain a solid compound, and the solid compound was purified by silica gel column chromatography to obtain 3.9 g of Compound 86. The identity of obtained Compound 86 was confirmed by LC-MS.

$C_{48}H_{28}N_2O_2$: [M+H]=664.54

Synthesis Example 2: Synthesis of Compound 87

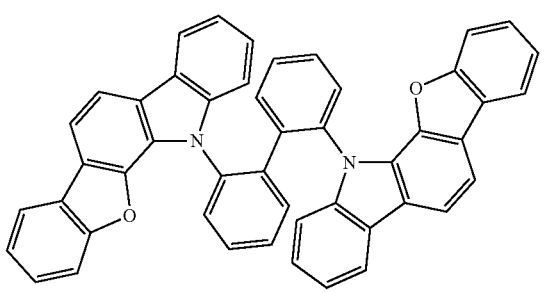

87

Compound 87 was synthesized in the same manner as in Synthesis Example 1, except that, when synthesizing Intermediate 86-2, 12H-benzofuro[2,3-a]carbazole was used instead of 5H-benzofuro[3,2-c]carbazole. The synthesized Compound was confirmed by LC-MS.

Synthesis Example 3: Synthesis of Compound 88

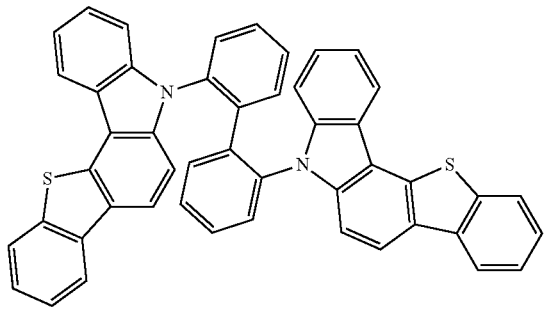
88

Compound 88 was synthesized in the same manner as in Synthesis Example 1, except that, when synthesizing Intermediate 86-2, 5H-benzo[4,5]thieno[3,2-c]carbazole was used instead of 5H-benzofuro[3,2-c]carbazole. The synthesized Compound was confirmed by LC-MS.

$C_{48}H_{28}N_2S_2$: [M+H]=696.12

Synthesis Example 4: Synthesis of Compound 89

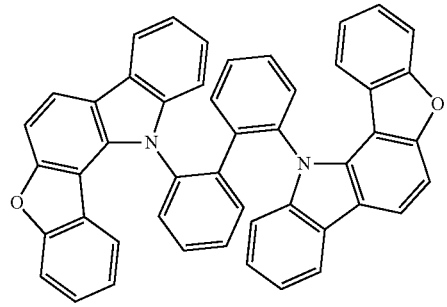
89

Compound 89 was synthesized in the same manner as in Synthesis Example 1, except that, when synthesizing Intermediate 86-2, 12H-benzofuro[3,2-a]carbazole was used instead of 5H-benzofuro[3,2-c]carbazole. The synthesized Compound was confirmed by LC-MS.

$C_{48}H_{28}N_2O_2$: [M+H]=664.62

Synthesis Example 5: Synthesis of Compound 27

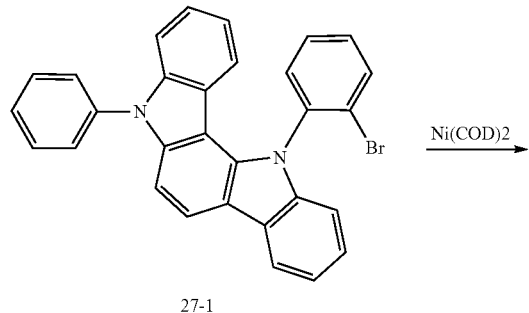
27-1

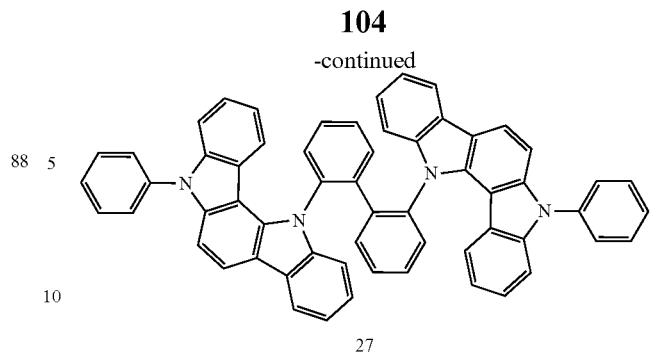
27

4.05 g of Ni(COD)$_2$, 1.59 g of COD, and 2.30 g of bi-pyridyl were mixed with 24 ml of DMF and the resultant was heated to 85° C. and stirred for 30 minutes. Then, a mixture of 5 ml of toluene and 4.78 g of Intermediate 27-1 was slowly added thereto and the resultant was heated and stirred for 3 hours. Then, a mixture of conc. HCl/MeOH/acetone (1/1/1) was slowly added thereto to form a precipitate, the precipitate was filtered using a paper and cleaned with MeOH to obtain a solid compound, and the solid compound was subjected to silica hot filtering using xylene and recrystallization with dichloromethane/xylene to obtain 5.50 g of Compound 27. The obtained Compound 27 was confirmed by LC-MS.

$C_{60}H_{38}N_4$: [M+H]=814.30

Synthesis Example 6: Synthesis of Compound 32

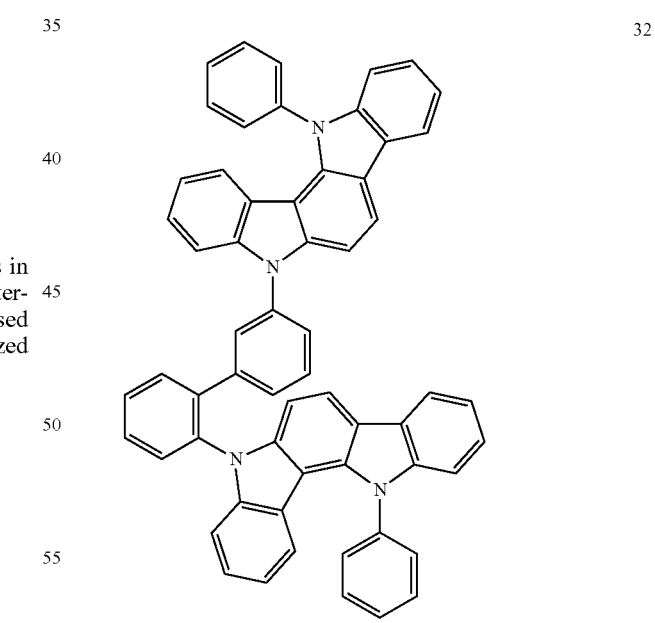
32

Compound 32 was synthesized in the same manner as in Synthesis Example 5, except that 5-(2-bromophenyl)-12-phenyl-5,12-dihydroindolo[3,2-a]carbazole was used instead of Intermediate 27-1. The synthesized Compound was confirmed by LC-MS.

$C_{60}H_{38}N_4$: [M+H]=814.34

105
Synthesis Example 7: Synthesis of Compound 80

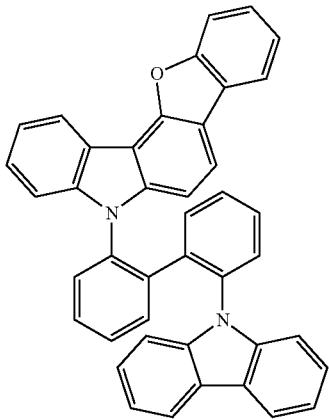

Compound 80 was synthesized in the same manner as in Synthesis Example 1, except that, when synthesizing Compound 86, (2-(9H-carbazol-9-yl)phenyl)boronic acid was used instead of Intermediate 86-1. The synthesized Compound was confirmed by LC-MS.

Synthesis Example 8: Synthesis of Compound 91

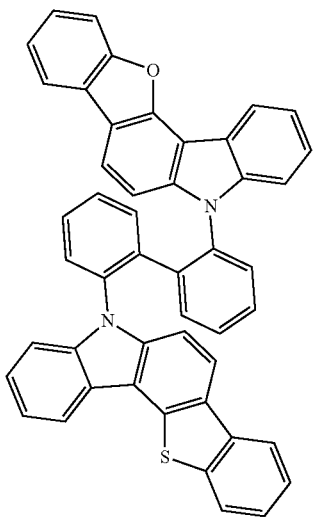

Compound 91 was synthesized in the same manner as in Synthesis Example 1, except that, when synthesizing Compound 86, (2-(5H-benzo[4,5]thieno[3,2-c]carbazol-5-yl)phenyl)boronic acid was used instead of Intermediate 86-1. The synthesized Compound was confirmed by LC-MS.

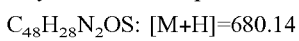

106
Synthesis Example 9: Synthesis of Compound 97

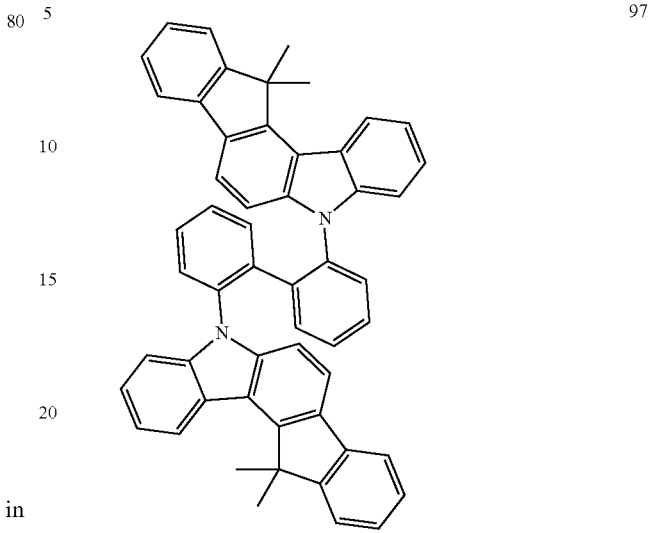

Compound 97 was synthesized in the same manner as in Synthesis Example 5, except that 5-(2-bromophenyl)-12,12-dimethyl-5,12-dihydroindeno[1,2-c]carbazole was used instead of Intermediate 27-1. The synthesized Compound was confirmed by LC-MS.

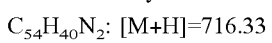

Example 1

A glass substrate having a thickness of 1,500 Å and an indium tin oxide (ITO) electrode as a first electrode (anode) thereon was sonicated with distilled water, and then further sonicated with iso-propyl alcohol, acetone, and methanol, and dried to be placed in a plasma cleaner. Next, the glass substrate was cleaned for 5 minutes by using oxygen plasma and then mounted on a vacuum deposition apparatus.

Compound HT3 and Compound HP-1 were co-deposited on the ITO electrode of the glass substrate to form a hole injection layer having a thickness of 100 Å, and Compound HT3 was deposited on the hole injection layer to form a hole transport layer having a thickness of 1,300 Å. mCP was deposited on the hole transport layer to form an electron blocking layer having a thickness of 150 Å, thereby forming a hole transport region.

Compound 86 (host) and Flr6 (dopant, 10 percent by weight (wt %)) were co-deposited on the hole transport region to form an emission layer having a thickness of 300 Å.

BCP was vacuum-deposited on the emission layer to form a hole blocking layer having a thickness of 100 Å, and Compound ET3 and Liq were vacuum-deposited on the hole blocking layer to form an electron transport layer having a thickness of 250 Å. Liq was deposited on the electron transport layer to form an electron injection layer having a thickness of 5 Å and an Al second electrode (cathode) having a thickness of 1,000 Å was formed on the electron injection layer, thereby manufacturing an organic light-emitting device.

Examples 2 to 9 and Comparative Example 1

Organic light-emitting devices were manufactured in the same manner as in Example 1, except that when forming an emission layer, compounds shown in Table 2 were used instead of Compound 86.

Evaluation Example 1: Characteristic Evaluation of Organic Light-Emitting Device Driving voltage, current density, luminous efficiency, power efficiency, quantum luminance efficiency and lifespan of each of the organic light-emitting devices manufactured in Examples 1 to 9 and Comparative Example 1 were measured by using a current-voltage meter (Keithley 2400) and a luminance meter (Minolta Cs-1000 Å). The results thereof are shown in Table 2. $T_{95}$ (at 500 candelas per meter, cd/m$^2$) in Table 2 refers to an amount of time until luminance was decreased to 95% of its initial luminance. In Table 2, the driving voltage, luminous efficiency, power efficiency, quantum luminance efficiency and lifespan of Examples 1 to 9 were expressed in a relative value compared to "100", which denotes the driving voltage, luminous efficiency, power efficiency, quantum luminance efficiency and lifespan of Comparative Example 1.

TABLE 2

|  | host | driving voltage (V) | Luminous efficiency (cd/A) | Power efficiency (lm/W) | quantum luminance efficiency (%) | $T_{95}$ (hr) |
| --- | --- | --- | --- | --- | --- | --- |
| Example 1 | 86 | 89% | 114% | 128% | 113% | 256% |
| Example 2 | 87 | 105% | 105% | 108% | 104% | 142% |
| Example 3 | 88 | 101% | 129% | 128% | 129% | 167% |
| Example 4 | 89 | 98% | 109% | 116% | 111% | 120% |
| Example 5 | 27 | 107% | 104% | 108% | 103% | 103% |
| Example 6 | 32 | 101% | 120% | 118% | 117% | 123% |
| Example 7 | 80 | 87% | 117% | 115% | 112% | 208% |
| Example 8 | 91 | 95% | 122% | 128% | 121% | 212% |
| Example 9 | 97 | 99% | 117% | 114% | 115% | 93% |
| Comparative Example 1 | Compound B | 100% | 100% | 100% | 100% | 100% |

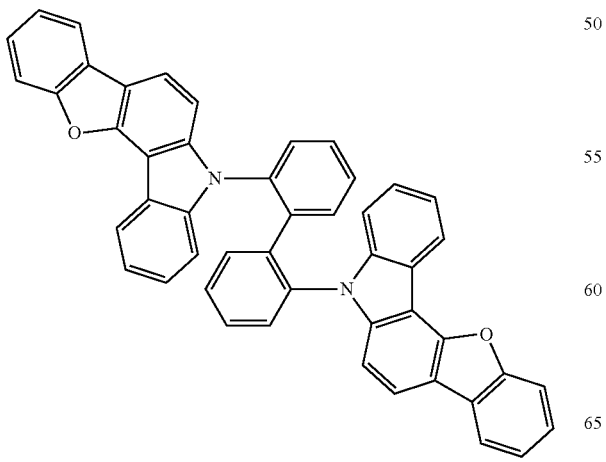

86

87
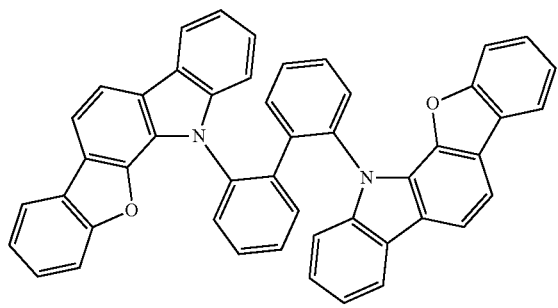
88
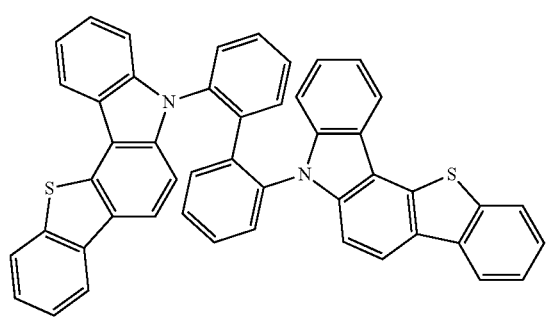
89
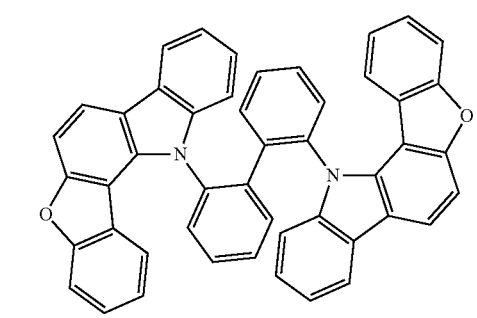
27
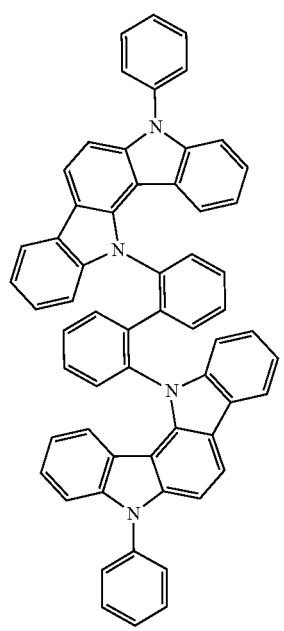
32
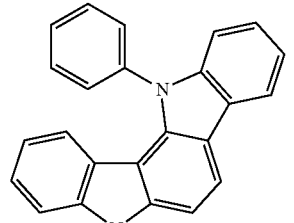
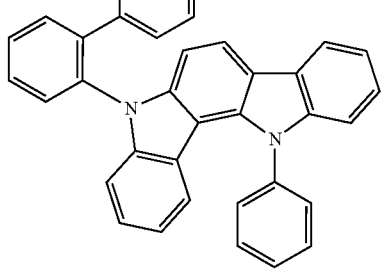
80
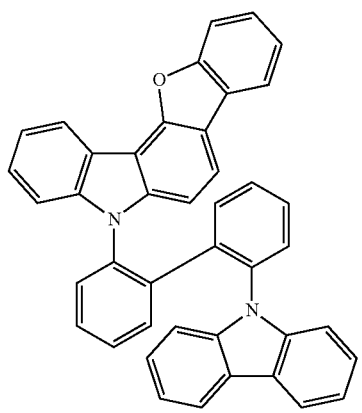
91
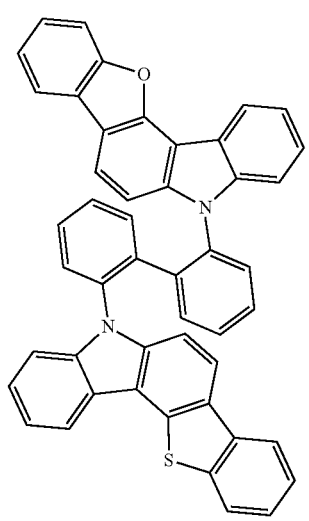

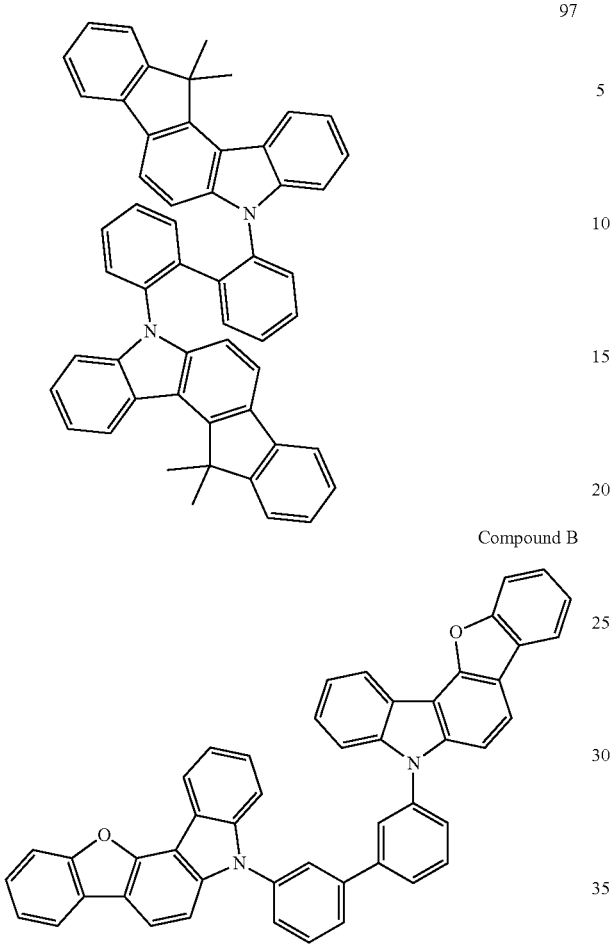

Compound B

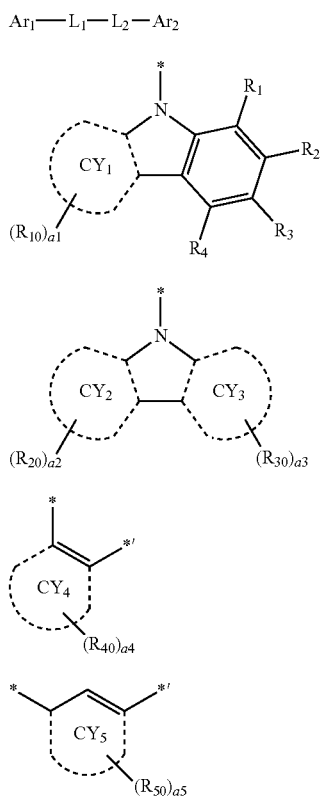

Table 2 shows that the organic light-emitting devices of Examples 1 to 9 have lower or comparable driving voltage, higher luminous efficiency, higher power efficiency, higher quantum luminance efficiency and longer of comparable lifespan, compared to the organic light-emitting device of Comparative Example 1.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:
1. An organic light-emitting device comprising:
   a first electrode;
   a second electrode; and
   an organic layer disposed between the first electrode and the second electrode and comprising an emission layer, wherein the emission layer comprises a host and a dopant, wherein the host comprises one or more of a condensed cyclic compound represented by Formula 1:

in Formulae 1 to 5,
$Ar_1$ is a group represented by Formula 2,
$Ar_2$ is a group represented by Formula 3,
$CY_1$ is selected from a fluorene group, a carbazole group, and a dibenzofuran group,
$CY_2$ and $CY_3$ are each a benzene group,
i) $L_1$ is a group represented by Formula 4 and $L_2$ is a group represented by Formula 5;
ii) $L_1$ is a group represented by Formula 5 and $L_2$ is a group represented by Formula 4; or
iii) $L_1$ and $L_2$ are each independently a group represented by Formula 4,
$CY_4$ and $CY_5$ are each independently selected from $C_5$-$C_{30}$ carbocyclic groups,
$R_1$ to $R_4$, $R_{10}$, $R_{20}$ and $R_{30}$ are each independently selected from a hydrogen, a deuterium, a cyano group (CN), a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), $R_{40}$ and $R_{50}$ are each independently selected from a hydrogen, a deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), a1 to a5 are each independently an integer of 0 to 10, each of * and *' is a binding site to a neighboring atom, at least one substituent of the substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, substituted $C_3$-$C_{60}$ heteroarylalkyl group, substituted monovalent non-aromatic condensed polycyclic group and substituted monovalent non-aromatic condensed heteropolycyclic group is selected from:

a deuterium, —$CD_3$, —$CD_2H$, —$CDH_2$, a cyano group, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —$CD_3$, —$CD_2H$, —$CDH_2$, a cyano group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$) and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group and a monovalent non-aromatic condensed heteropolycyclic group, each substituted with at least one selected from a deuterium, —$CD_3$, —$CD_2H$, —$CDH_2$, a cyano group, a $C_1$-Coo alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$); and —Si($Q_{31}$)($Q_{32}$)($Q_{33}$), —N($Q_{34}$)($Q_{35}$) and —B($Q_{36}$)($Q_{37}$), and $Q_1$ to $Q_7$, $Q_{11}$ to $Q_{17}$, $Q_{21}$ to $Q_{27}$ and $Q_{31}$ to $Q_{37}$ are each independently selected from a hydrogen, a deuterium, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group and a substituted or unsubstituted monovalent non-aromatic condensed heteropolycyclic group.

2. The organic light-emitting device of claim 1, wherein $Ar_1$ is selected from groups represented by Formulae 2-1 to 2-6, and $Ar_2$ is selected from groups represented by Formula 3-7:

Formula 2-1

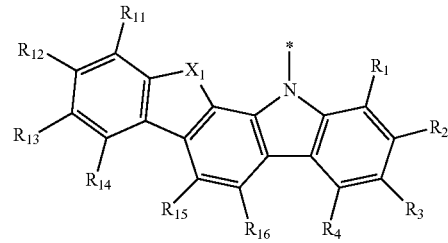

Formula 2-2

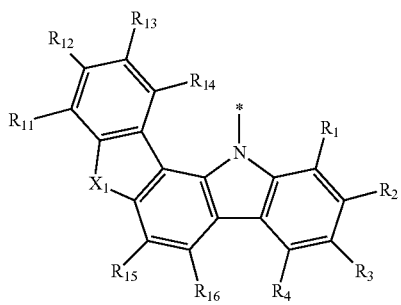

Formula 2-3

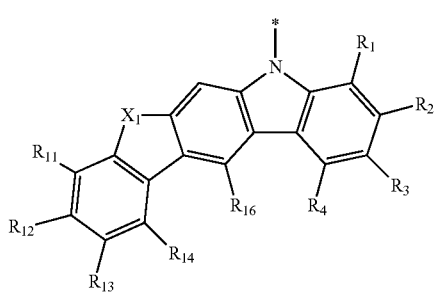

Formula 2-4

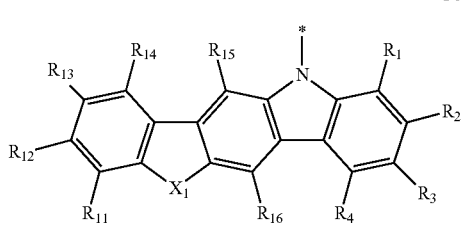

Formula 2-5

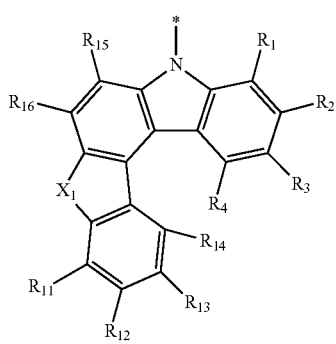

Formula 2-6

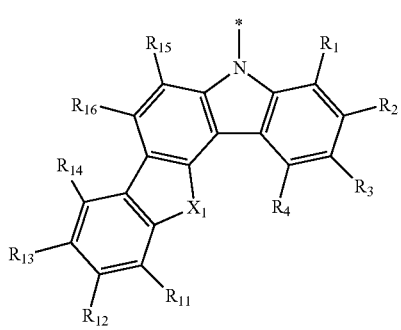

Formula 3-5

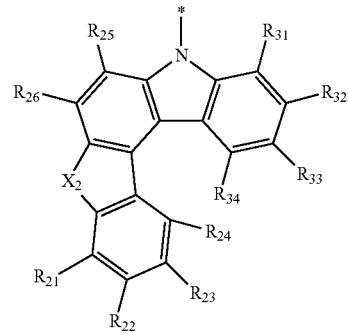

Formula 3-6

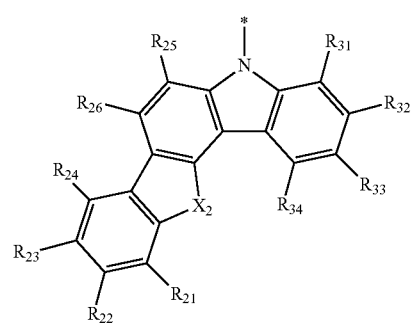

Formula 3-7

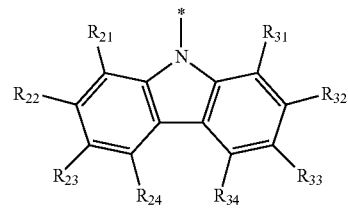

Formula 3-7

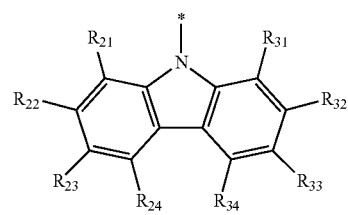

in Formulae 2-1 to 2-6 and 3-7, $X_1$ is $C(R_{17})(R_{18})$, $N(R_{19})$, O, $R_1$ to $R_4$ are each independently the same as described in claim 1, $R_{11}$ to $R_{19}$ are each independently the same as $R_{10}$ in claim 1, $R_{21}$ to $R_{24}$ are each independently the same as $R_{20}$ in claim 1, $R_{31}$ to $R_{34}$ are each independently the same as $R_{30}$ in claim 1, and is a binding site to a neighboring atom.

3. The organic light-emitting device of claim 2, wherein $R_1$ to $R_4$, $R_{11}$ to $R_{19}$, $R_{21}$ to $R_{24}$ and $R_{31}$ to $R_{34}$ are each independently selected from a hydrogen, a deuterium, a cyano group (CN), a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a cyano group (CN), a phenyl group, a biphenyl group, a terphenyl group and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group and a dibenzothiophenyl group, each substituted with at least one selected from a deuterium, a cyano group, a $C_1$-$C_{20}$ alkyl group, a $C_1$-$C_{20}$ alkoxy group, a phenyl group, a biphenyl group, a terphenyl group, a naphthyl group and —Si($Q_{31}$)($Q_{32}$)($Q_{33}$); and —Si($Q_1$)($Q_2$)($Q_3$), and $Q_1$ to $Q_3$ and $Q_{31}$ to $Q_{33}$ are each independently selected from a hydrogen, a $C_1$-$C_{20}$ alkyl group, a $C_1$-$C_{20}$ alkoxy group, a phenyl group, a biphenyl group, a terphenyl group and a naphthyl group.

4. The organic light-emitting device of claim 2, wherein $X_1$ is O.

5. The organic light-emitting device of claim 1, wherein $CY_4$ and $CY_5$ are each independently selected from a benzene group, a naphthalene group, a fluorene group, a carbazole group, a dibenzofuran group, and a dibenzothiophene group.

6. The organic light-emitting device of claim 1, wherein the condensed cyclic compound is represented by one of Formulae 1-1 to 1-3:

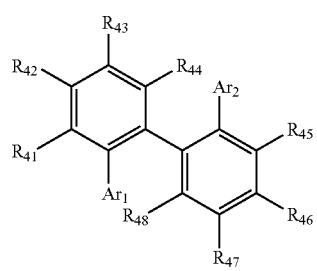

Formula 1-1

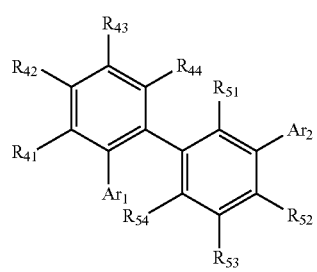

Formula 1-2

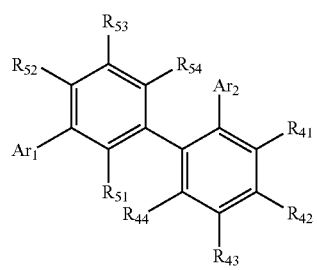

Formula 1-3 in Formulae 1-1 and 1-3, $Ar_1$ and $Ar_2$ are the same as in claim 1, $R_{41}$ to $R_{48}$ are each independently the same as $R_{40}$ in claim 1, and $R_{51}$ to $R_{54}$ are each independently the same as $R_{50}$ in claim 1.

7. The organic light-emitting device of claim 1, wherein the host comprises a compound selected from Compounds 33 to 44, 49, 54, 57 57 to 75, 80 to 85, 90 and 103 to 108:

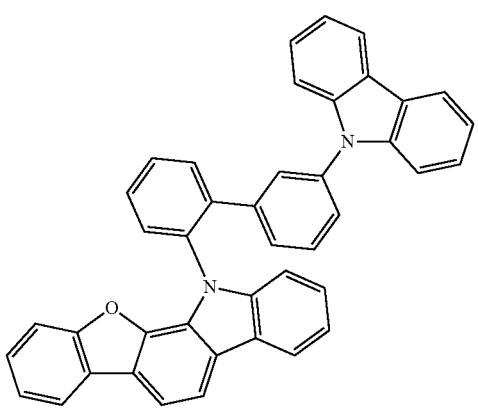

33

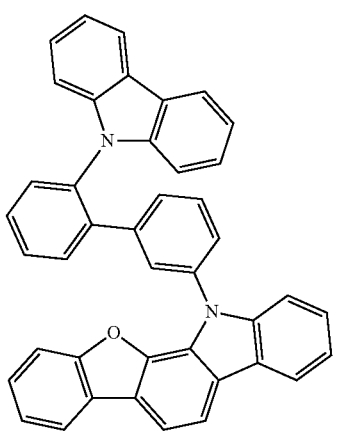

34

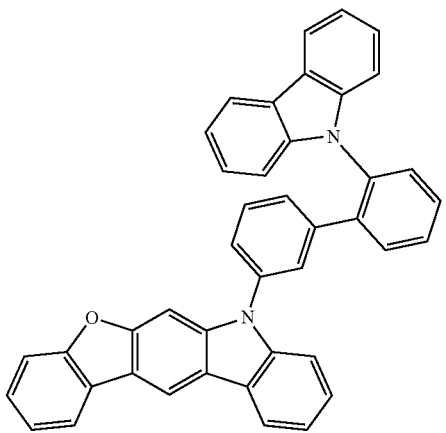

35

-continued
36
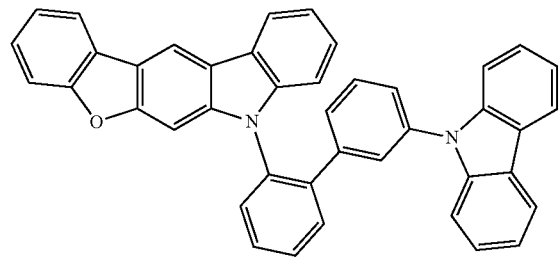
37
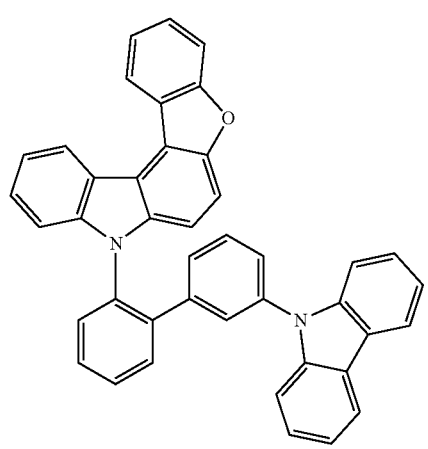
38
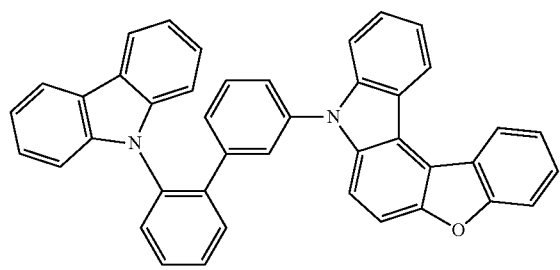
39
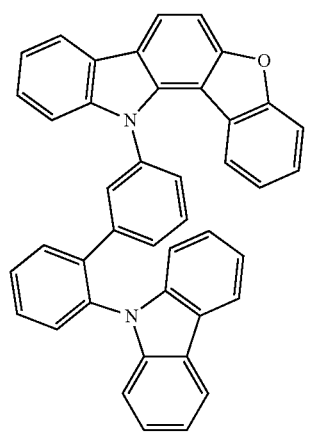
-continued
40
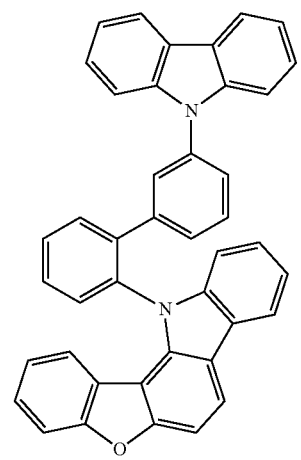
41
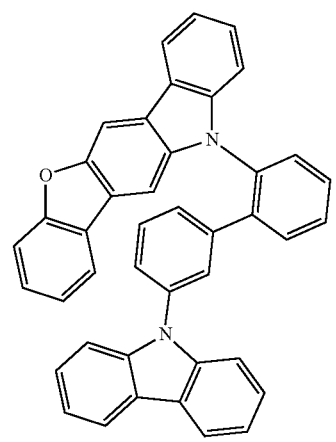
42
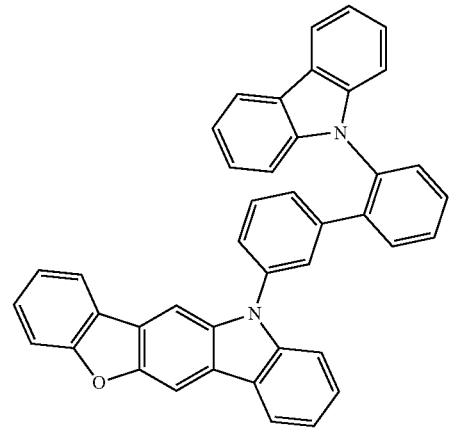

43
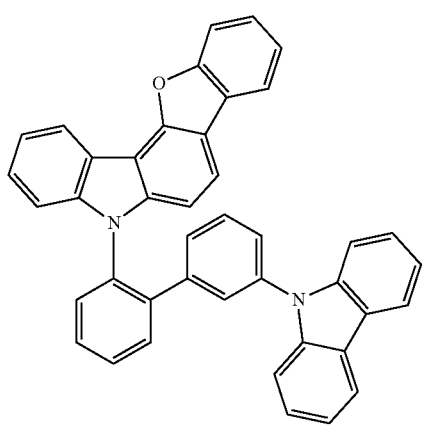
44
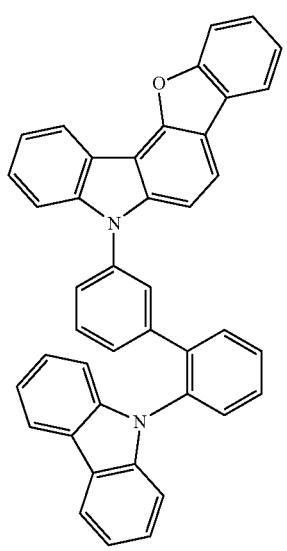
49
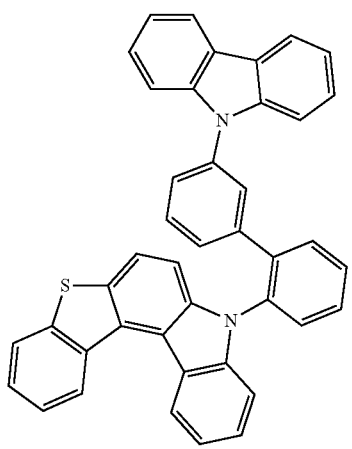
50
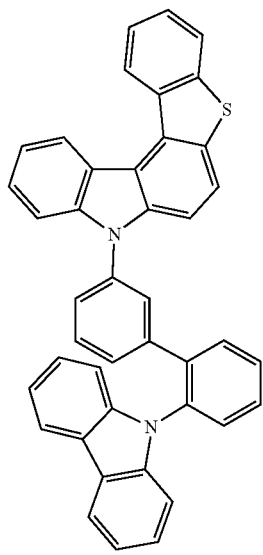
51
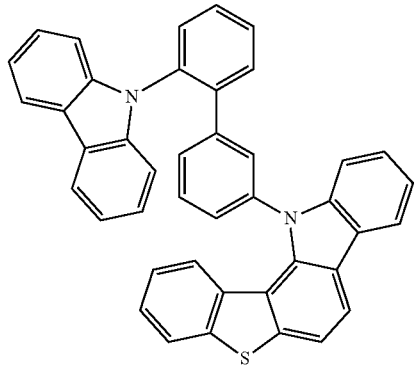
52
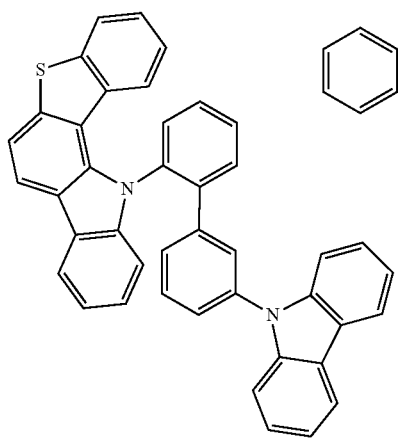

57
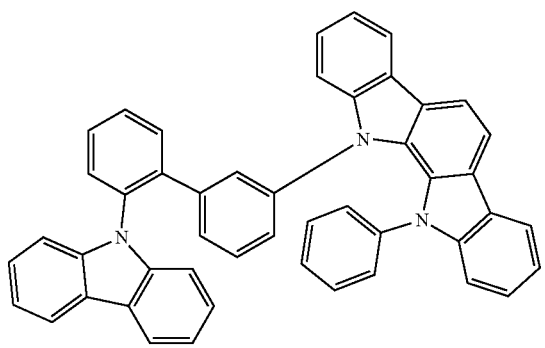
58
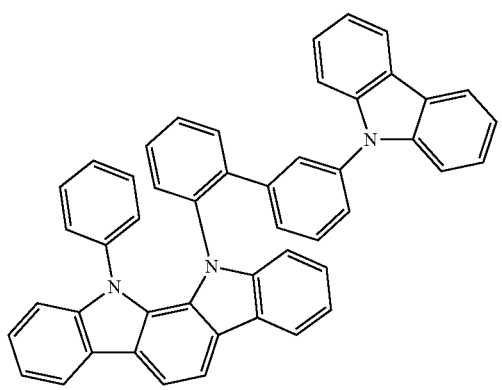
59
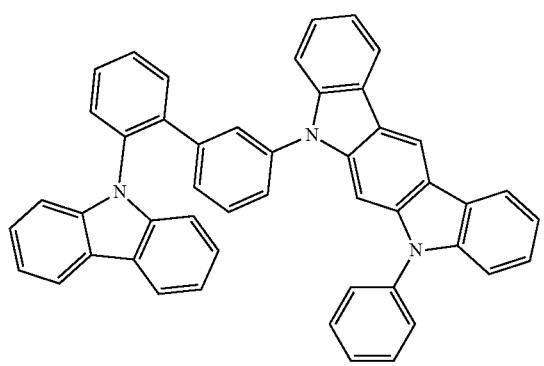
60
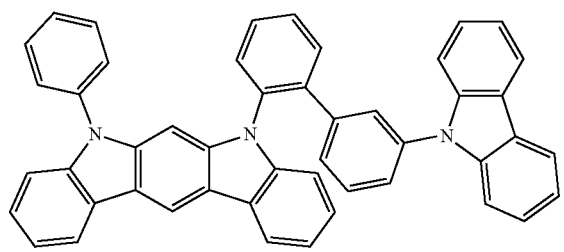
61
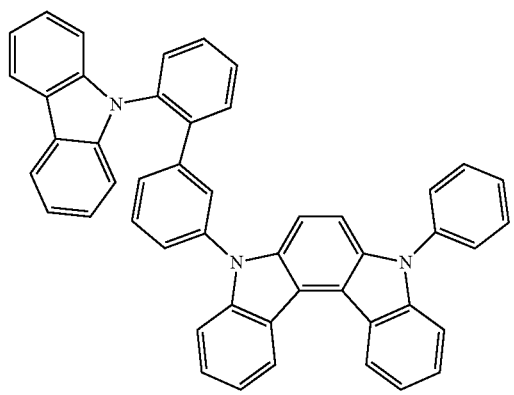
62
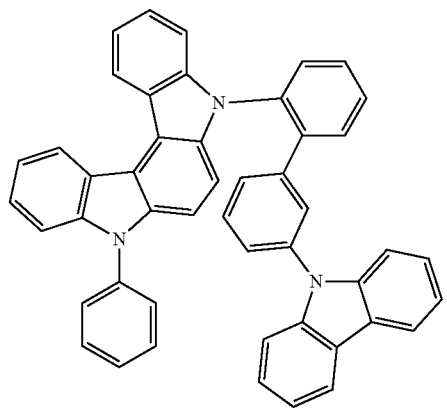
63
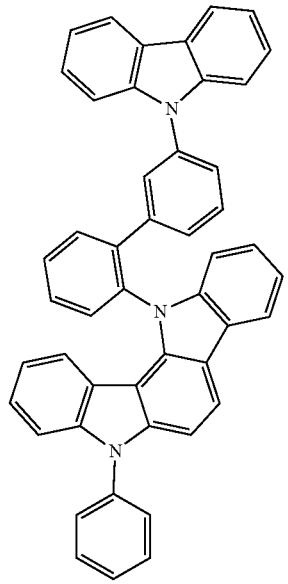

64
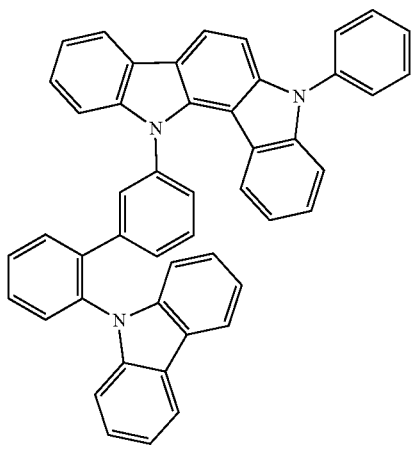
65
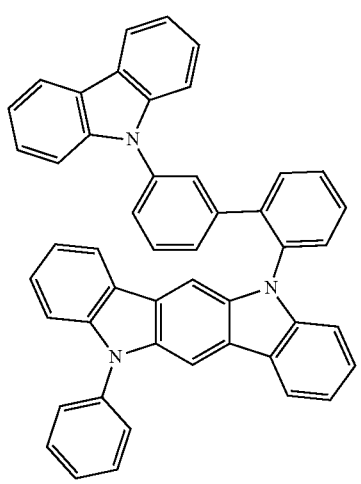
66
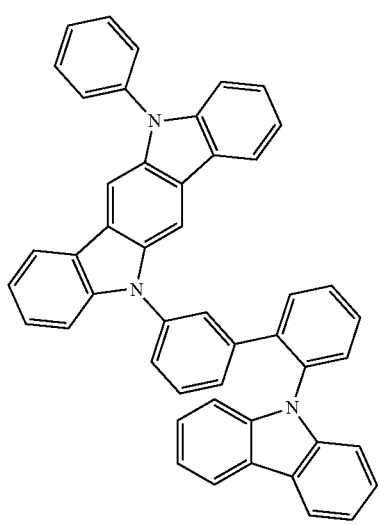
67
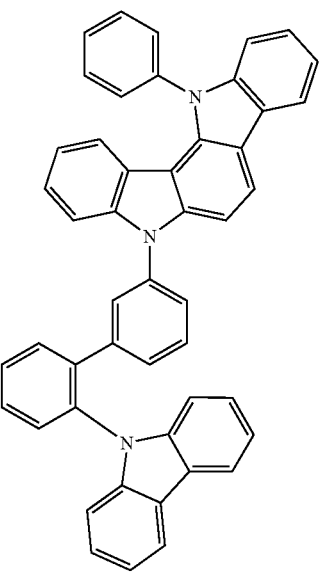
68
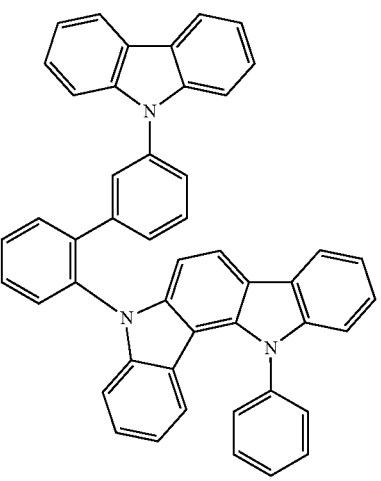
69
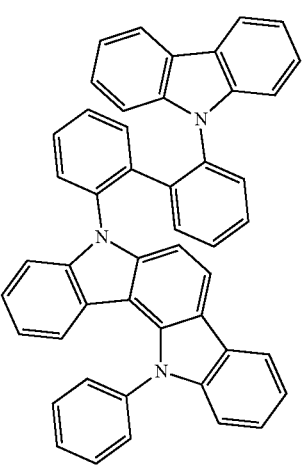

127
-continued
70
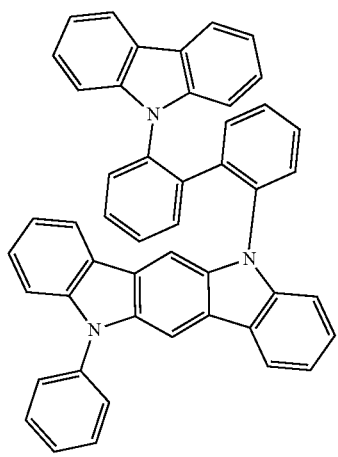
71
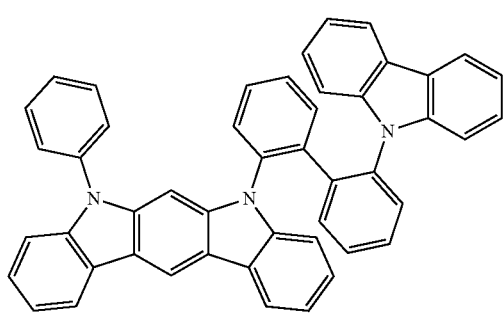
72
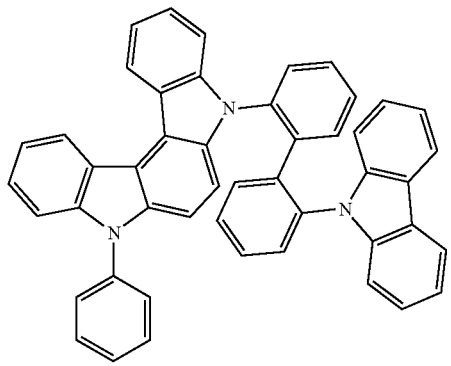
73
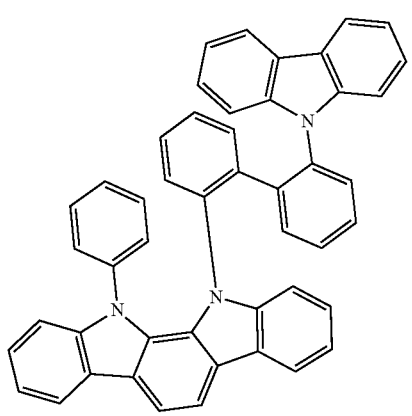
128
-continued
74
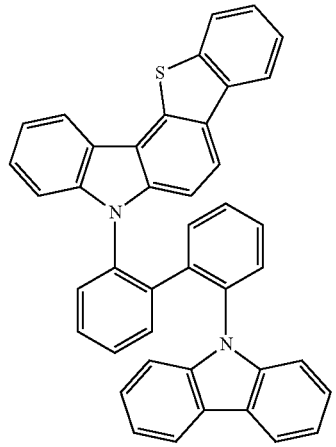
75
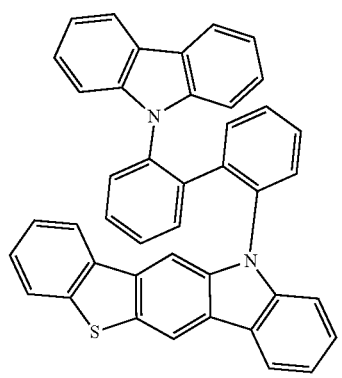
80
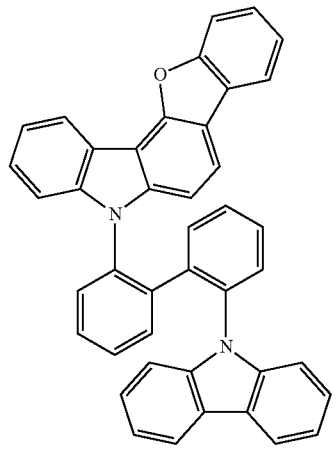
81
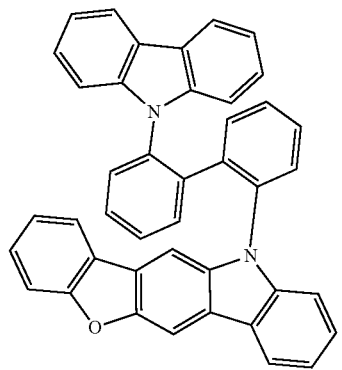

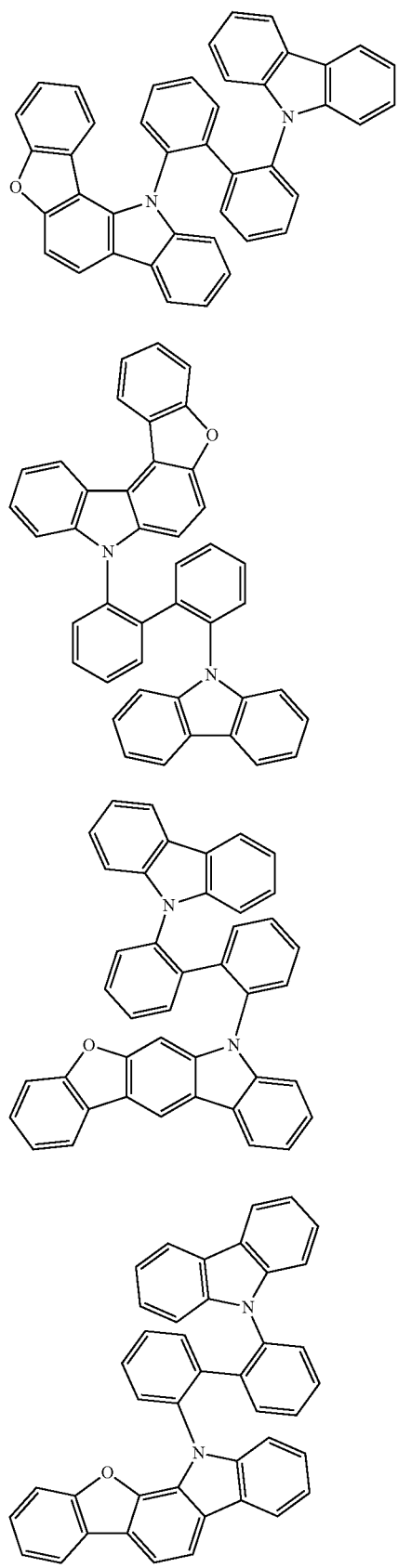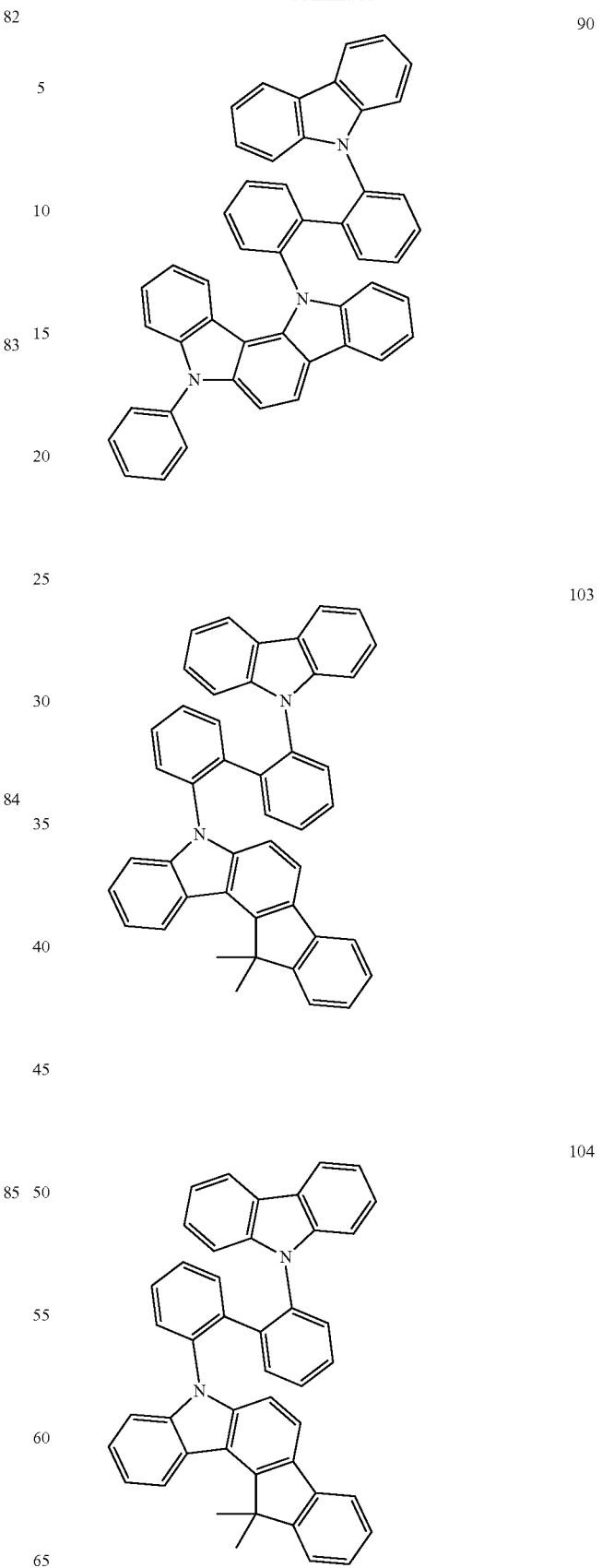

105 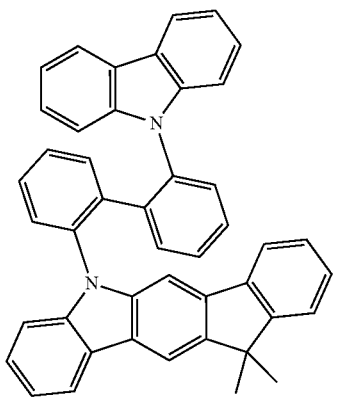

106 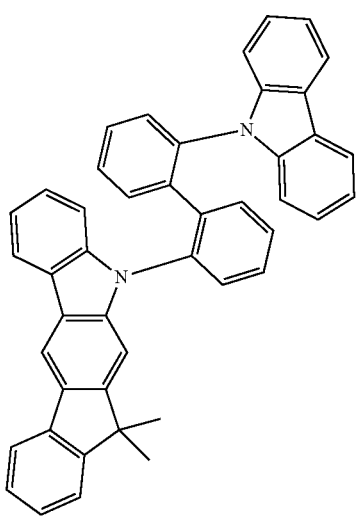

107 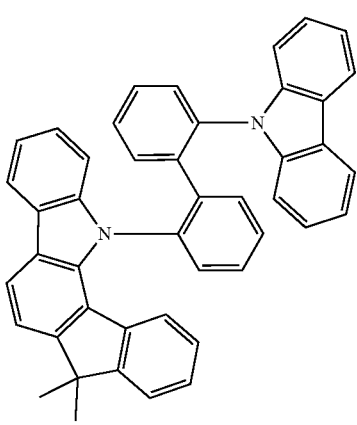

108 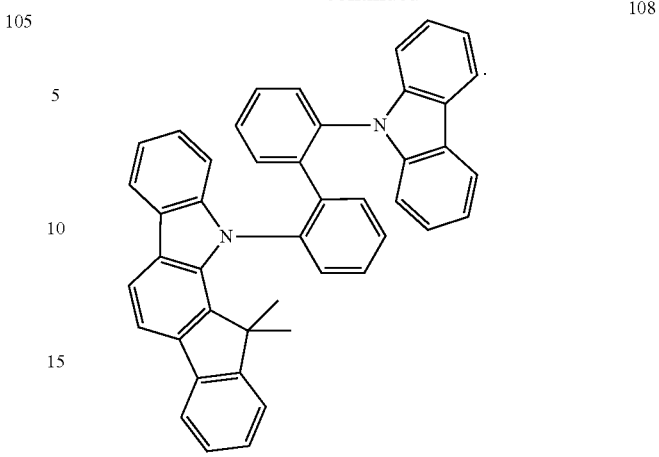

8. The organic light-emitting device of claim 1, wherein the first electrode is an anode,
the second electrode is a cathode; and
the organic layer comprises a hole transport region disposed between the first electrode and the emission layer and an electron transport region disposed between the emission layer and the second electrode;
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

9. The organic light-emitting device of claim 1, wherein an amount of the host is greater than an amount of the dopant.

10. A condensed cyclic compound represented by Formula 1:

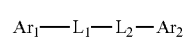

Formula 1

Formula 2

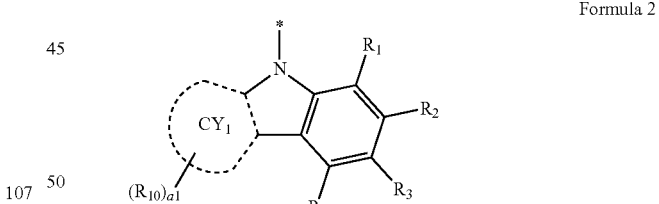

Formula 3

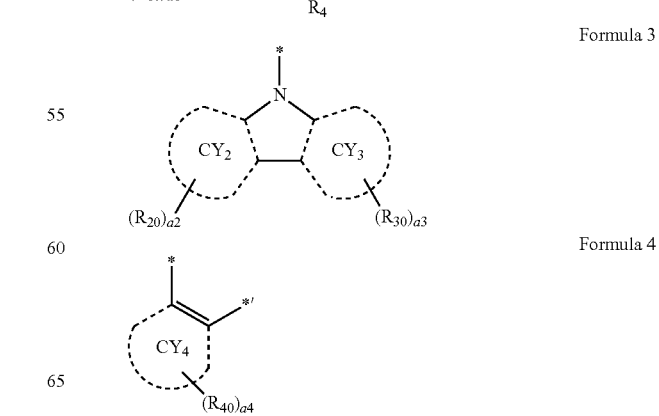

Formula 4

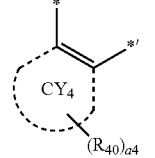

Formula 5

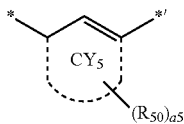

in Formulae 1 to 5,
$Ar_1$ is a group represented by Formula 2,
$Ar_2$ is a group represented by Formula 3,
$CY_1$ is selected from a fluorene group, a carbazole group, or a dibenzofuran group,
$CY_2$ and $CY_3$ are each a benzene group,
i) $L_1$ is a group represented by Formula 4 and $L_2$ is a group represented by Formula 5; ii) $L_1$ is a group represented by Formula 5 and $L_2$ is a group represented by Formula 4; or iii) $L_1$ and $L_2$ are each independently a group represented by Formula 4,
$CY_4$ and $CY_5$ are each independently selected from $C_5$-$C_{30}$ carbocyclic groups,
$R_1$ to $R_4$, $R_{10}$, $R_{20}$ and $R_{30}$ are each independently selected from a hydrogen, a deuterium, a cyano group (CN), a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_4)(Q_5)$, and $-B(Q_6)(Q_7)$,
$R_{40}$ and $R_{50}$ are each independently selected from a hydrogen, a deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_4)(Q_5)$, and $-B(Q_6)(Q_7)$,
a1 to a5 are each independently an integer of 0 to 10,
each of * and *' is a binding site to a neighboring atom,
at least one substituent of the substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, substituted $C_3$-$C_{60}$ heteroarylalkyl group, substituted monovalent non-aromatic condensed polycyclic group and substituted monovalent non-aromatic condensed heteropolycyclic group is selected from:
a deuterium, $-CD_3$, $-CD_2H$, $-CDH_2$, a cyano group, a $C_1$-$C_{60}$ alkyl group, a $C_2$-$C_{60}$ alkenyl group, a $C_2$-$C_{60}$ alkynyl group and a $C_1$-$C_{60}$ alkoxy group;
a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, $-CD_3$, $-CD_2H$, $-CDH_2$, a cyano group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, $-Si(Q_{11})(Q_{12})(Q_{13})$, $-N(Q_{14})(Q_{15})$ and $-B(Q_{16})(Q_{17})$;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a Co-Coo aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group and a monovalent non-aromatic condensed heteropolycyclic group, each substituted with at least one selected from a deuterium, $-CD_3$, $-CD_2H$, $-CDH_2$, a cyano group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$); and —Si($Q_{31}$)($Q_{32}$)($Q_{33}$), —N($Q_{34}$)($Q_{35}$) and —B($Q_{36}$)($Q_{37}$), and $Q_1$ to $Q_7$, $Q_{11}$ to $Q_{17}$, $Q_{21}$ to $Q_{27}$ and $Q_{31}$ to $Q_{37}$ are each independently selected from a hydrogen, a deuterium, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group and a substituted or unsubstituted monovalent non-aromatic condensed heteropolycyclic group.

11. The condensed cyclic compound of claim 10, wherein $Ar_1$ is selected from groups represented by Formulae 2-1 to 2-6, and $Ar_2$ is selected from a group represented by Formula 3-7:

Formula 2-1

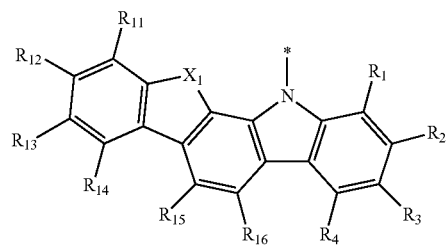

Formula 2-2

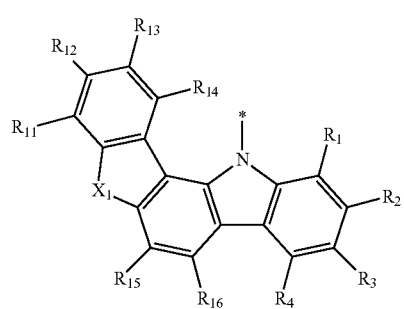

Formula 2-3

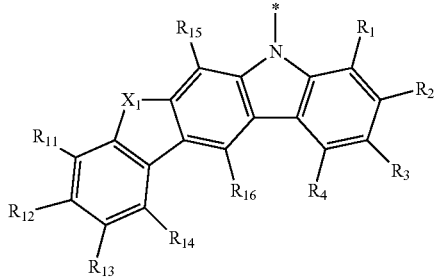

Formula 2-4

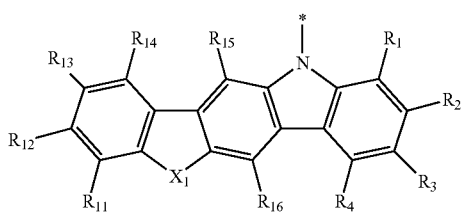

Formula 2-5

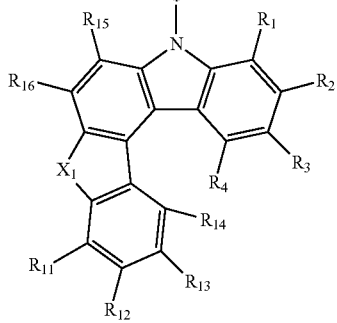

Formula 2-6

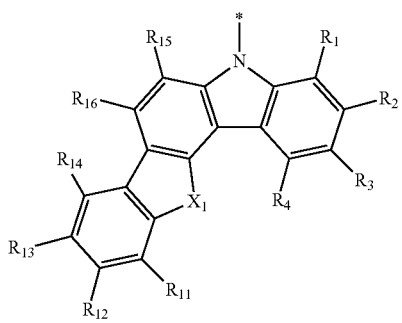

Formula 3-7

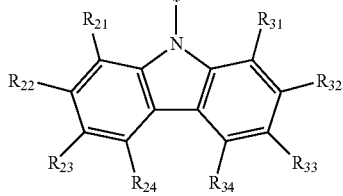

in Formulae 2-1 to 2-6 and 3-7, $X_1$ is C($R_{17}$)($R_{18}$), N($R_{19}$), or O, $R_1$ to $R_4$ are each independently the same as described in claim 10, $R_{11}$ to $R_{19}$ are each independently the same as $R_{10}$ in claim 10, $R_{21}$ to $R_{24}$ are each independently the same as $R_{20}$ in claim 10, R_{31} to R_{34} are each independently the same as R_{30} in claim 10, and is a binding site to a neighboring atom.

12. The condensed cyclic compound of claim 10, wherein CY_{4} and CY_{5} are each independently selected from a benzene group, a naphthalene group, a fluorene group, a carbazole group, a dibenzofuran group, and a dibenzothiophene group.

13. The condensed cyclic compound of claim 10, wherein the condensed cyclic compound is represented by one of Formulae 1-1 to 1-3:

Formula 1-1
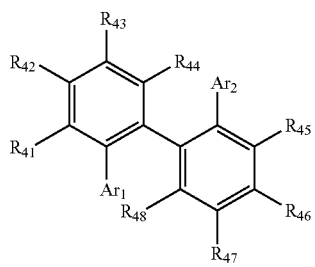

Formula 1-2
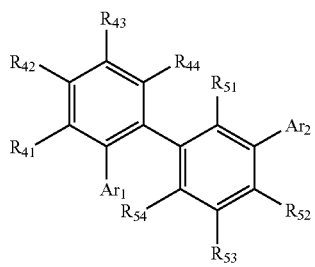

Formula 1-3
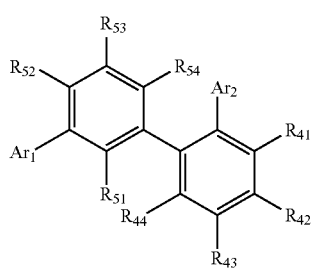

in Formulae 1-1 to 1-3,

Ar_{1} and Ar_{2} are the same as in claim 10,

R_{41} to R_{48} are each independently the same as R_{40} in claim 10, and

R_{51} to R_{54} are each independently the same as R_{50} in claim 10.

14. The condensed cyclic compound of claim 10 being selected from Compounds 33 to 44, 57 to 73, 80-85, 90, or 103 to 108:

33
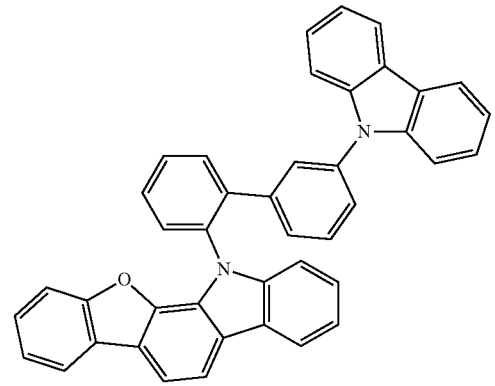

34
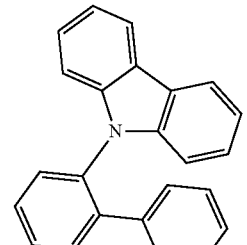

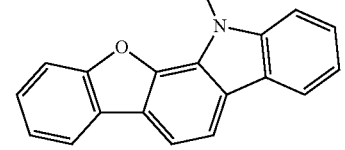

35
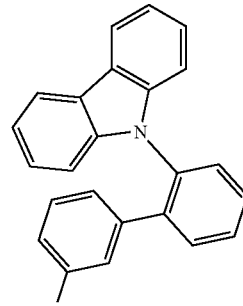

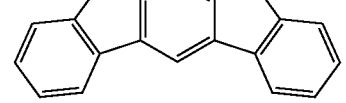

36
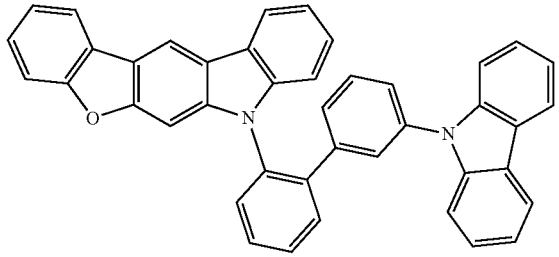

37
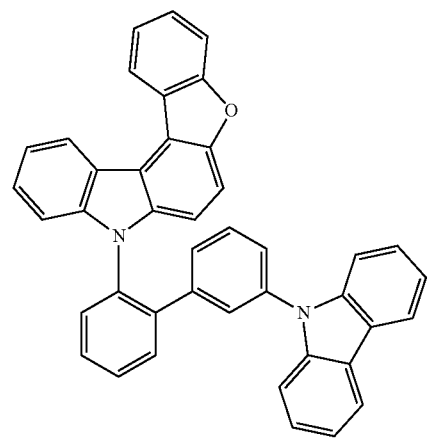
38
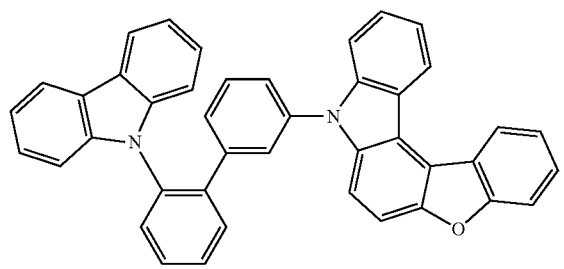
39
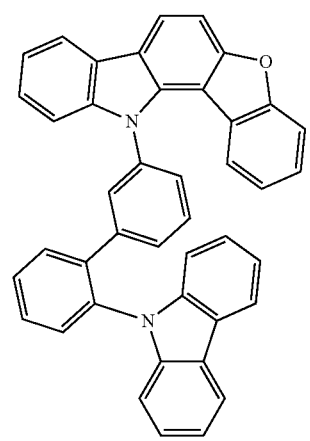
40
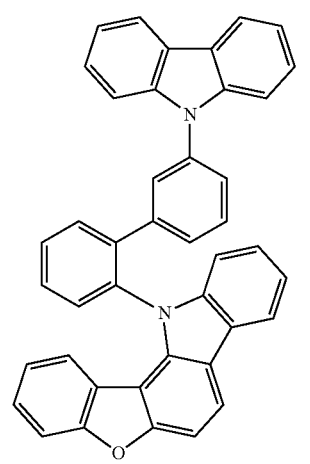
41
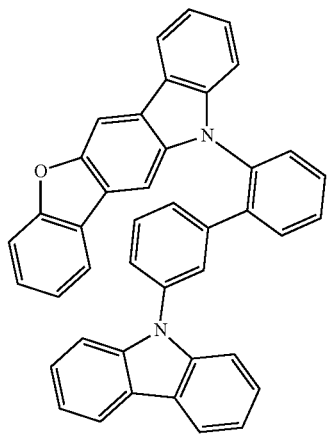
42
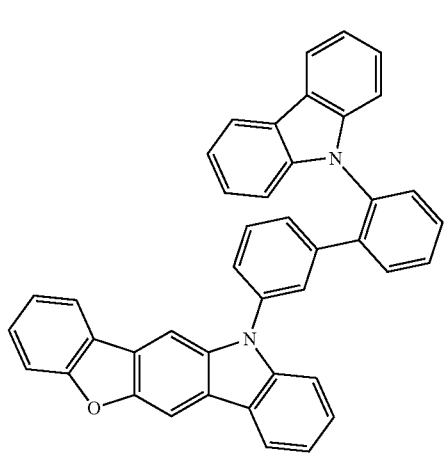
43
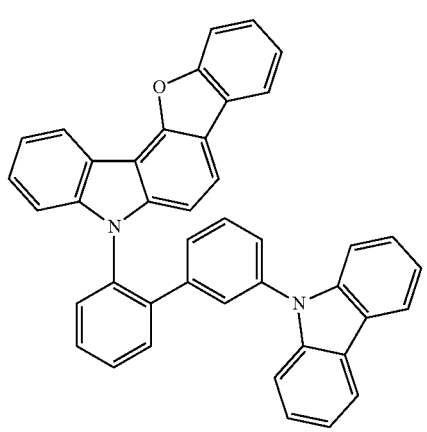

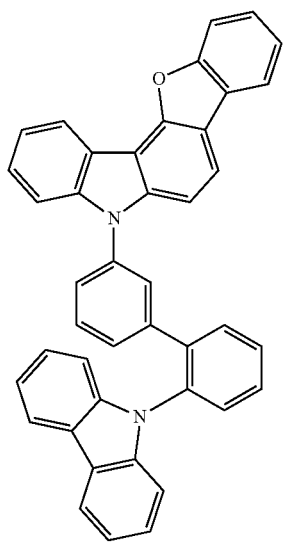
44
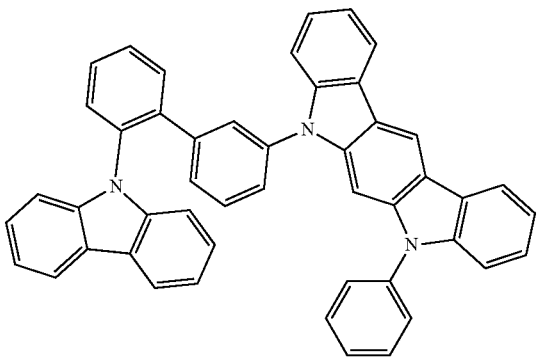
59
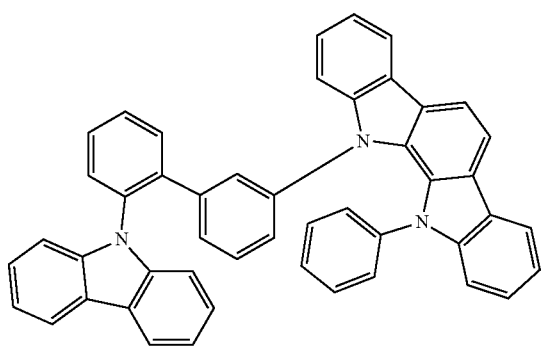
57
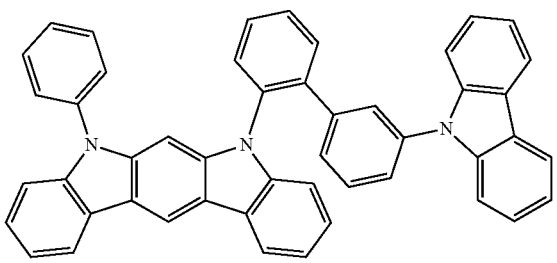
60
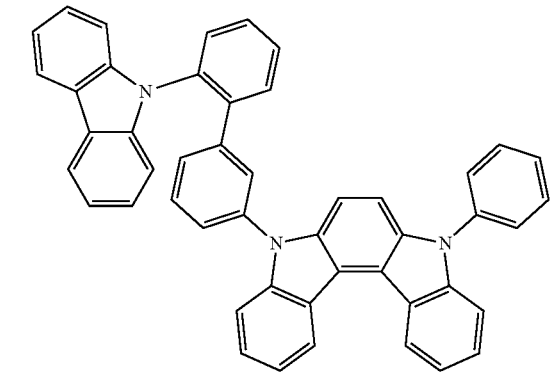
61
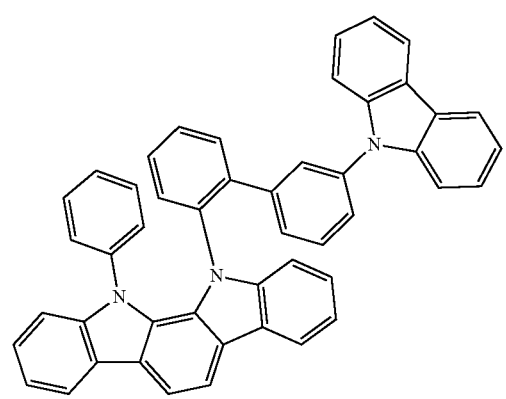
58
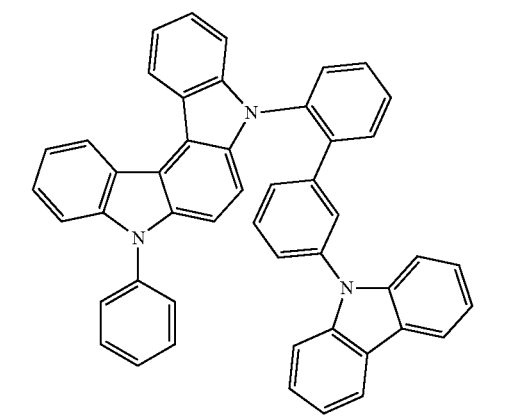
62

63
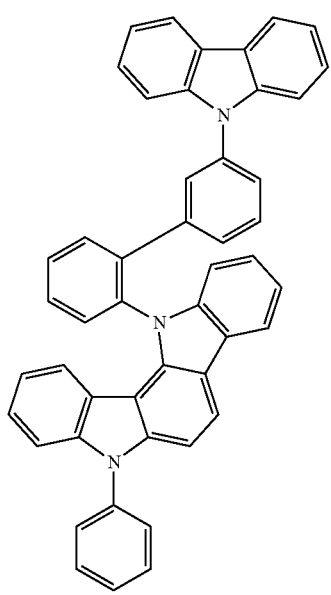
64
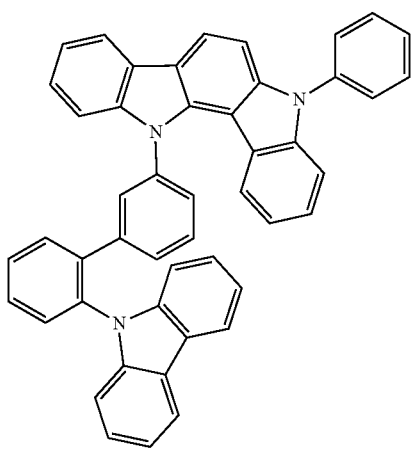
65
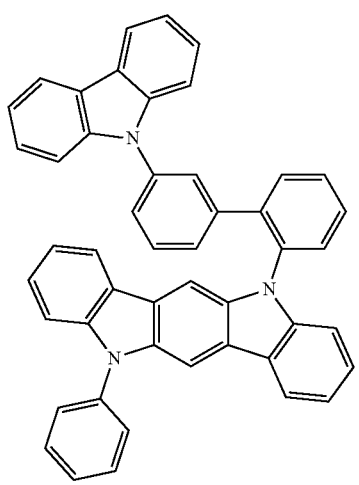
66
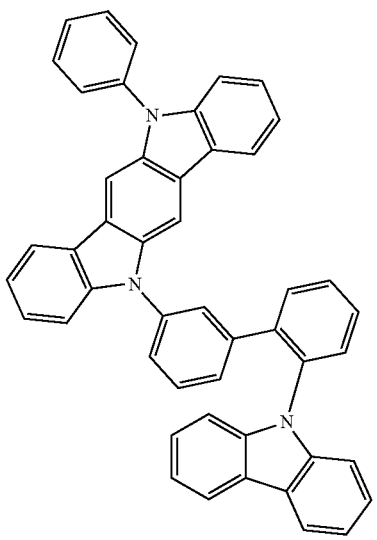
67
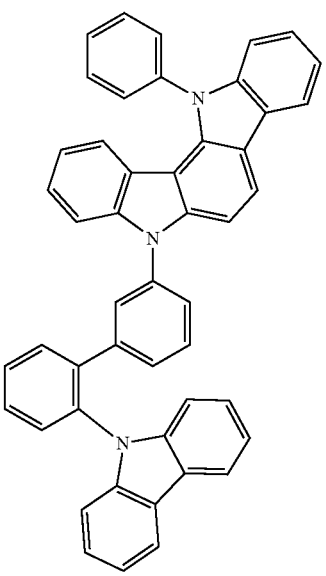
68
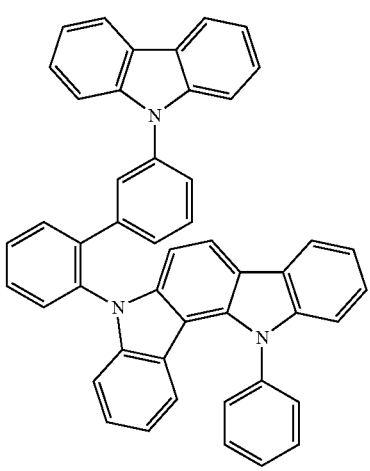

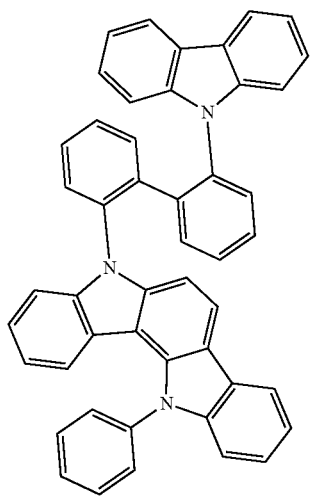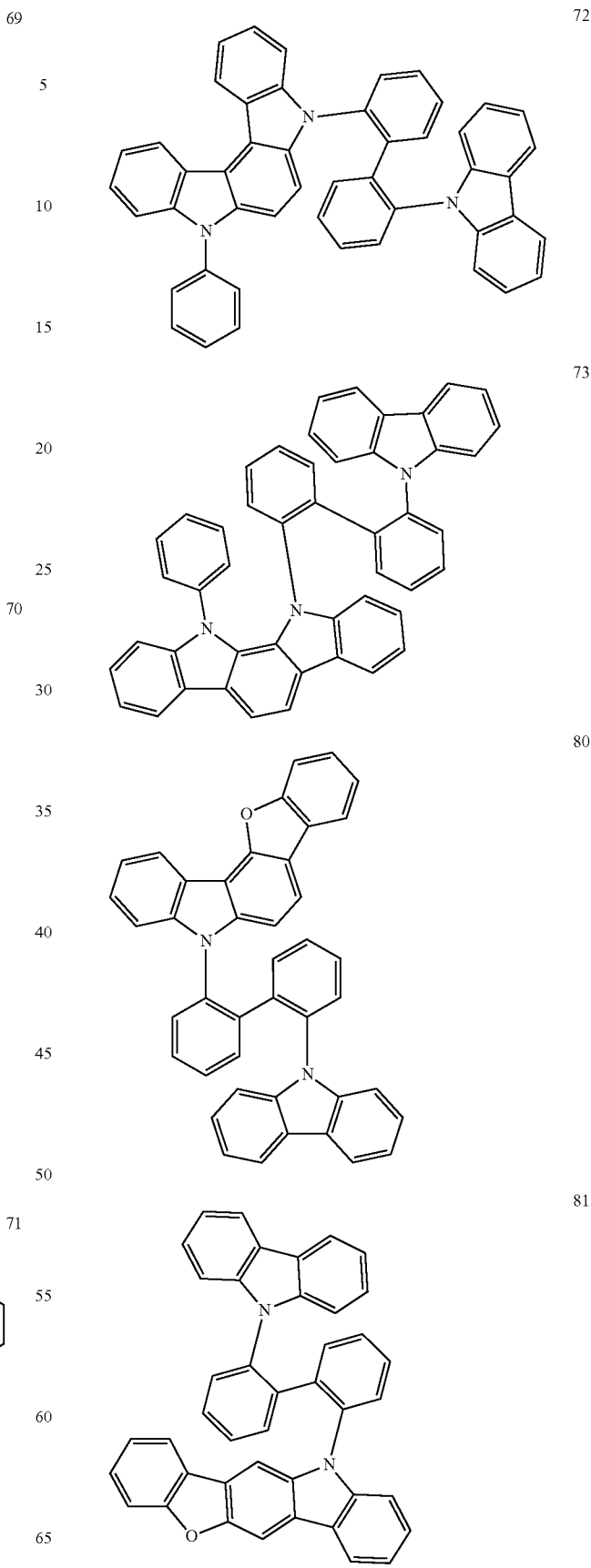

82
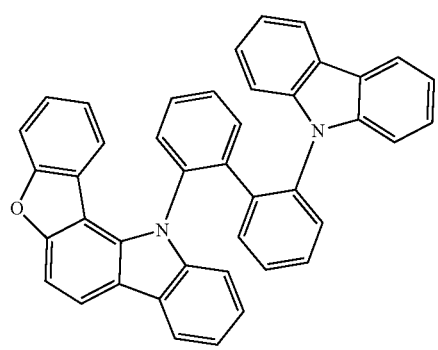
83
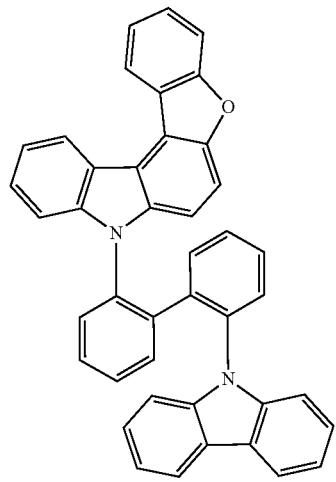
84
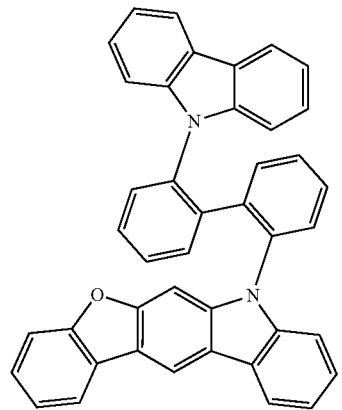
85
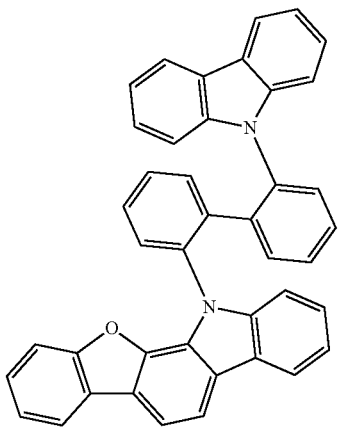
90
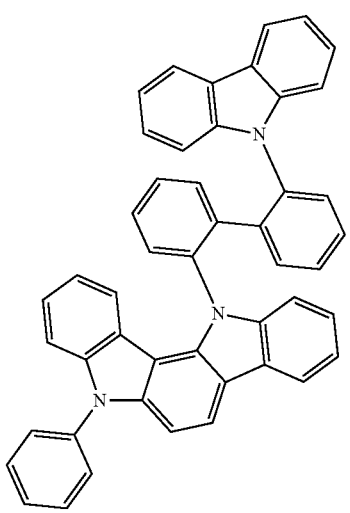
103
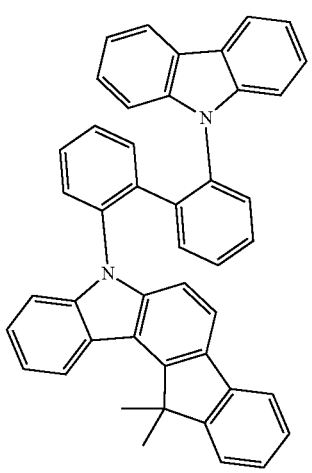

-continued
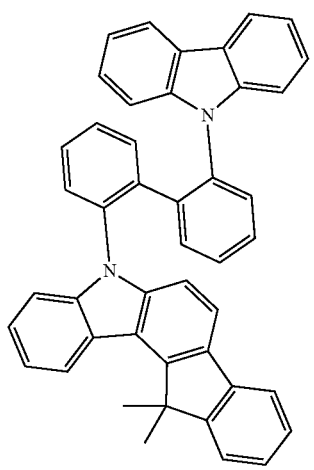
104
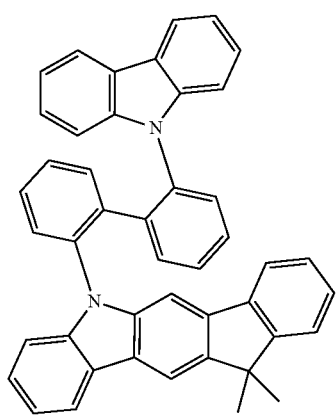
105
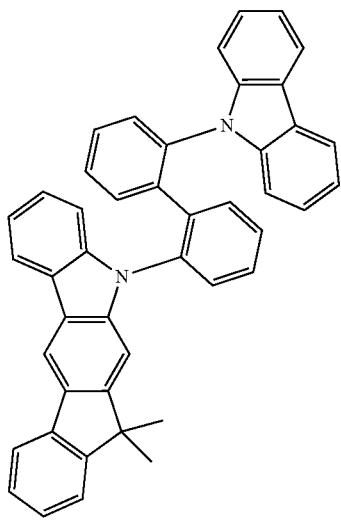
106
-continued
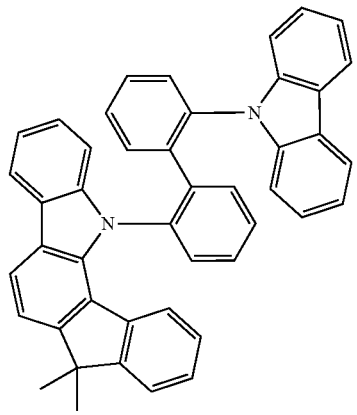
107
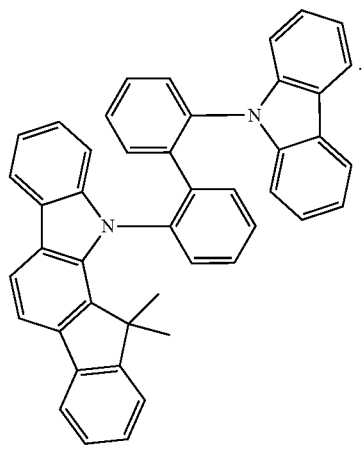
108
* * * * *